US011278549B2

(12) United States Patent
Steinberg et al.

(10) Patent No.: US 11,278,549 B2
(45) Date of Patent: Mar. 22, 2022

(54) METHOD OF TREATING OBESITY

(71) Applicant: McMaster University

(72) Inventors: Gregory Steinberg, Ancaster (CA); Alex Green, Hamilton (CA)

(73) Assignee: McMaster University, Ontario (CA)

( * ) Notice: Subject to any disclaimer, the term of this patent is extended or adjusted under 35 U.S.C. 154(b) by 66 days.

(21) Appl. No.: 15/948,092

(22) Filed: Apr. 9, 2018

(65) Prior Publication Data

US 2018/0318298 A1 Nov. 8, 2018

Related U.S. Application Data

(63) Continuation-in-part of application No. 14/767,645, filed as application No. PCT/CA2014/000113 on Feb. 14, 2014, now Pat. No. 9,937,173.

(60) Provisional application No. 61/765,161, filed on Feb. 15, 2013, provisional application No. 62/492,385, filed on May 1, 2017.

(51) Int. Cl.
| | |
|---|---|
| *A61K 31/505* | (2006.01) |
| *A61K 31/7088* | (2006.01) |
| *A61K 31/713* | (2006.01) |
| *C07K 16/40* | (2006.01) |
| *A61K 31/48* | (2006.01) |

(52) U.S. Cl.
CPC ............ *A61K 31/505* (2013.01); *A61K 31/48* (2013.01); *A61K 31/7088* (2013.01); *A61K 31/713* (2013.01); *C07K 16/40* (2013.01)

(58) Field of Classification Search
CPC .............. A61K 2300/00; A61K 31/485; A61K 31/505; A61K 31/7088; C07K 16/40
See application file for complete search history.

(56) References Cited

U.S. PATENT DOCUMENTS

| | | | |
|---|---|---|---|
| 2003/0124176 A1* | 7/2003 | Hsu | A61K 31/4745 424/449 |
| 2016/0228452 A1 | 8/2016 | Kim et al. | |

FOREIGN PATENT DOCUMENTS

| | | |
|---|---|---|
| CA | 2505299 A1 | 6/2004 |
| KR | 20160108258 | 6/2016 |
| KR | 1020160107610 | 9/2016 |
| KR | 20170108914 | 9/2017 |
| WO | 2012/058598 A1 | 5/2012 |
| WO | 2013/116538 A1 | 8/2013 |

OTHER PUBLICATIONS

Aronne, L.J. Classification of obesity and assessment of obesity-related health risks. Obesity Research, 2002, 10, Suppl. 2:105S-115S.*
Yamada, J., et al. Hyperglycemia induced by the 5-HT receptor agonist, 5-methoxytryptamine, in rats: involvement of the peripheral 5-HT2a receptor. Eur. J. Pharmacol., 1997, 323:235-240.*
W. Ono: "Adipocyte Differentiation Induced by Adipose-derived Serotonin in relation to Regulatory Mechanism of Metabolic Syndrome Pathosis", Therapeutic Research 2006,27(7), 1300-1303. see whole document.
International Search Report of PCT/CA2014/000113 dated Jun. 2, 2014.
Written Opinion of PCT/CA2014/000113 dated Jun. 2, 2014.
CIPO Examination Notes of PCT/CA2014/000113.
Mistry et al.; "Effect of Sarpogrelate in High Fat Diet Induced Obesity in Rats", 2011, Asian J Pharm Biol Res, vol. 1(4), pp. 441-446.
Hansson et al., Serotonin (5-HT) and 5-HT2A Receptor Agonists Suppress Lipolysis in Primary Rat Adipose Cells, Biochem. Biophys Res Commun. 2016.
Oh et al., "Regulation of Systemic Energy Homeostasis by Serotonin in Adipose Tissues", Nature Communications 2015, pp. 1-13.

* cited by examiner

*Primary Examiner* — Prema M Mertz
(74) *Attorney, Agent, or Firm* — Gowling WLG (Canada) LLP

(57) ABSTRACT

A method of treating obesity and obesity-related disorders in a mammal is provided. The method comprises the step of administering to the mammal a compound or entity that inhibits the HTR2a receptor.

11 Claims, 37 Drawing Sheets

Specification includes a Sequence Listing.

f

Figure 10
a
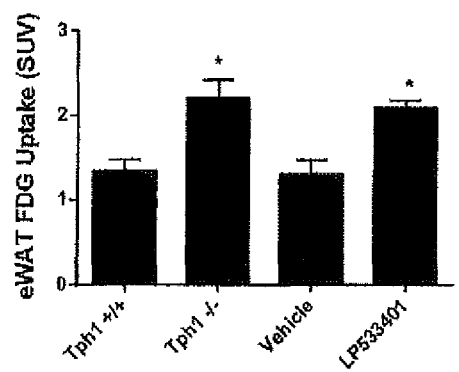
b
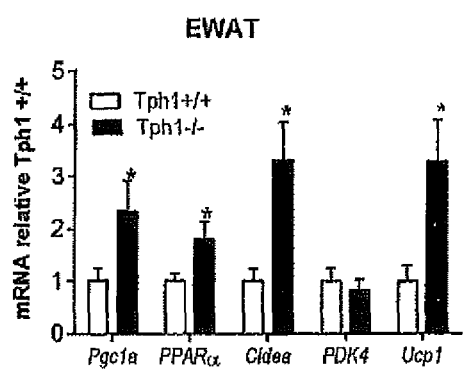
c
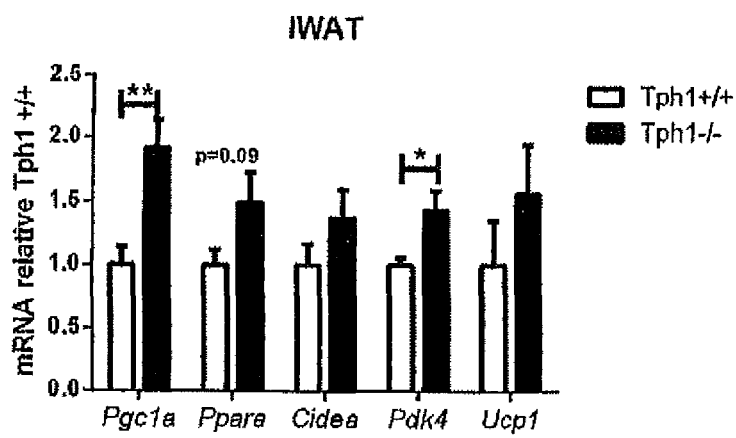

```
          10         20         30         40         50         60
   MIEDNKENKD HSLERGRASL IFSLKNEVGS LIKALKIFQE KHVNLLHIES RKSKRRNSEF 70         80         90        100        110        120
   EIFVDCDINR EQLNDIFHLL KSHTNVLSVN LPDNFTLKED GMETVPWFPK KISDLDHCAH 130        140        150        160        170        180
   RVLMYGSELD ADHPGFKDNV YRKRRKYFAD LAMNYKHGDP IPKVEFTEEE IKTWGTVFQE 190        200        210        220        230        240
   LNKLYPTHAC REYLKNLPLL SKYCGYREDN IPQLEDVSNF LKERTGFSIR PVAGYLSPRD 250        260        270        280        290        300
   FLSGLAFRVF HCTQYVRHSS DPFYTPEPDT CHELLGHVPL LAEPSFAQFS QEIGLASLGA 310        320        330        340        350        360
   SEEAVQKLAT CYFFTVEFGL CKQDGQLRVF GAGLLSSISE LKHALSGHAK VKPFDPKTTC 370        380        390        400        410        420
   KQECLITTFQ DVYFVSESFE DAKEKMREFT KTIKRPFGVK YNPYTRSIQI LKDTKSITSA 430        440
   MNELQHDLDV VSDALAKVSR KPSI
```

B) Figure 12 cont'd

```
   1 ttttagagaa ttactccaaa ttcatcatga ttgaagacaa taaggagaac aaagaccatt
  61 ccttagaaag gggaagagca agtctcattt tttccttaaa gaatgaagtt ggaggactta
 121 taaaagccct gaaaatcttt caggagaagc atgtgaatct gttacatatc gagtcccgaa
 181 aatcaaaaag aagaaactca gaatttgaga ttttgttga ctgtgacatc aacagagaac
 241 aattgaatga tatttttcat ctgctgaagt ctcataccaa tgttctctct gtgaatctac
 301 cagataattt tactttgaag gaagatggta tggaaactgt tccttggttt ccaaagaaga
 361 tttctgacct ggaccattgt gccaacagag ttctgatgta tggatctgaa ctagatgcag
 421 accatcctgg cttcaaagac aatgtctacc gtaaacgtcg aaagtatttt gcggacttgg
 481 ctatgaacta taaacatgga gacoccattc caaaggttga attcactgaa gaggagatta
 541 agacctgggg aaccgtattc caagagctca acaaactcta cccaacccat gcttgcagag
 601 agtatctcaa aaacttacct ttgcttccta aatattgtgg atatcgggag gataatatcc
 661 cacaattgga agatgtctcc aacttttttaa aagagcgtac aggttttttcc atccgtcctg
 721 tggctggtta cttatcacca agagatttct tatcaggttt agcctttcga gttttttcact
 781 gcactcaata tgtgagacac agttcagatc ccttctatac cccagagcca gatacctgcc
 841 atgaactctt aggtcatgtc ccgcttttgg ctgaacctag ttttgccaa ttctcccaag
 901 aaattggctt ggcttctctt ggcgcttcag aggaggctgt tcaaaaactg gcaacgtgct
 961 acttttttcac tgtggagttt ggtctatgta aacaagatgg acagctaaga gtctttggtg
1021 ctggcttact ttcttctatc agtgaactca aacatgcact ttctggacat gccaaagtaa
1081 agcccttttga tcccaagatt acctgcaaac aggaatgtct tatcacaact tttcaagatg
1141 tctactttgt atctgaaagt tttgaagatg caaaggagaa gatgagagaa tttaccaaaa
1201 caattaagcg tccatttgga gtgaagtata atccatatac acggagtatt cagatcctga
1261 aagacacaaa gagcataacc agtgccatga atgagctgca gcatgatctc gatgttgtca
1321 gtgatgccct tgctaaggtc agcaggaagc cgagtatcta acagtagcca gtcatccagg
1381 aacatttgag catcaattcg gaggtctggg ccatctcttg ctttccttga acacctgatc
1441 ctggagggac agcatcttct ggccaaacaa tattatcgaa ttccactact taaggaatca
1501 ctagtctttg aaaatttgta cctggatatt ctatttacca cttatttttt tgtttagttt
1561 tattttctttt ttttttttggt agcagcttta atgagacaat ttatatacca tacaagccac
1621 tgaccaccca tttttaatag agaagttgtt tgacccaata gatagatcta atctcagcct
1681 aactctattt tccccaatcc tccttgagta aaatgaccct ttaggatcgc ttagaataac
1741 ttgaggagta ttatggcgct gactcatatt gttacctaag atcccttat ttctaaagta
1801 totgttactt attgc
```

```
  1 miednkenke nkdhssergr vtlifslene vgglikvlki fqenhvsllh losrkskqrn
 61 sefeifvdcd isreqlndif pllkshatvl svdspdqlta kedvmetvpw fpkkisdldf
121 canrvllygs eldadhpgfk dnvyrrrrky faelamnykh qdpipkieft eeelktwgti
181 frelnklypt hacreylrnl pllskycgyr ednlpqledv snflkertgf sirpvagyls
241 prdflsglaf rvfhctqyvr hssdplytpe pdtchellgh vpllaepsfa qfsqeiglas
301 lgaseetvqk lateyfftve fglckqdgql rvfgagllss lselkhalsg hakvkpfdpk
361 iackqeclit sfqdvyfvse sfedakekmr efaktvkrpf glkynpytqs vqvlrdtkai
421 tsamnelryd ldvisdalar vtrwpsv
```

B)

```
   1 gactctttaa actccagtgg ctctgaggtg agtgggtgag tgggatagcc cctccctggg
  61 acatcggatc agaagactcc cagcaaggac gggatcaact tctagtagga accagattca
 121 ccatgattga agacaacaag gagaacaaag agaacaaaga ccattcctcc gaaagaggga
 181 gagtgactct catcttctcc ttggagaatg aagtcggagg actcataaaa gtgctgaaaa
 241 tcttccagga gaatcatgtg agcctgttac acatcgagtc ccggaaatca aagcaaagaa
 301 attcagaatt tgagatattt gttgactgcg acatcagccg agaacagttg aatgacatct
 361 tccccctgct gaagtcgcac gccaccgtcc tctcggtgga ctcgcccgat cagctcactg
 421 cgaaggaaga cgttatggag actgtccctt ggtttccaaa gaagatttct gacctggact
 481 tctgcgccaa cagagtgctg ttgtatggat ccgaacttga cgccgaccac cctggcttca
 541 aagacaatgt ctatcgtaga agacgaaagt attttgcaga gttggctatg aactacaaac
 601 atgggaccc cattcccaag attgaattca cggaagaaga gattaagacc tgggggacca
 661 tcttccgaga gctaaacaaa ctctacccga cccacgcctg cagggagtac ctcagaaacc
 721 tccctttgct ctcaaaatac tgtggctatc gggaagacaa catcccgcaa ctggaggatg
 781 tctccaactt tttaaaagaa cgcactgggt tttccatccg tcctgtggct ggttacctct
 841 caccgagaga ttttctgtcg gggttagcct ttcgagtctt tcactgcact cagtatgtga
 901 gacacagttc agatccctc tacactccag agccagacac ctgccatgaa ctcctaggcc
 961 acgttcctct cttggctgaa cccagttttg ctcaattctc ccaagaaatt ggcctggctt
1021 ccctttggagc ttcagaggag acagttcaaa aactggcaac gtgtacttt tcaactgtgg
1081 agtttgggct gtgcaaacaa gatggacagc tgagagtctt tgggcggcc ttgctttctt
1141 ccatcagtga actcaaacat gcactttctg gacatgccaa agtcaagccc tttgatccca
1201 agattgcctg taaacaggaa tgtctcatca cgagcttcca ggatgtctac tttgtatctg
1261 agagctttga agatgcaaag gagaagatga gagaatttgc caagacgtg aagcgcccgt
1321 ttggactgaa gtacaacccg tacacacaga gtgttcaggt tctcagagac accaagagca
1381 taactagtgc catgaatgag ttgcggtatg accttgatgt catcagtgat gccctcgcta
1441 gggtcaccag gtggcccagt gtgtgatggt ttccagtgca tatccaaaaa gcctttgagc
1501 atcagtctag agccagggct agttcttgct tcccctgaag acctgcttgg ggagggacag
1561 cagctcccag cttagcaatg tctctcgcct ctctccatat toaatcactc actctctctg
1621 aaaatgcaca cctggaactg cttatcttct actctgttt tgtcttctgg aacctgctga
1681 gggaaatata gttcacgtgc cacgtgatgc ccaggacaca catttaaaat attttatttc
1741 attaaaatgt aattgaatca ttctctccct tcccttttctt ccctccaacc cctccctctc
1801 aaattcatgg cctttctacc aaatgcccgt ctttgatggg tgagttgtct gacactggcc
1861 agagctggac tcatggtgat gccattttcc ccagcccatc attagtggat ggctctctg
1921 gatgccacga tgaatgtgtc tgttacctat tactgactgt gtgacagcc aggcacagtc
1981 acacactaga cttcaagggg actcgctgaa acagaagtgt ggatgacttt gcgctagagc
2041 atggctagta aagtgcaagc tggcttcaag tgctgtgtca gacagggacg tagaagccac
2101 caagactcag ccagtgcttt ctggcacttt gtttcaaggt gtaacctag gatatagtga
2161 gaaggtatgt gtgtgtgtgt gggtggtgc agagggtagg aaatggggat gggaatggag
2221 aaggggcaaa gggagcagtt tgtatctgag actgtactta tgcgagggag agctgtgagg
2281 attggagcac atgtggtgtc cgcataagca gttgtataag cttttcacta ctgtaacaaa
2341 gtgtcaggga caatcagctt atacagagaa aaggttttctc ttggatgctt tggtccatta
2401 gaagttgttc ccgtggttta agccactggt gaagcaaggc atgataggag aatgtgacag
```

Figure 14
A.
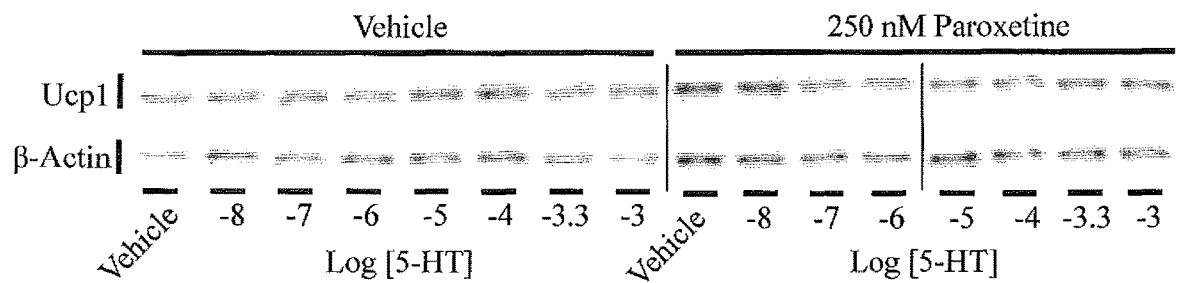
B.
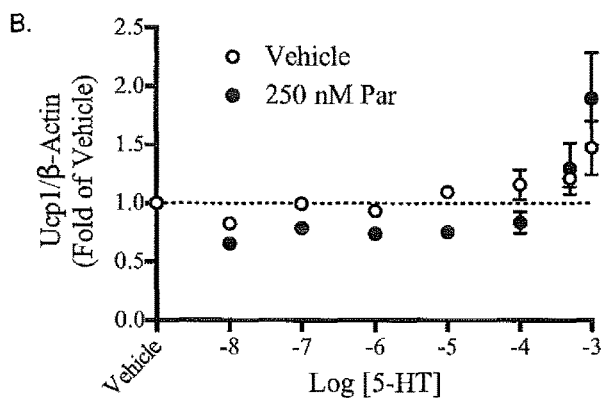
C.
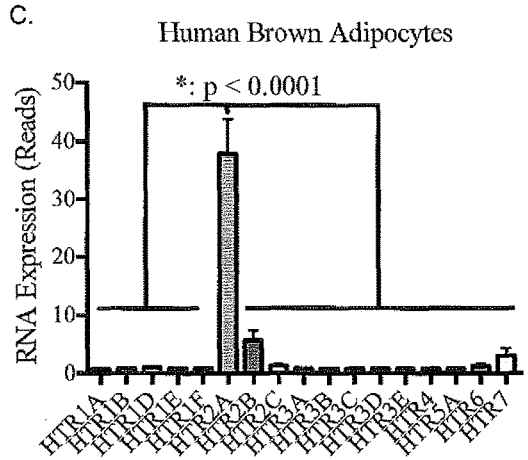
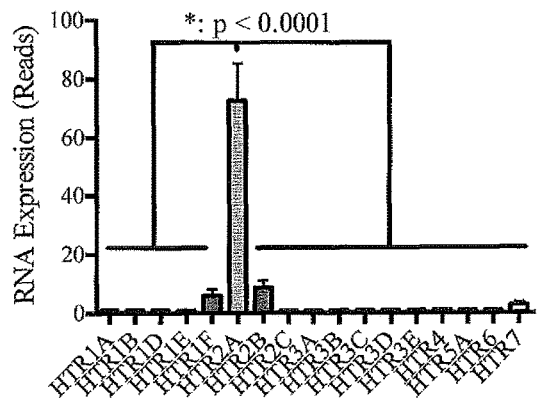

D.

| Agonist | EC$_{50}$ | |
|---|---|---|
| | Mean (nM) | SEM (nM) |
| 5-HT | 189.9 | 63.2 |
| TCB-2 | 144.8 | 97.1 |
| AL-34662 | 55.1 | 17.1 |
| NBOH-2C-CN | 36.4 | 35.8 |

Figure 15

| COMPOUND | CONNECTIVITY SCORE | COMPOUND | MECHANISM OF ACTION |
|---|---|---|---|
| I | 0.4873 | Altanserin | Htr2a antagonist |
| II | 0.4856 | Lysergol | Weak Htr2a agonist |
| III | 0.485 | Pimozide | Htr2a, Htr7, D2, D3 and D4 antagonist |
| IV | 0.4845 | Midostaurin | $Ca^{2+}$/DAG-dependent PKC isoform inhibitor |
| V | 0.4672 | Isoxicam | COX1 and COX2 Inhibitor |
| VI | 0.4647 | Nortriptyline | NET and Htr2a antagonist |

Figure 18 - continued
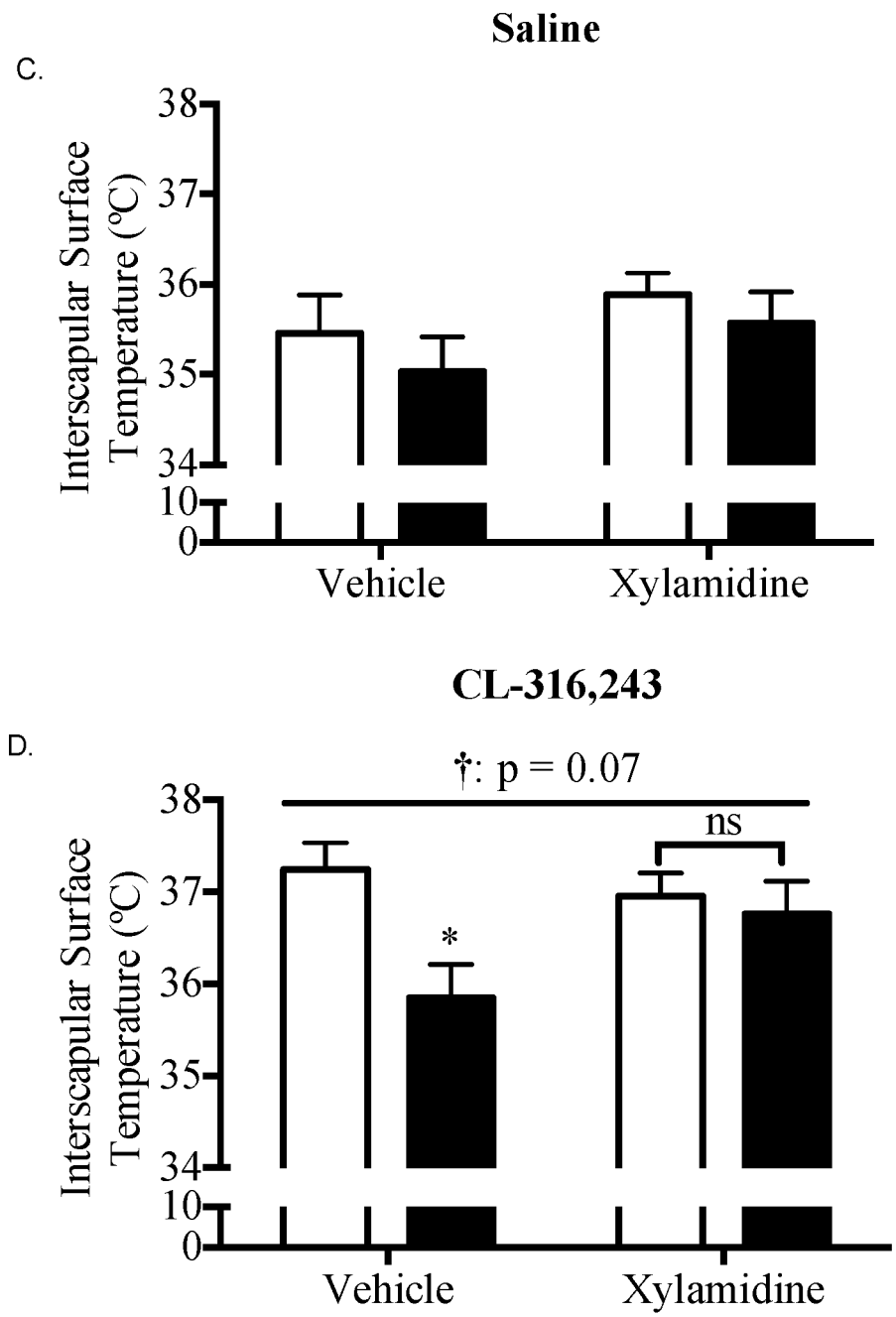

Figure 19
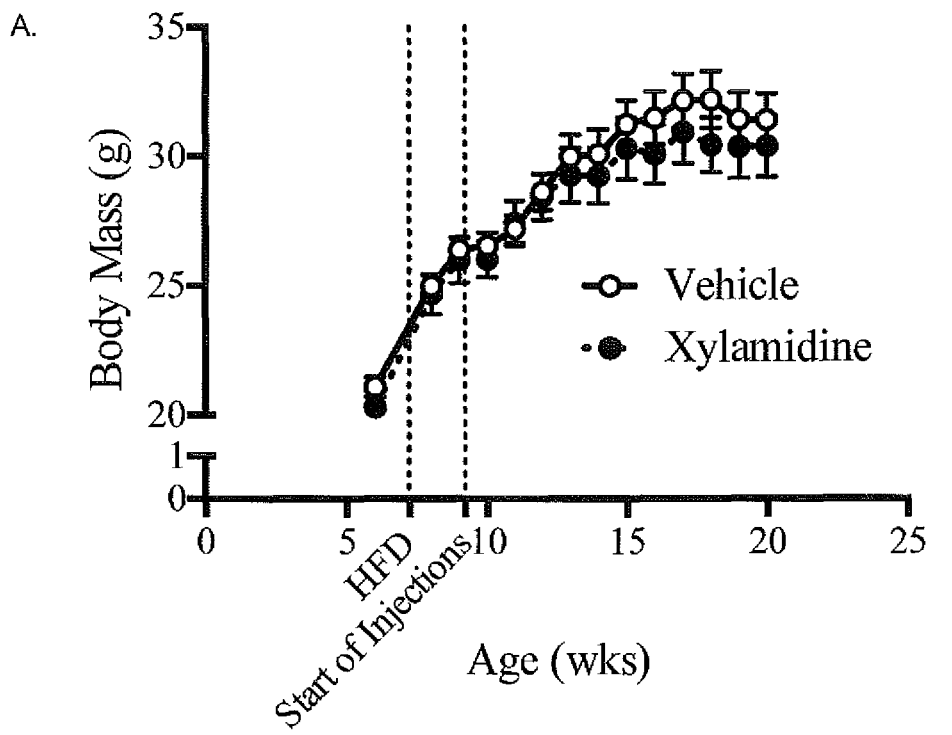
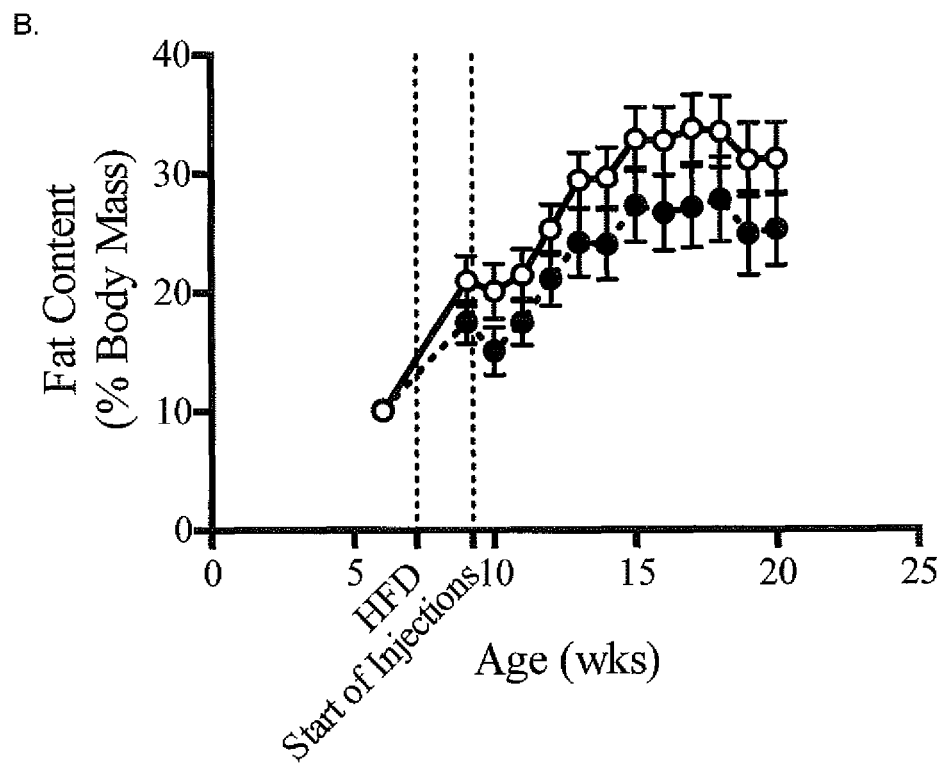

Figure 19 continued
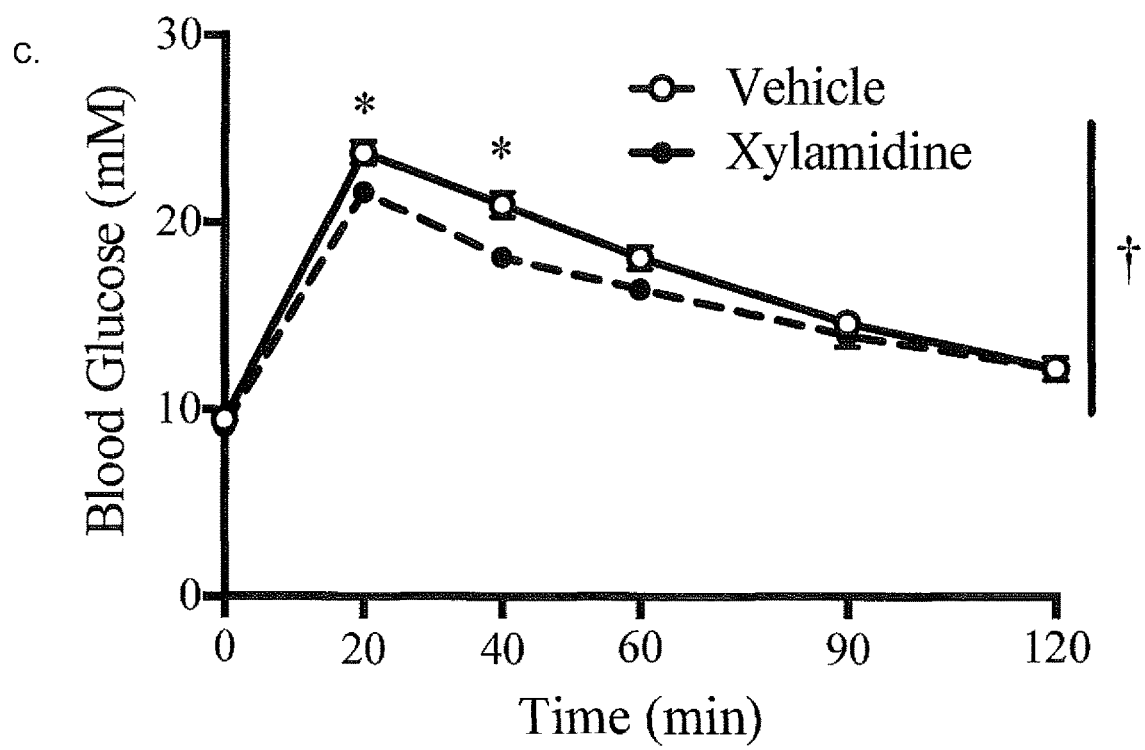
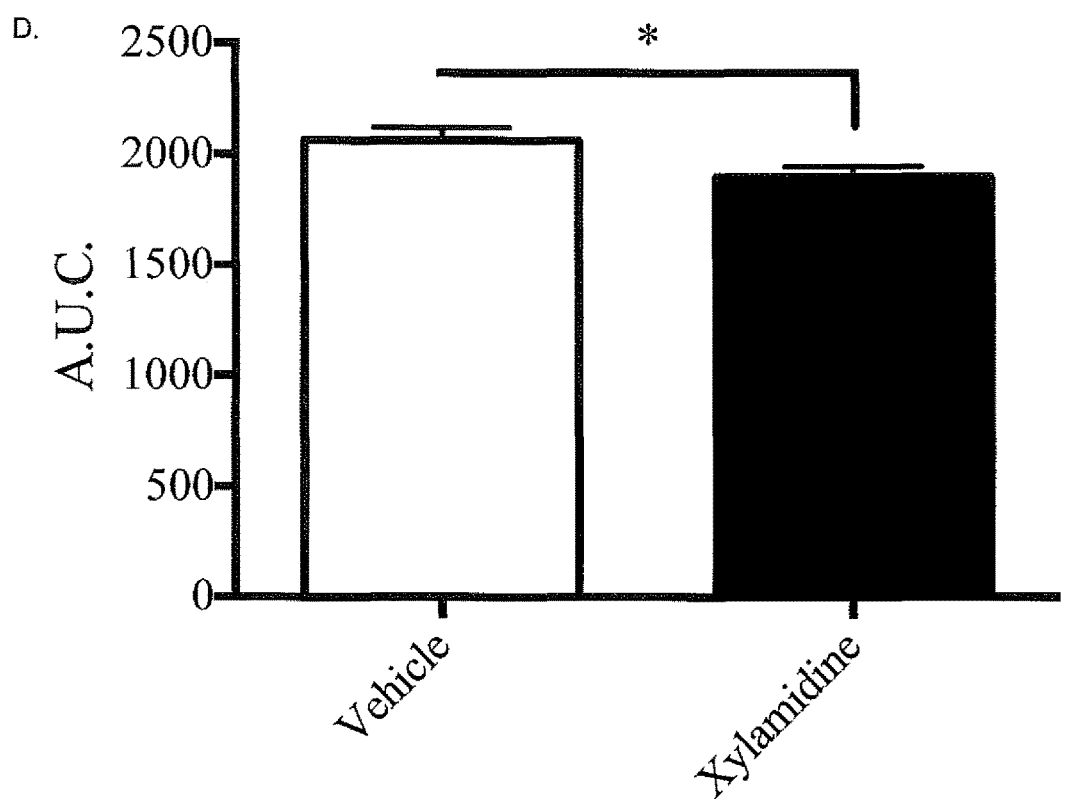

Figure 19 continued
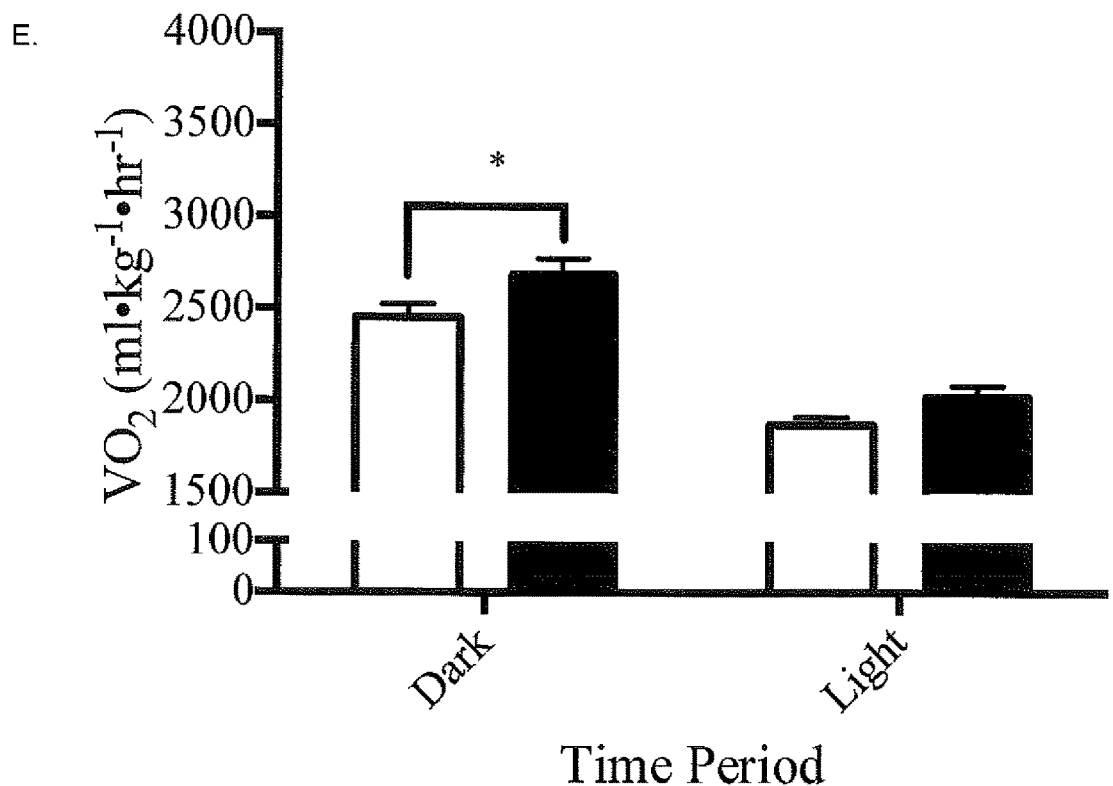
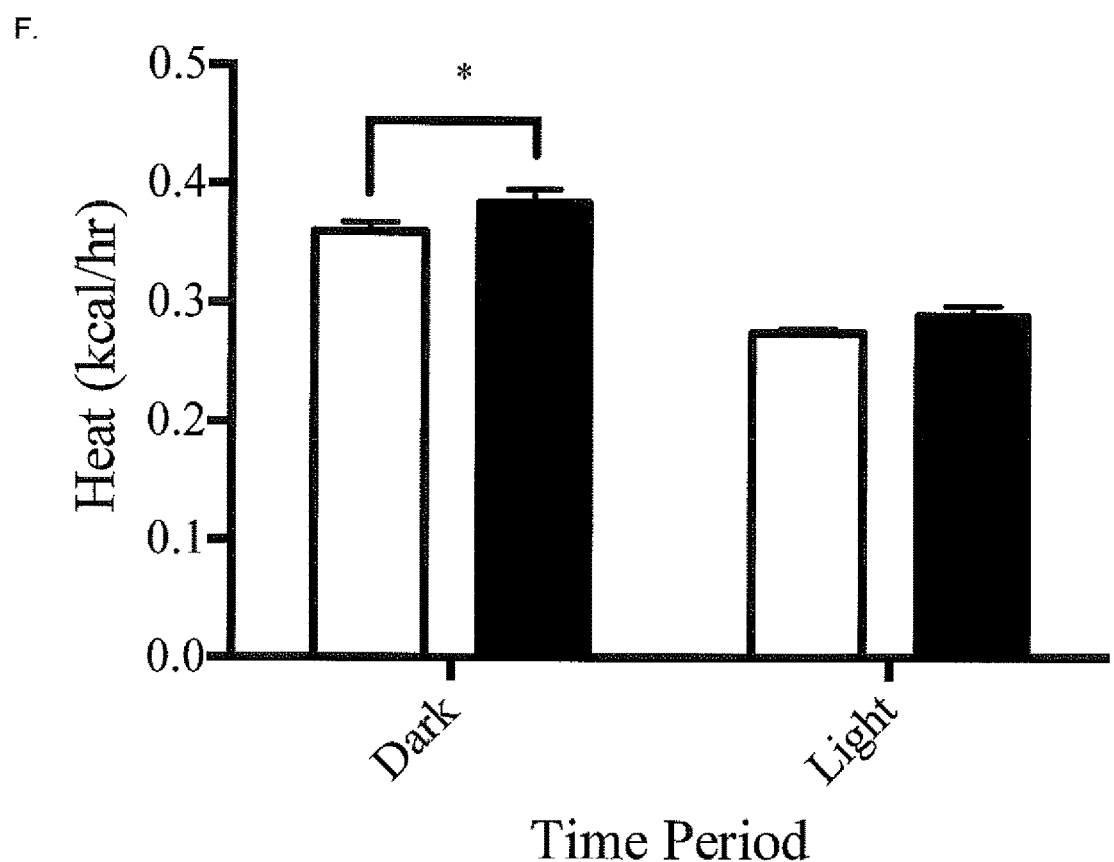

Figure 24
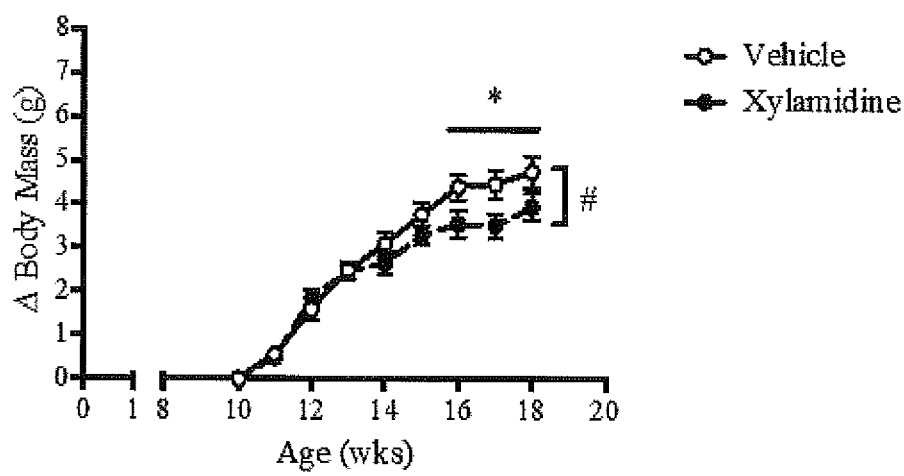
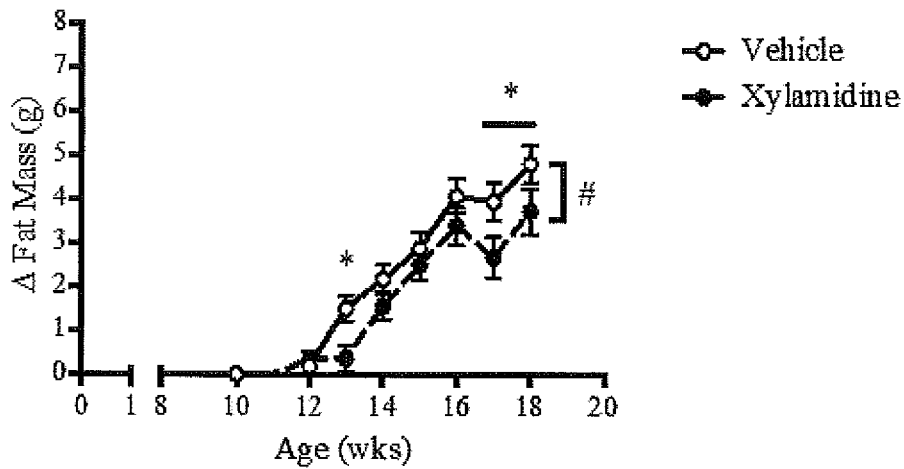

METHOD OF TREATING OBESITY

FIELD OF THE INVENTION

The present invention generally relates to methods of treating obesity and related disorders using inhibitors of peripheral serotonin.

BACKGROUND OF THE INVENTION

Obesity results from a chronic energy imbalance in which energy expenditure is less than energy intake. Brown adipose tissue (BAT) is an important regulator of energy expenditure via its expression of mitochondrial uncoupling protein 1 (UCP1), and the ectopic expression of UCP1 in mice protects against the development of obesity and its related complications including insulin resistance and diabetes. In contrast, the deletion of UCP1 in mice results in greater obesity when mice are housed at thermoneutrality (30° C.), but not at 22° C., where compensatory thermogenic mechanisms, such as shivering, are active. Importantly, positron emission tomography (PET) imaging has indicated that BAT is less active in humans with both aging and obesity. However, the mechanisms mediating reductions in BAT activity are not currently understood.

Serotonin, also known as 5-hydroxytryptamine (5-HT), is a biogenic amine that has been studied extensively for its role in regulating behavior, appetite and energy expenditure via the central nervous system; functions that are largely conserved across all phyla that have a nervous system. Despite the extensive understanding of serotonin in the brain, the vast majority of serotonin (~95%) in the body is found in the periphery where it is produced by the enzyme, tryptophan hydroxylase 1 (Tph1) which catalyzes the rate-limiting step in the synthesis of 5-HT from dietary tryptophan. Tph1 is genetically distinct from Tph2 which predominates in the brain stem and enteric neurons.

Mice deficient in Tph1 (Tph1$^{-/-}$) have been generated that exhibit very low levels of circulating serotonin but maintain normal levels of serotonin in the brain due to the sustained presence of Tph2 which controls central serotonin production. Tph1$^{-/-}$ mice are viable and show no behavioral differences from wild-type animals and have normal body mass and insulin sensitivity when fed a chow diet. Since serotonin does not cross the blood brain barrier, Tph1$^{-/-}$ mice have been a valuable aid in unraveling the importance of peripheral serotonin in regulating gastro-intestinal and liver inflammation, insulin secretion and bone formation.

In addition to the ancient role of serotonin in regulating energy balance in both vertebrates and invertebrates, polymorphisms in Tph1 and serotonin receptor (HTR2A) genes have recently been associated with obesity and gestational diabetes. Further, high-fat diet-induced obesity has been found to result in increased levels of circulating serotonin in mice. However, whether changes in peripheral serotonin are directly linked to obesity or to changes in energy expenditure is not currently known.

Thus, it would be desirable to determine the role of peripheral serotonin in obesity, and to develop methods of treating obesity.

SUMMARY OF THE INVENTION

It has now been found that inhibition of peripheral serotonin is useful to treat mammals that are overweight, or obese and related conditions.

Accordingly, in one aspect of the present invention, a method of treating obesity and obesity-related disorders in a mammal is provided. The method comprises the step of administering to the mammal a compound or entity that inhibits the synthesis or activity of peripheral serotonin.

In another aspect of the invention, a method of treating obesity and obesity-related disorders in a mammal is provided comprising the step of administering to the mammal a compound or entity that inhibits 5-HT2a.

In another aspect, a method of treating a mammal that is underweight or treating undesirable weight loss in a mammal is provided comprising administering to the mammal a compound or entity that increases the activity of peripheral 5-HT2a.

These and other aspects of the invention are described in the detailed description that follows by reference to the following figures.

Figure 5:
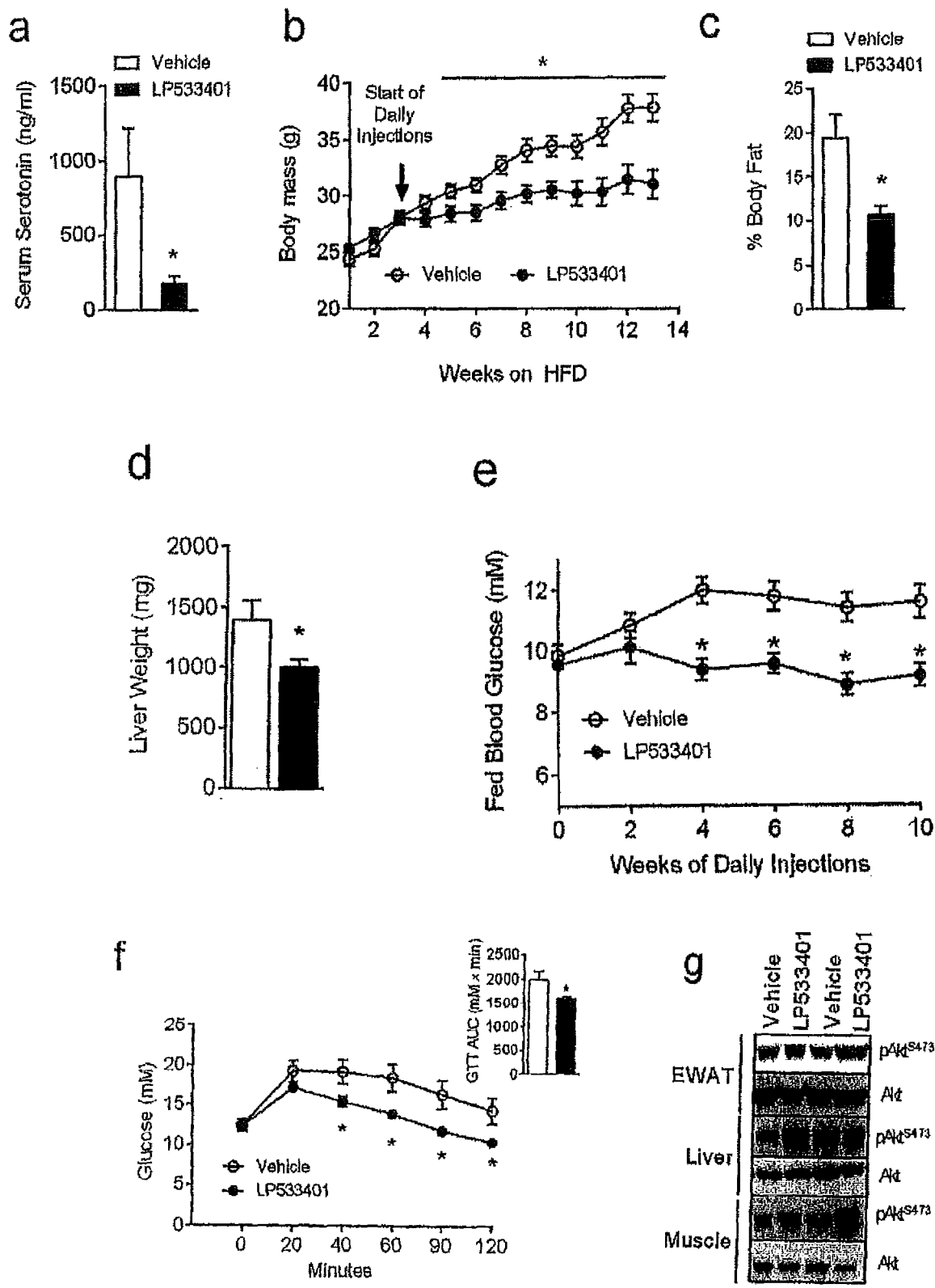

FIG. 5 illustrates that chemical inhibition of Tph1 prevents obesity and insulin resistance in C57Bl6 mice fed a high-fat diet as shown by (a) serum serotonin concentrations of HFD-fed C57Bl6 mice after 8 weeks of LP533401 or vehicle treatment, (b) body mass of HFD-fed C57Bl6 mice over 14 weeks treated with vehicle or LP533401 for the last 12 weeks, (c) adiposity and liver weights (d) of vehicle or LP533401 treated mice, (e) fed blood glucose over time, (f) GTT of vehicle and LP533401 HFD-fed mice and AUC, (g) Akt$^{S473}$ phosphorylation relative to total Akt in liver, EWAT and mixed gastrocnemius muscle from vehicle and LP533401 treated mice 15 minutes following an injection of 0.5 U/kg insulin. n=7-10. Data are mean±SEM. *P<0.05 compared to vehicle.

Figure 6:
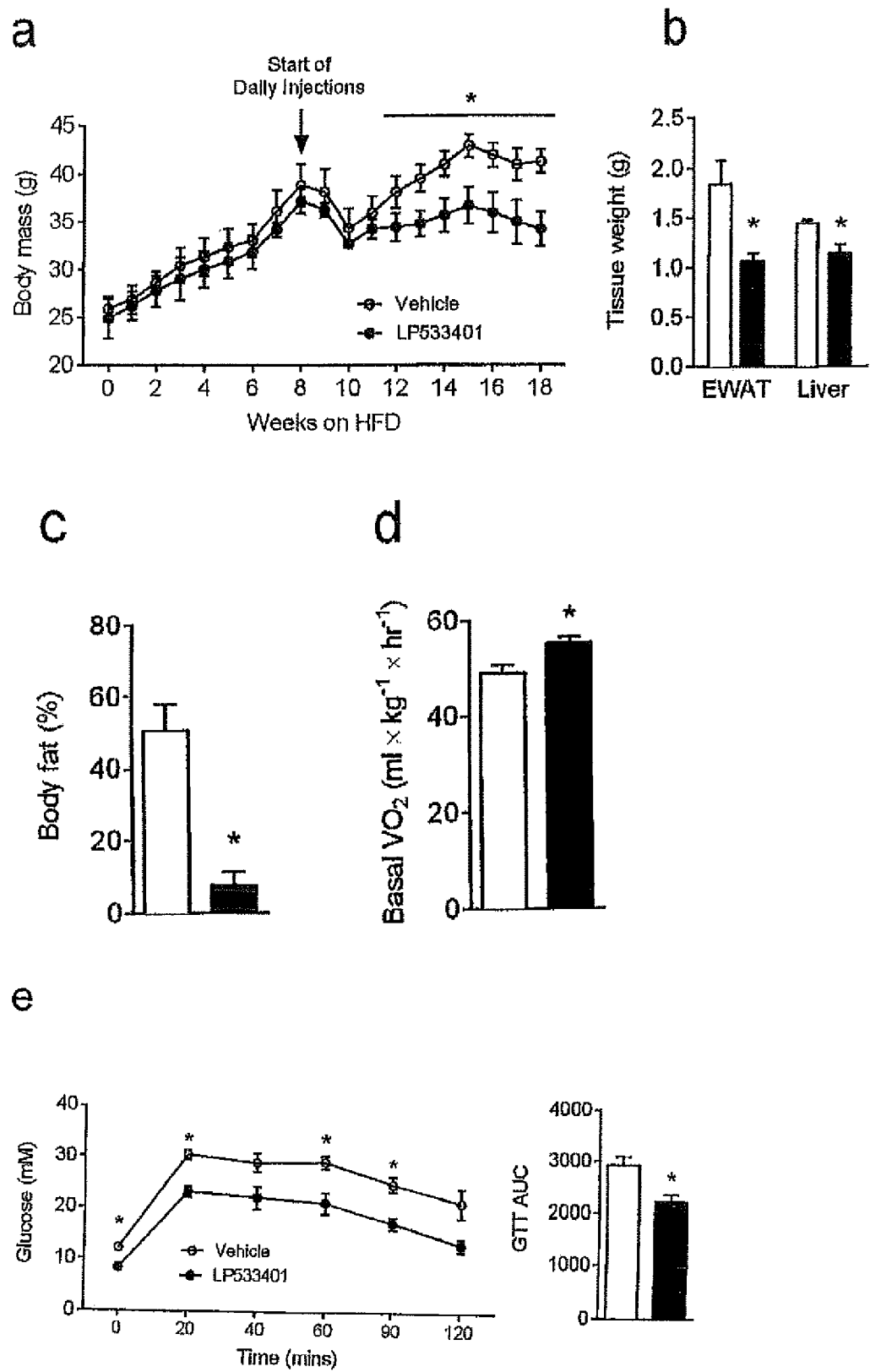
Figure 6:
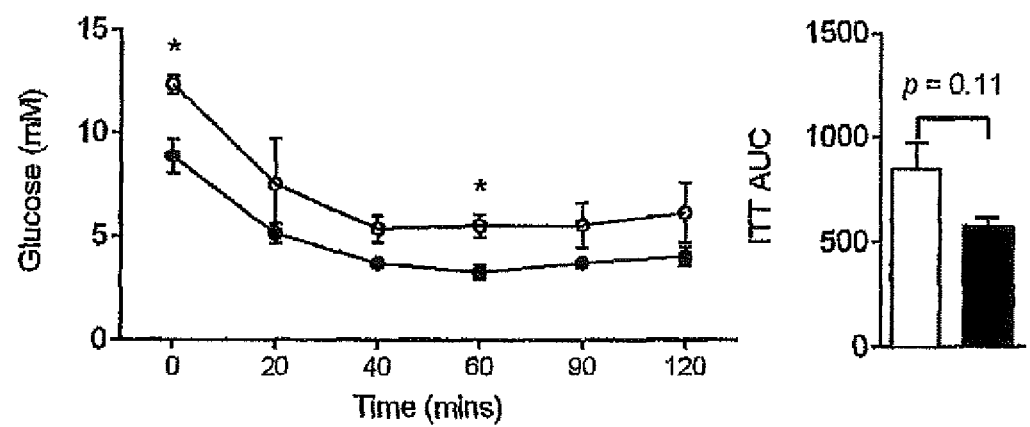
Figure 7:
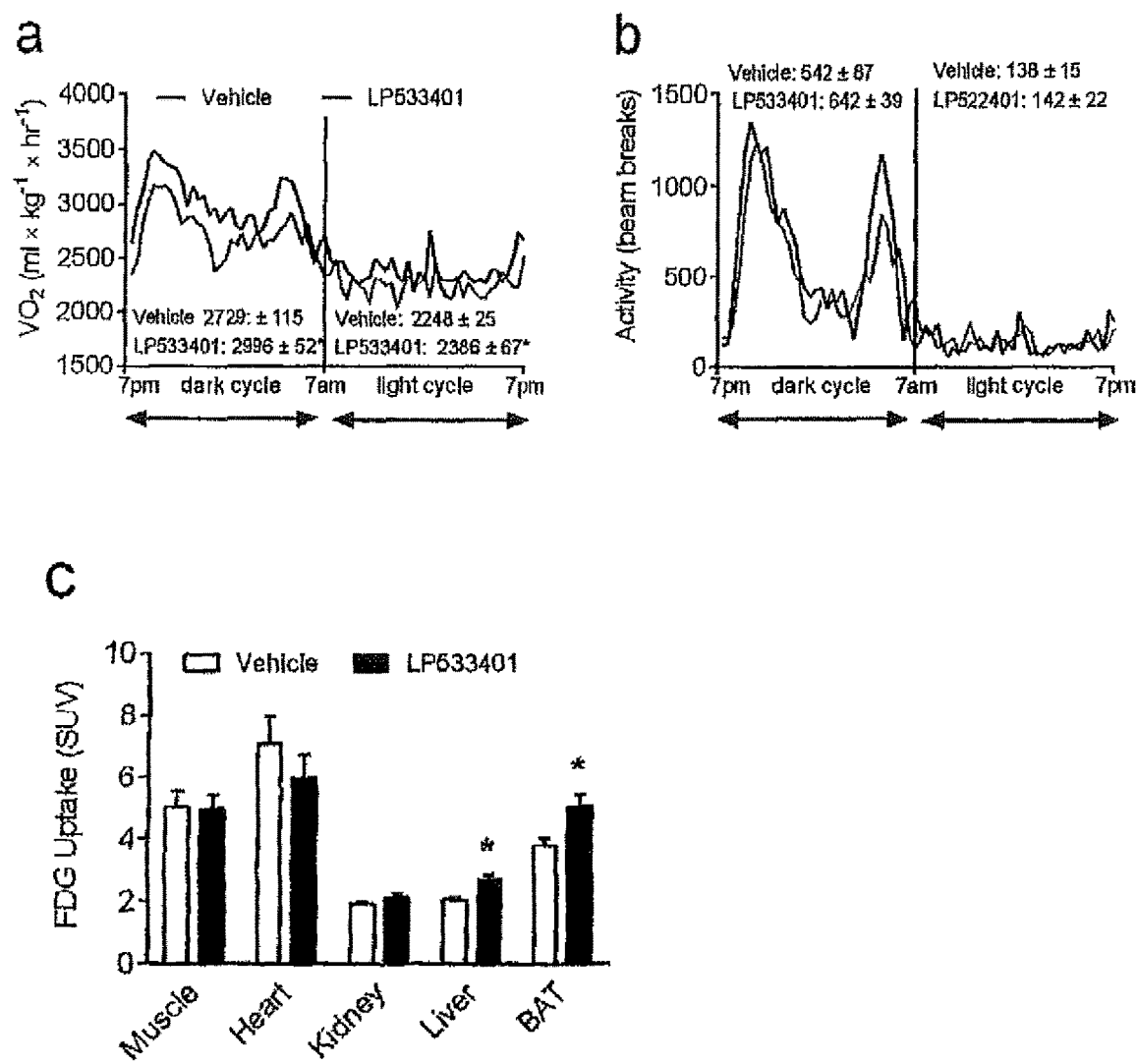
Figure 8:
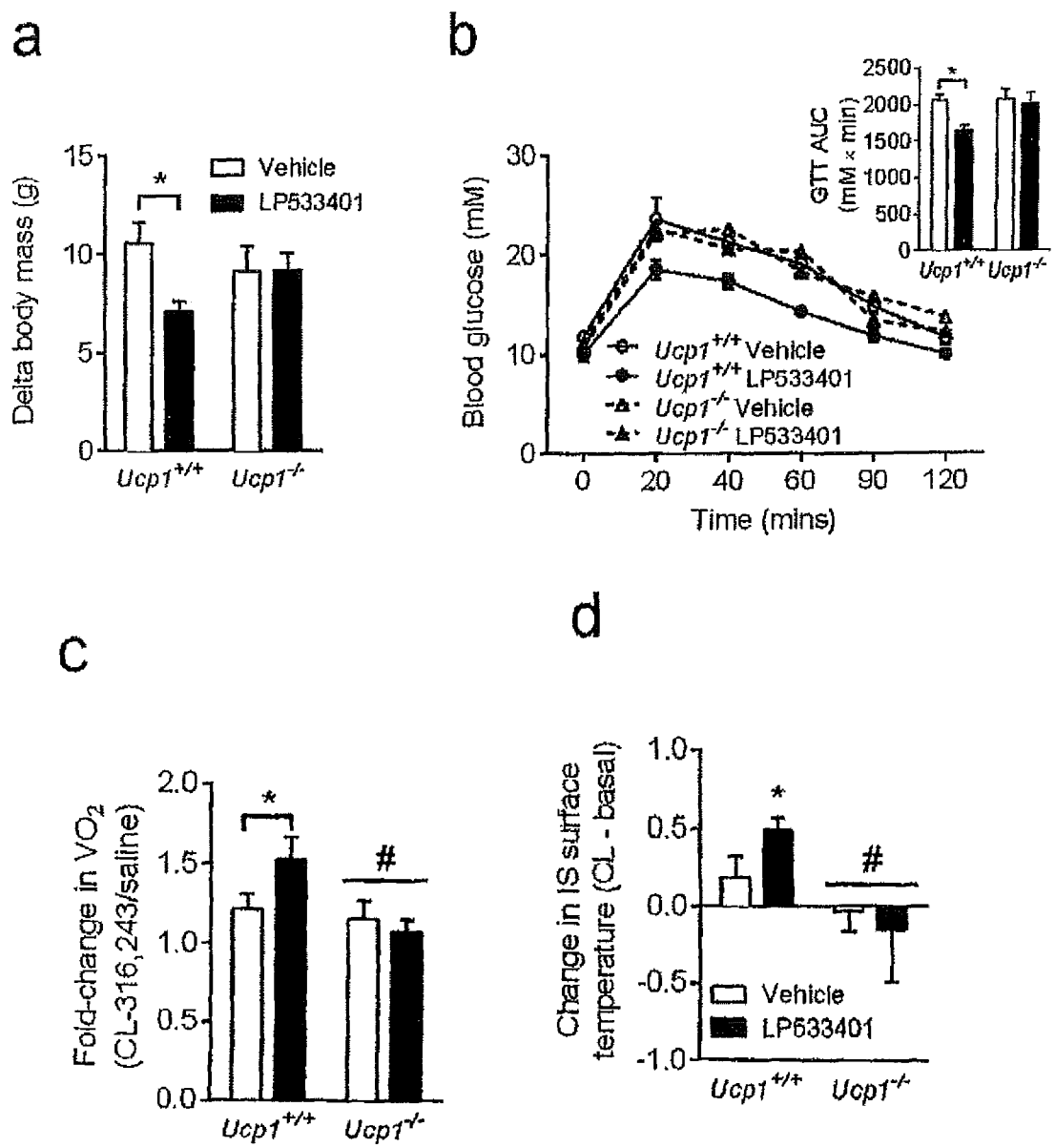
Figure 9:
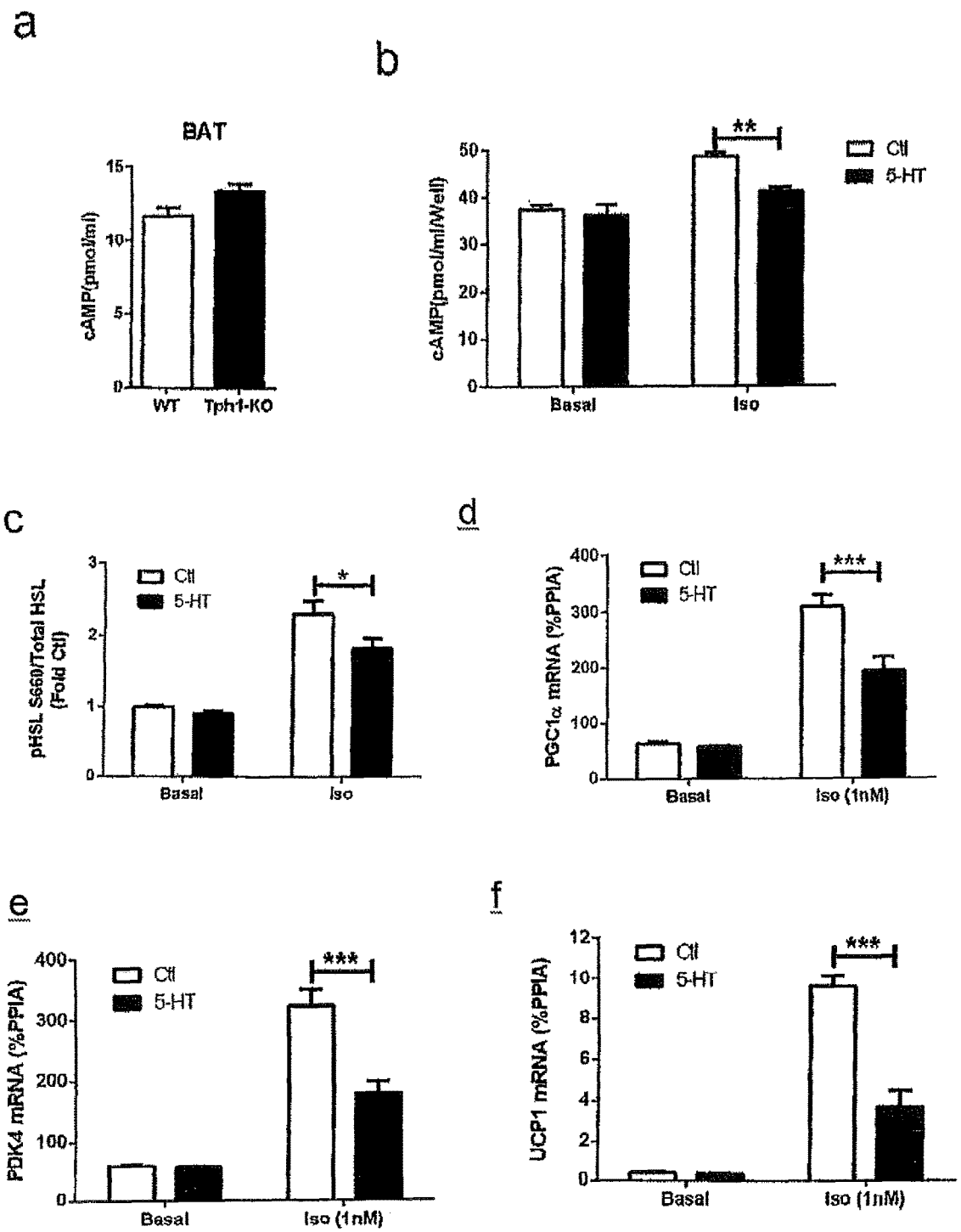
Figure 11:
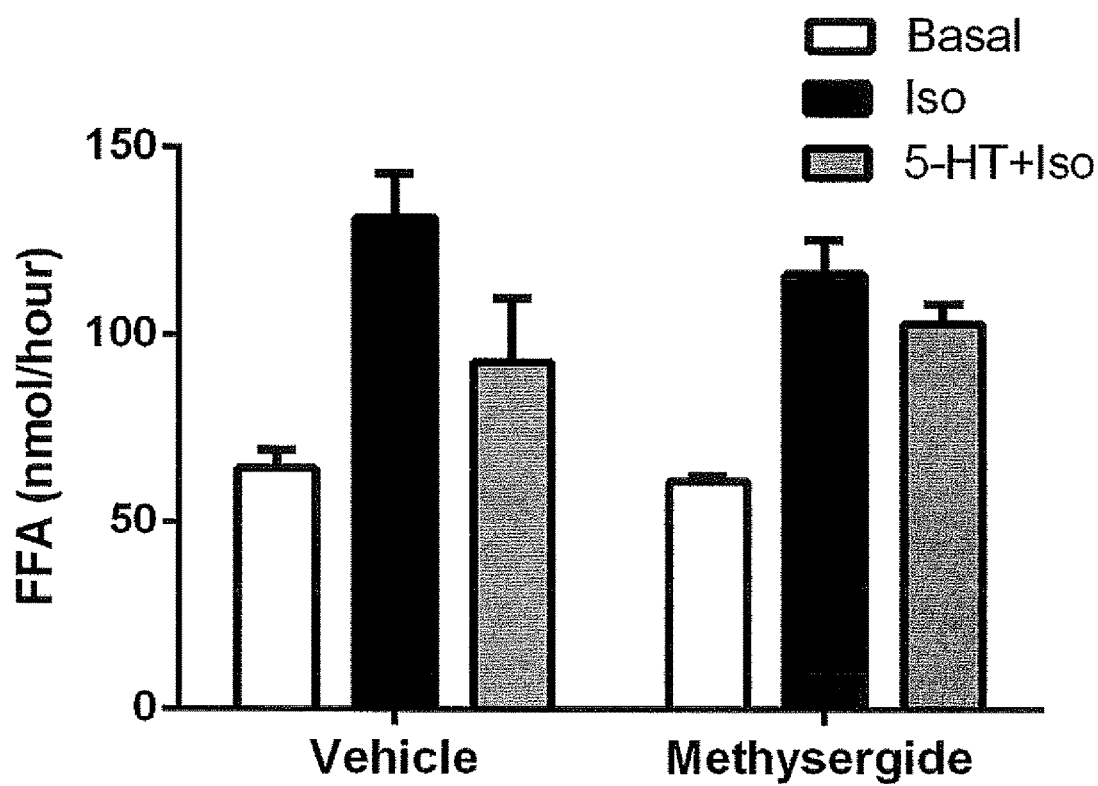
Figure 14:
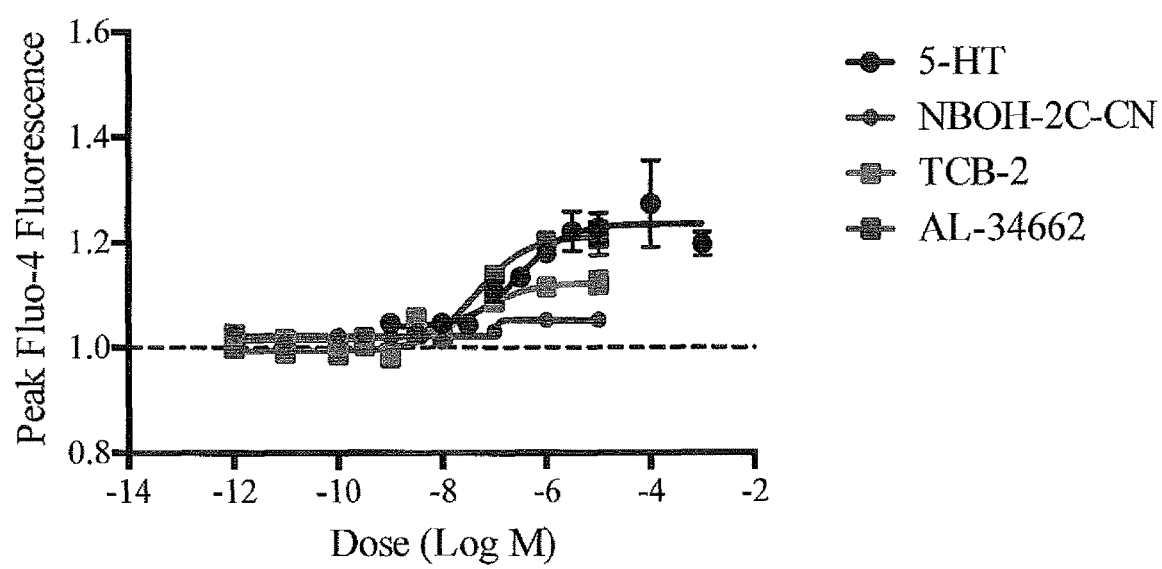
Figure 16:
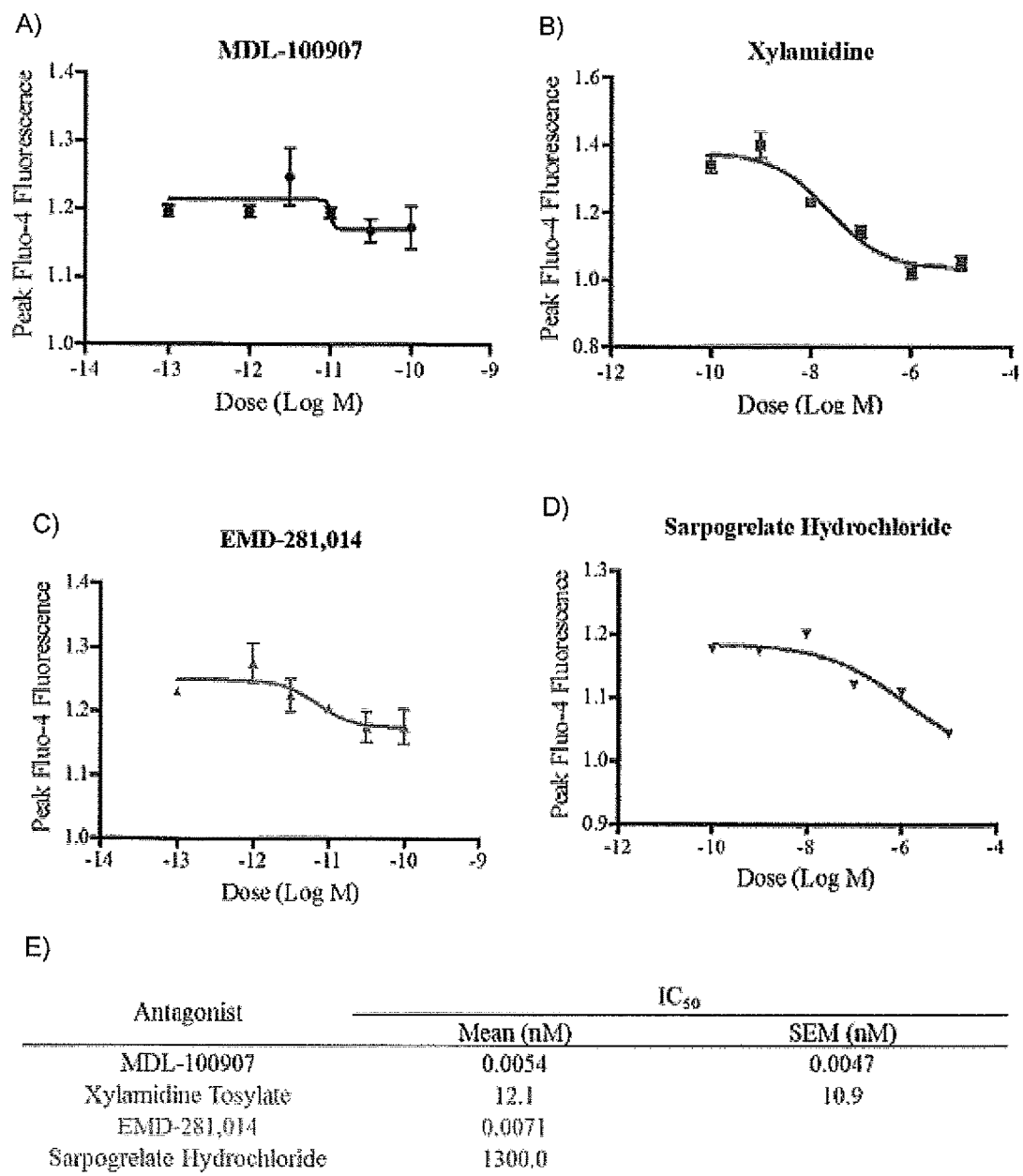
Figure 17:
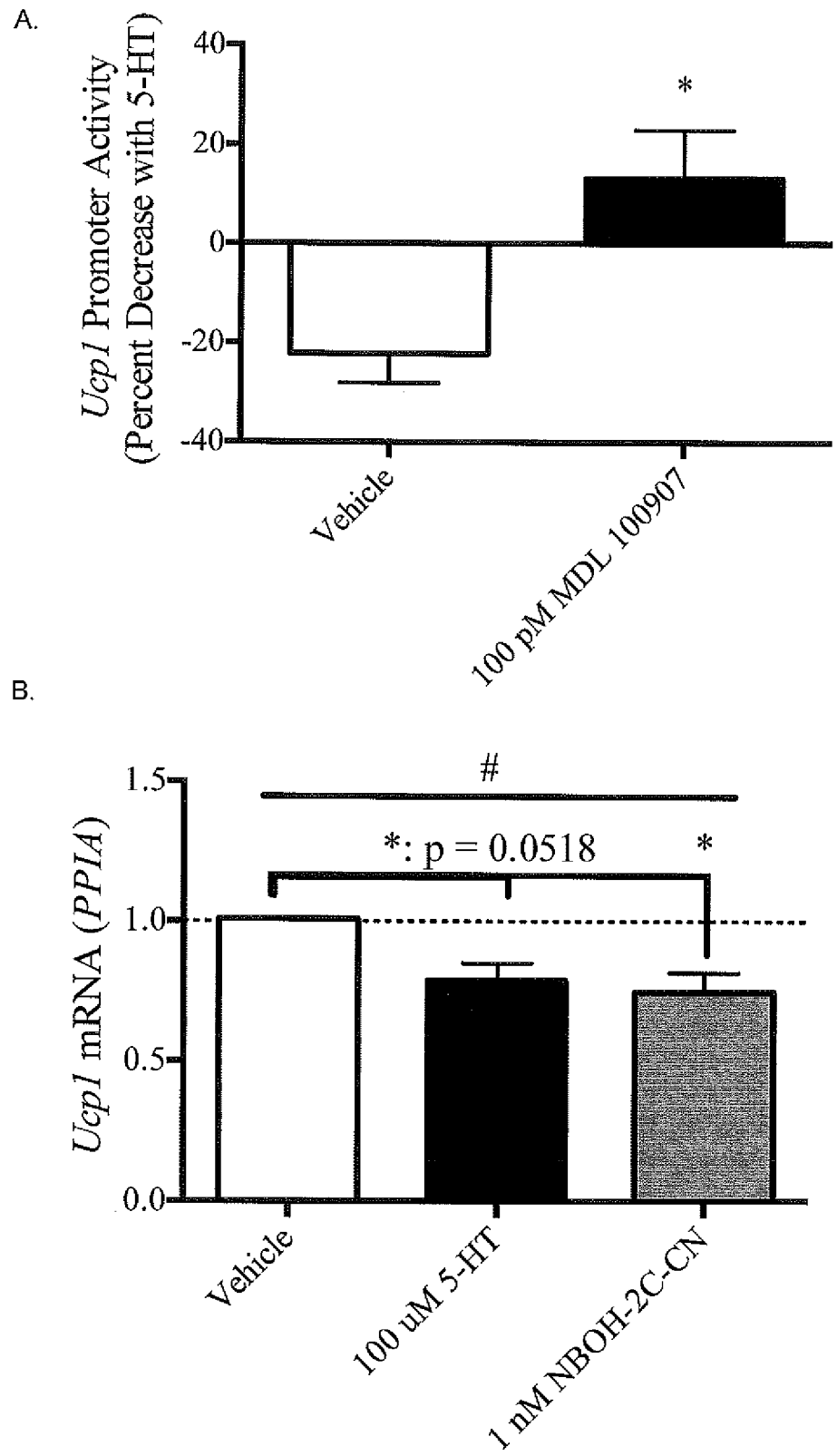
Figure 17:
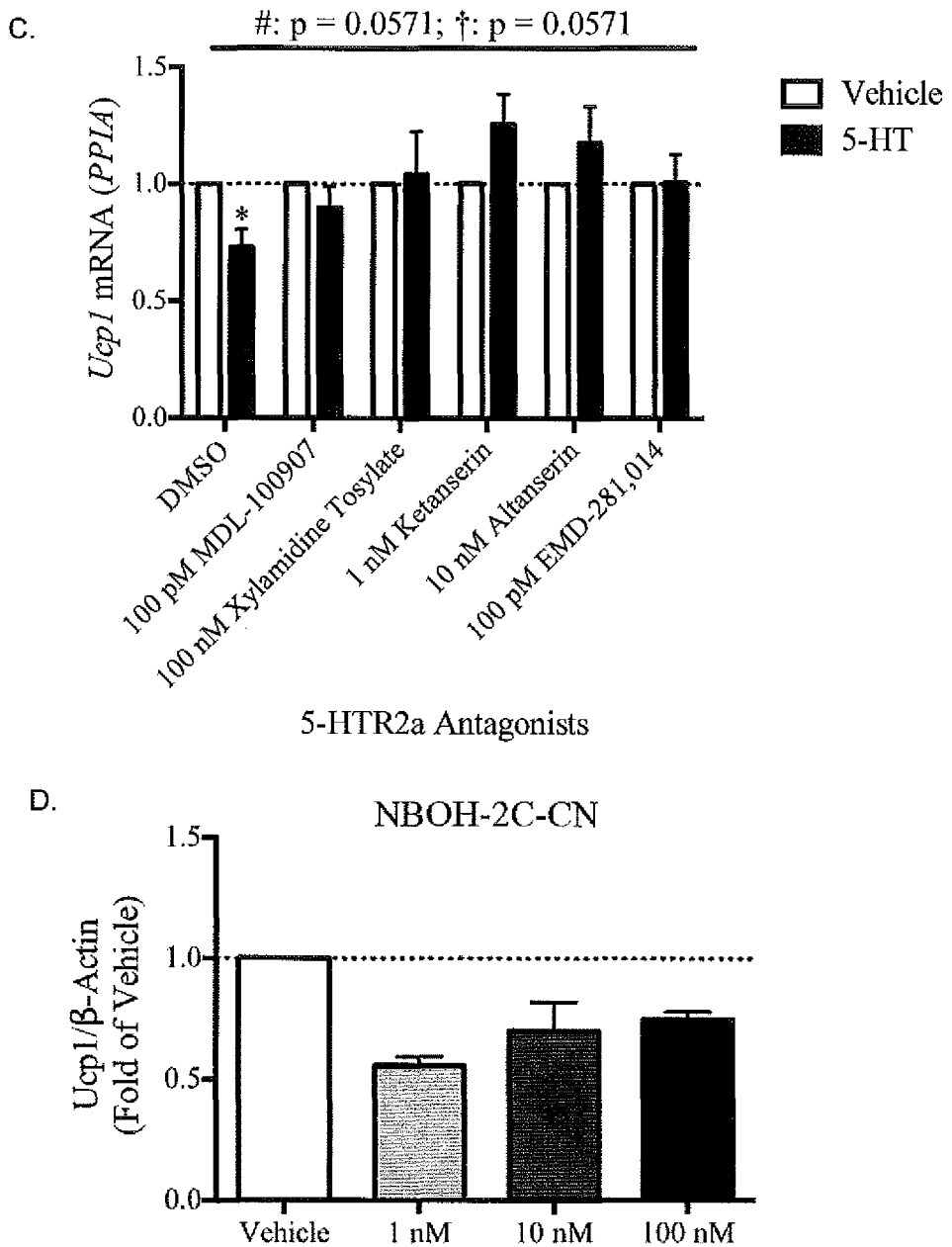
Figure 17:
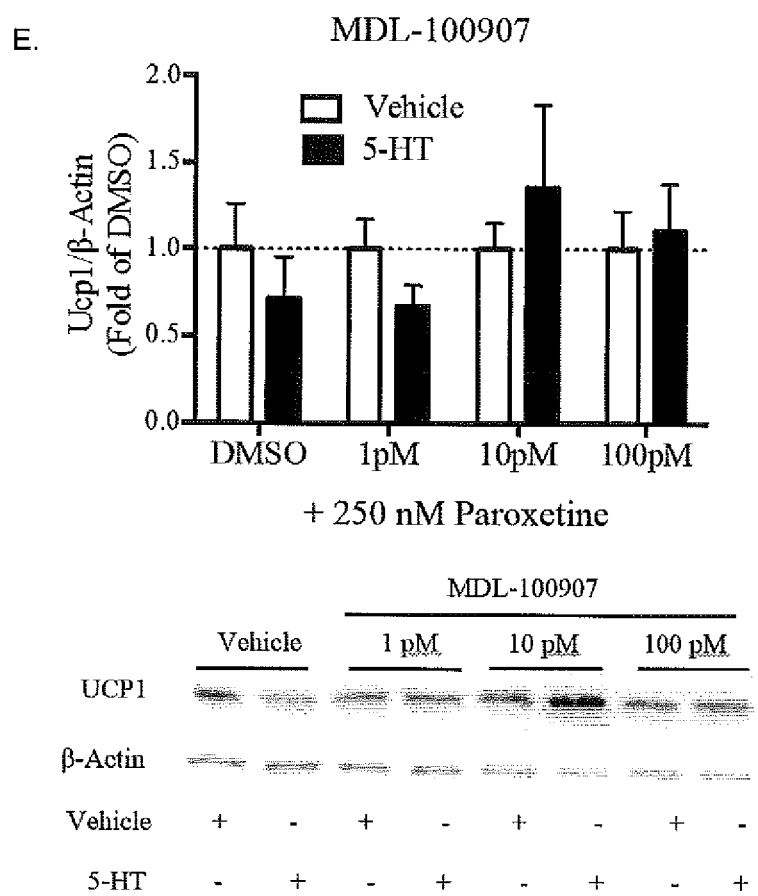
Figure 18:
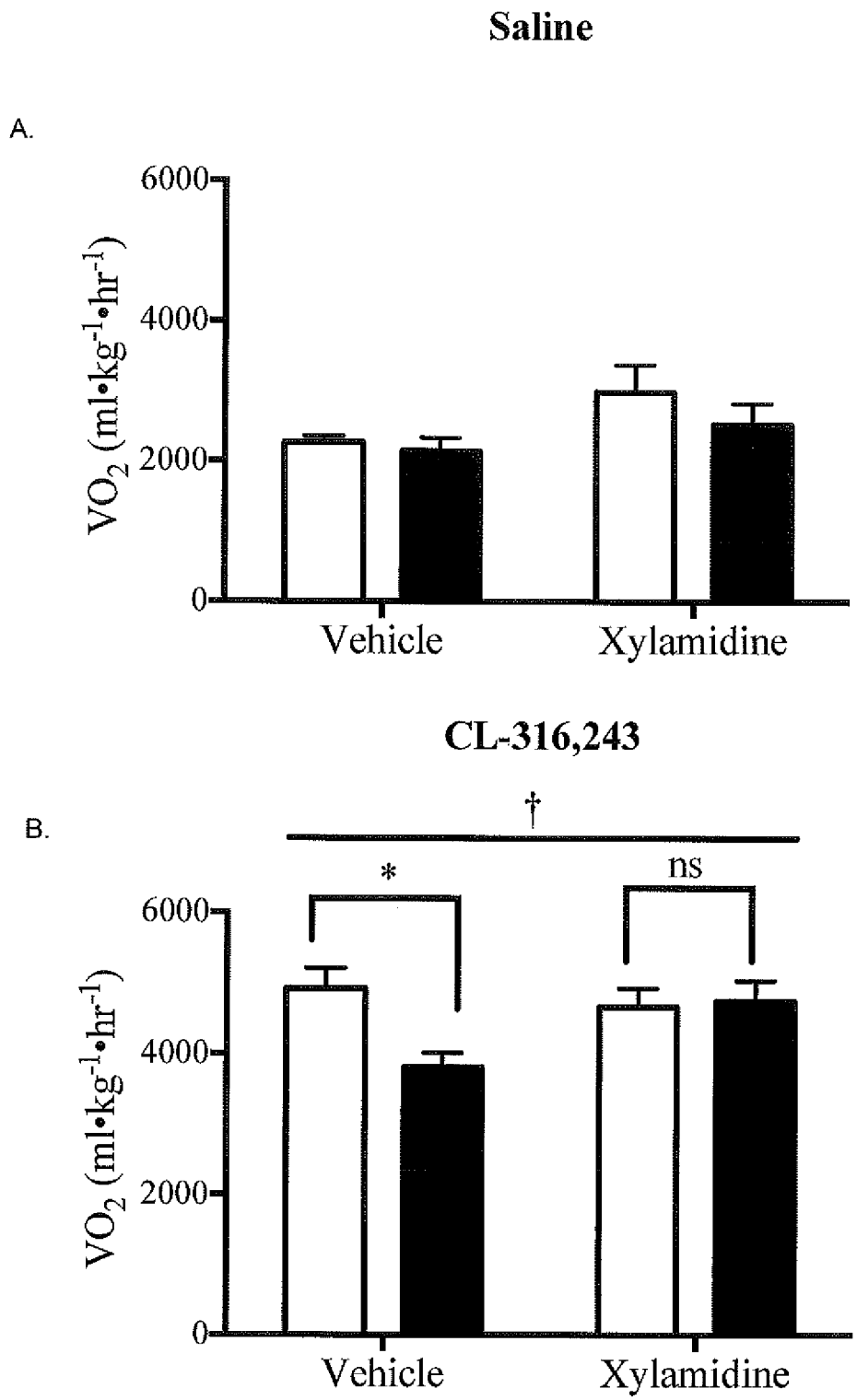
Figure 19:
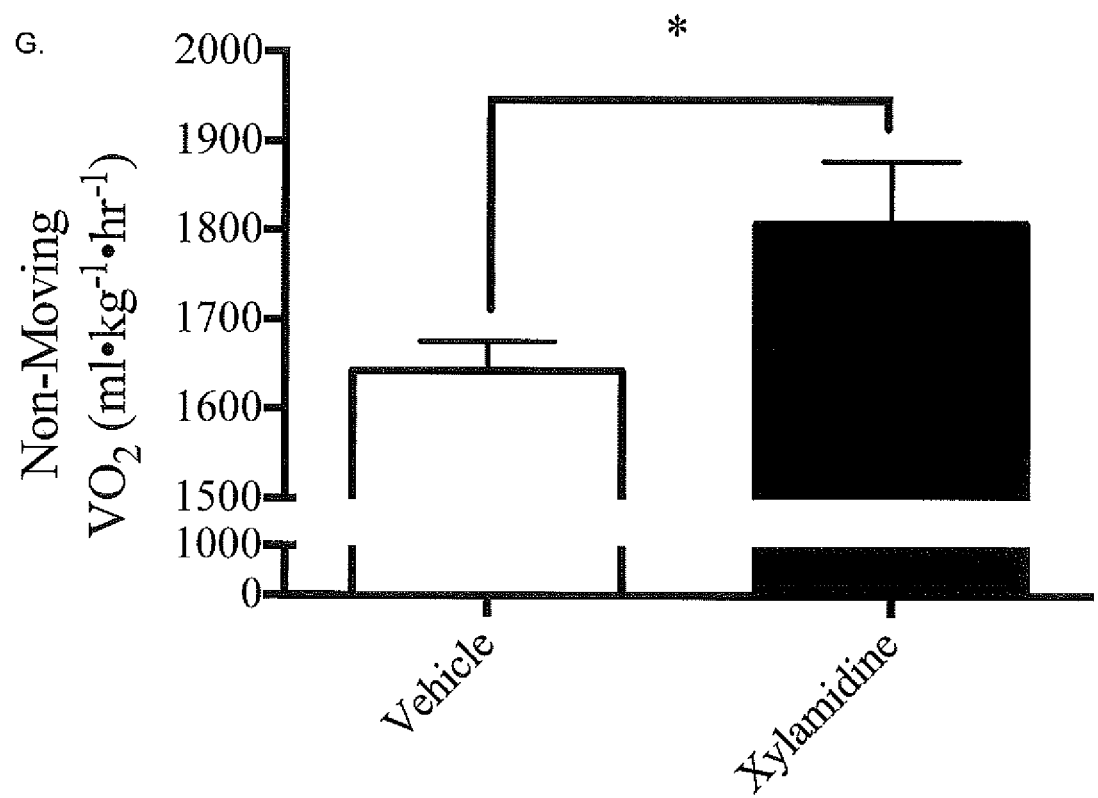
Figure 20:
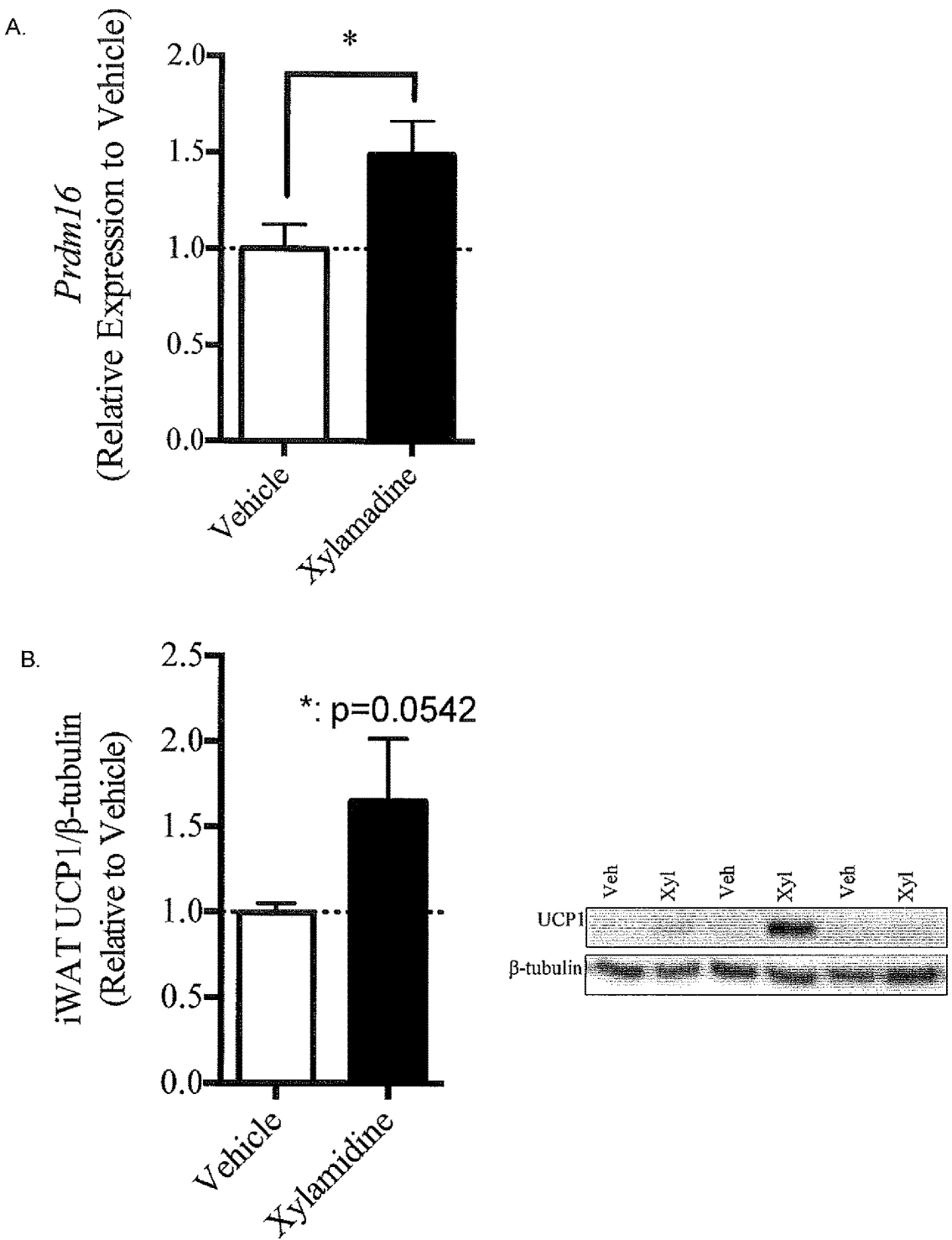
Figure 20:
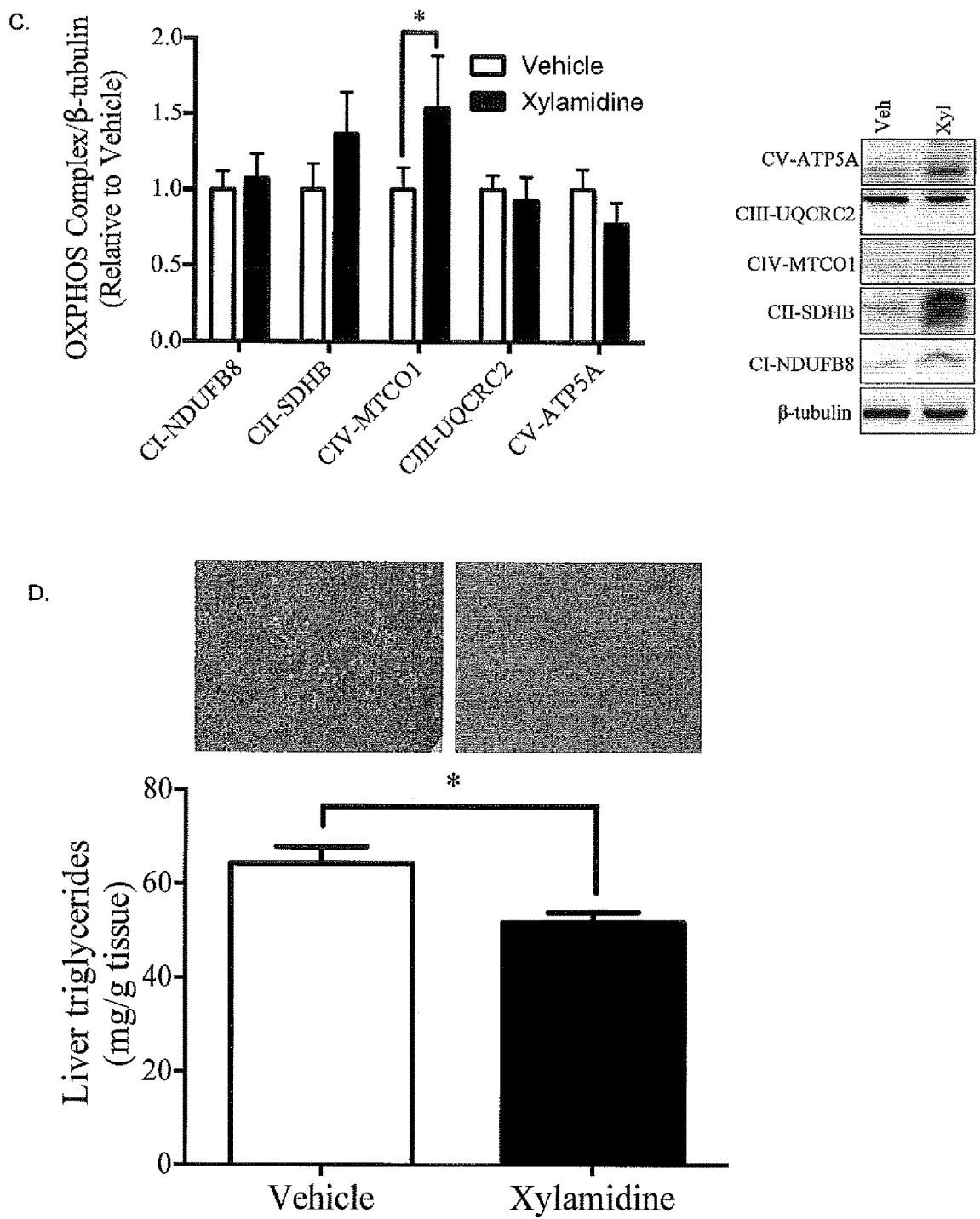
Figure 21:
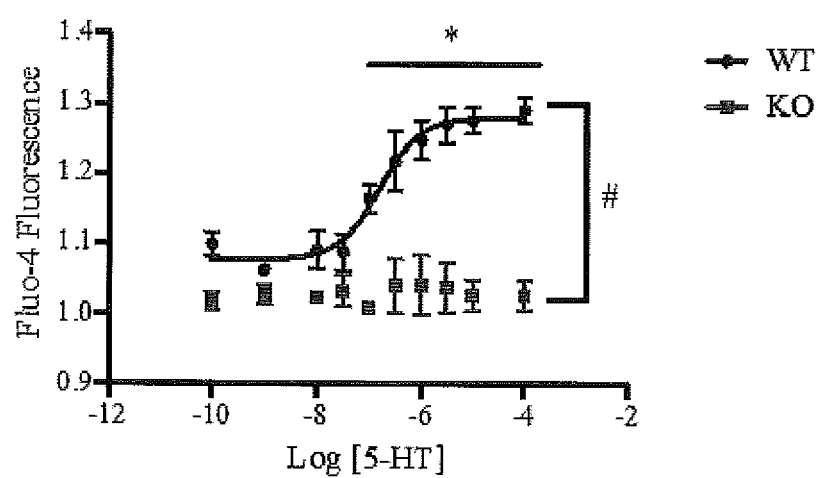
Figure 22:
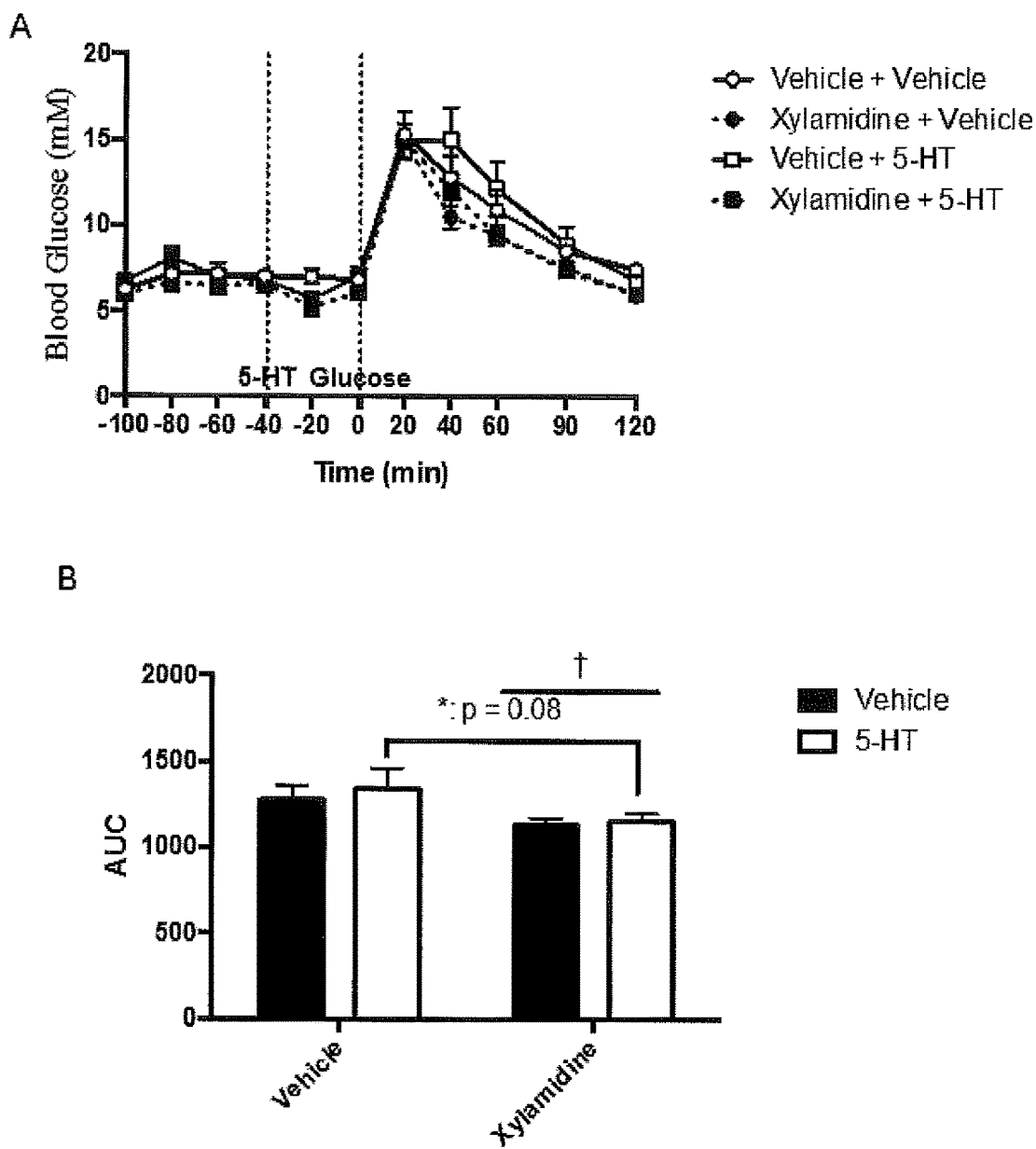
Figure 23:
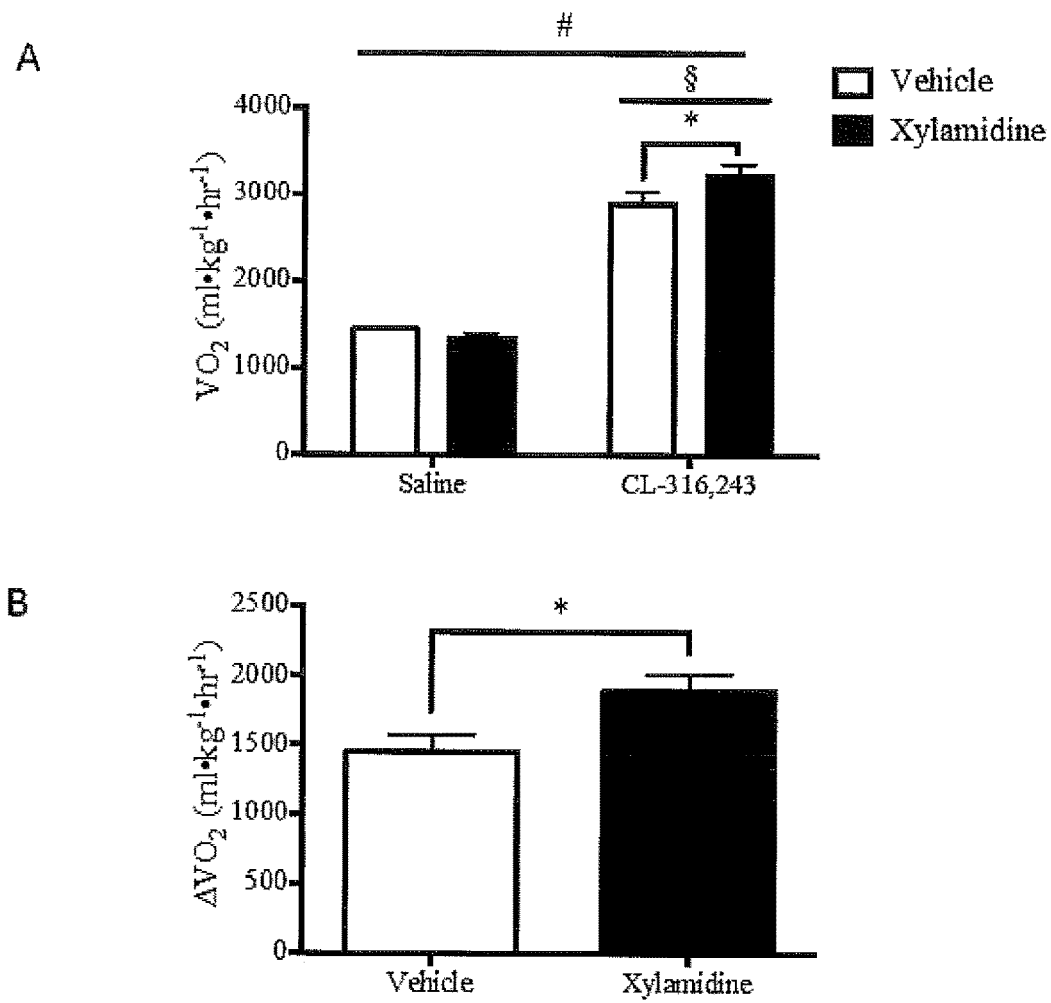
Figure 25:
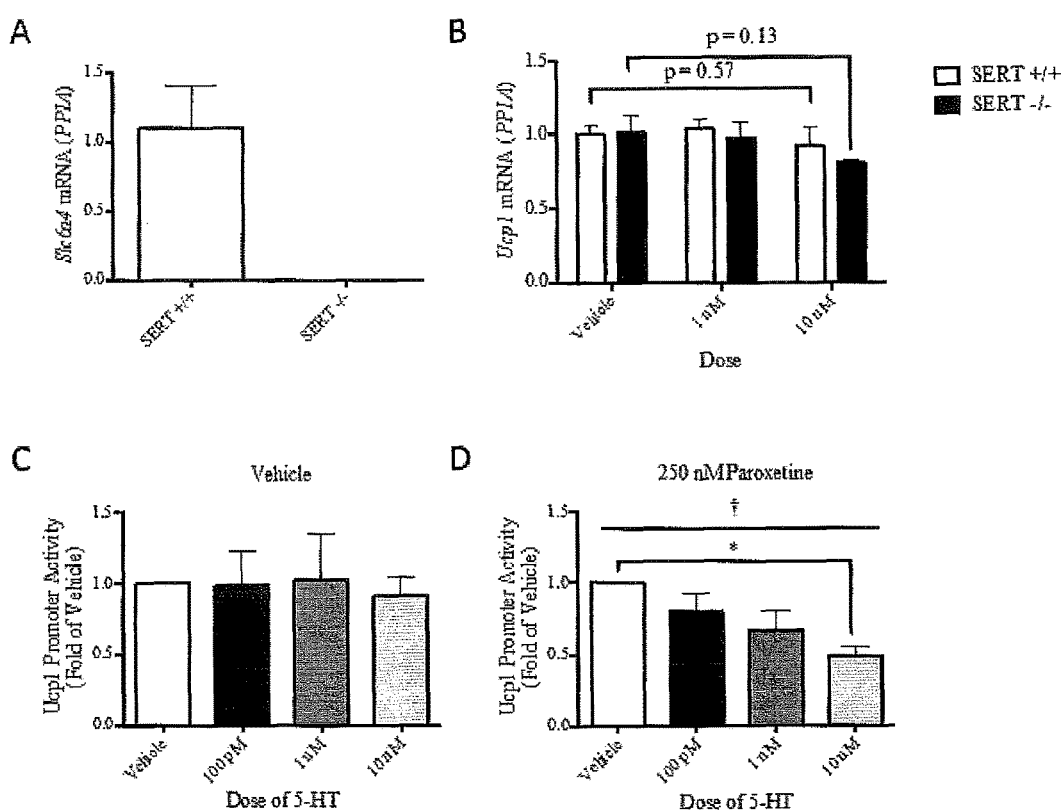

FIG. 6 shows reversal of obesity with chemical inhibition of Tph1 by comparison of body mass over time (a), EWAT and liver weights (b), % body fat (c), and basal oxygen consumption (d), glucose tolerance (e), and insulin sensitivity (f) of C57Bl6 mice fed a HFD for 8 wks before being treated with vehicle or Tph1 inhibitor for 10 wks. Data are mean±SEM. n=3-4. *P<0.05 versus vehicle;

FIG. 7 shows that Tph1 inhibition increases energy expenditure by enhancing brown adipose tissue activity graphically illustrated by a comparison of oxygen consumption (a), activity levels (b), and tissue FDG uptake (c) in vehicle or LP533401 treated mice. Data are mean±SEM. n=7-10. *P<0.05 versus vehicle;

FIG. 8 shows that UCP1 expression is required for the metabolic benefits of Tph1 inhibition with obesity by graphical comparison of: change in body mass after 6 weeks (a), glucose tolerance test (GTT) and AUC (b), and change in oxygen uptake (c) and dorsal interscapular surface temperature (d) when acutely injected with saline or CL-315,243, each of vehicle or LP533401 treatment in HFD-fed Ucp1$^{+/+}$ and Ucp1$^{-/-}$ mice. Data are mean±SEM, n=7-10. *P<0.05 relative to vehicle treated mice. $^{\#}$Indicates an overall effect of treatment (P<0.05). $^{†}$P<0.05 vs. saline condition;

FIG. 9 illustrates that serotonin inhibits increases in cAMP and the thermogenic program in brown adipocytes as shown by a comparison of cAMP (a) in BAT of HFD-fed Tph1$^{-/-}$ mice. Serotonin blunts isoproterenol-induced increases in cAMP (b) PKA substrates (c) and thermogenic program involving Pgc1a (d), Pdk4 (e) and Ucp1 (f). Data from mice are mean±SEM, n=7. Data from BAT cells are 3 independent experiments studied in duplicate. *P<0.05 relative to Tph1$^{+/+}$ mice. $^{†}$P<0.05 vs. vehicle treatment;

FIG. 10 graphically illustrates that the inhibition of Tph1 promotes increased metabolic activity and the "browning" of white adipocytes by (a) increased FDG uptake into eWAT of HFD-fed Tph1-/- mice or C57Bl6 mice treated with LP533401, increased expression of beige/brite cells in (b) eWAT and (c) iWAT of HFD-fed Tph1-/- mice. Data are mean±SEM, n=7-10. *P<0.05 relative to vehicle treated mice;

FIG. 11 illustrates the effect of serotonin receptor inhibition on cAMP-induced adipose tissue lipolysis;

FIG. 12 shows the amino acid (A) and nucleic acid-encoding sequence (B) of human Tph1;

FIG. 13 shows the amino acid (A) and nucleic acid-encoding sequence (B) of mouse Tph1;

FIG. 14 illustrates that 5-HT treatment causes a decrease in UCP1 protein in mouse brown adipocytes treated for 8 days with 5-HT and paroxetine (a selective serotonin reuptake inhibitor) at the indicated doses (A) and graphically illustrated (B), n=1-3 experiments performed in triplicate; the expression levels of transcripts for each 5-HT receptor in differentiated human brown and white adipocytes as assessed by RNA-Seq. n=5 (C); and representative dose responses of 5-HT2A agonists on peak Ca2+ signals in mouse brown adipocytes are graphically illustrated and summarized in a table of EC50 determined from 3 experiments performed in triplicate (D);

FIG. 15 illustrates the results of LINCS analysis to identify compounds that induce thermogenic genes;

FIG. 16 graphically illustrates that pre-treatment with 5-HT2A antagonists, MDL-100907 (A), Xylamidine (B), EMD-281,014 (C) and Sarpogrelate hydrochloride (D) attenuated 5-HT induced Ca2+ transients, and IC50 of each antagonist is summarized (E);

FIG. 17 graphically illustrates that 5-HT decreases Ucp1 promoter activity (A), Ucp1 mRNA (B/C), and UCP1 protein levels (E); a selective 5-HT2A agonist, NBOH-2C-CN, also inhibited Ucp1 mRNA levels (B) and chronic treatment with NBOH-2C-CN resulted in decreased UCP1 protein levels (D); antagonists of 5-HT2A blocked the 5-HT-induced reduction (A/C). and MDL-100907 dose-dependently attenuated the 5-HT induced decrease in UCP1 protein levels (E);

FIG. 18 demonstrates that 5-HT acutely inhibits BAT activity in vivo and can be rescued by xylamidine pretreatment. Mice housed at 30° C. were injected with xylamidine (3 mg/kg, −2 hour), 5-HT (5 mg/kg, −1 hour) and/or CL-316,243 (1 mg/kg, −20 min). VO2 under saline (inactive BAT-A) and CL-316,243 (active BAT-B) conditions. n=4. Interscapular surface temperature under saline (C) and CL-316,243 (D) conditions were quantified. n=6. $^{†}$ indicates interaction effect via 2-way ANOVA. * indicates significant difference from saline via bonferonni post-hoc test. In all graphs, bars represent mean and error bars represent S.E.M;

FIG. 19 demonstrates that chronic xylamidine administration attenuates high fat diet (HFD) induced glucose intolerance, and increases energy expenditure. (A) graphically shows growth curves of mice fed a 45% HFD starting at 7 weeks of age and at 9 weeks were administered vehicle (5% DMSO in ddH2O) or 3 mg/kg xylamidine tosylate daily via I.P. injection. n=8-11. (B) graphically depicts the fat content of mice from (A). (C) shows the time course of blood glucose levels following I.P. injection of 1.2 mg/kg glucose. n=23-25. (D) is an area under the curve calculation for blood glucose levels following I.P. injection of 1.2 mg/kg glucose; (E) graphically shows the oxygen consumption (VO2) of the mice; (F) graphically depicts the energy expenditure (heat) of the mice; and (G) graphically demonstrates the Oxygen consumption (VO2) of mice during periods of minimal movement. $^{†}$ indicates overall interaction, treatment and time effects via two-way ANOVA. Bars/points represent mean and error bars indicate S.E.M;

FIG. 20 demonstrates that chronic xylamidine treatment increases browning of subcutaneous adipose tissue and decreases liver triglycerides. (A) graphically depicts PR domain containing 16 (Prdm16) mRNA levels of inguinal (iWAT) adipose tissue from mice treated chronically with xylamidine. (B) graphically demonstrates UCP1 protein quantification in iWAT. (C) is a graphical quantification of representative proteins of each complex in the mitochondrial electron transport chain in iWAT, and (D) demonstrates liver triglyceride contents quantified via lipid extraction and enzymatic assay, with representative H&E stains of liver sections. n=8-11. * indicates significant difference from vehicle via t-test. Bars represent mean and error bars indicates S.E.M;

FIG. 21 graphically illustrates that calcium increases in response to 5-HT in brown adipocyte cells with HT2RA (WT) but do not in cells that lack the HT2RA gene (KO). n=2-4 individual experiments completed in triplicate. # indicates overall interaction effect of 2-Way ANOVA analysis and * indicates significant difference by Bonferonni post-hoc test. All bars are mean±S.E.M;

FIG. 22 illustrates (A) the time course of blood glucose levels prior to and following injections with xylamidine, 5-HT, and glucose, and (B) the area under the curve of the blood glucose levels from time 0-120 minutes. All symbols are mean±S.E.M. n=5-7. † indicates significant effect of xylamidine by 2-Way ANOVA. * indicates trend by Fisher LDS post-hoc comparison;

FIG. 23 graphically depicts that (A) xylamidine has no effect on energy expenditure when BAT is inactive (saline) but upon activation of BAT with CL-316,243, BAT is able to expend greater amounts of energy (# indicates interaction effect of 2-way ANOVA, § indicates effect of CL-316,243, * indicates significant effect by bonferonni post-hoc test), and (B) depicts that xylamidine increases the capacity of BAT to expend energy by quantifying the difference in energy expenditure between inactive and activated BAT for each mouse (* indicates significant effect by student's t-test. Bars are average values of 5 mice, error bars are S.E.M);

FIG. 24 demonstrates that upon treatment with xylamidine mice are resistant to obesity prior to any testing requiring fasting. (A) shows reduced weight gain in response to a HFD; and (B) shows reduced fat mass gain in response to a HFD. # indicates significant interaction effect between treatment and time by 2-way ANOVA. * indicates significant difference by Fisher LSD post-hoc test. N=22-24 All graphs depict mean±S.E.M;

FIG. 25 demonstrates that in brown adipocytes (BAs) that lack the serotonin transporter or have the transporter inhibited (i.e. treated with a paroxetine—an SSRI) there is greater sensitivity to inhibition by 5-HT. (A) confirms that these cells do not express the serotonin transporter (SERT, gene: Slc6a4). N=1 experiment performed in triplicate, (B) indicates that there is a greater and more significant decrease in Ucp1 mRNA in BAs without SERT. N=1 experiment performed in triplicate. P-values shown are from Fishers's LSD post-hoc analysis, and (C-D) indicate that treatment with an SSRI increases the sensitivity of BAs to inhibition of Ucp1 promoter activity by 5-HT. n=3 individual experiments completed in triplicate. † indicates overall effect of treatment by 1-way ANOVA, * indicates significant difference by Bonferonni post-hoc test. All bars are mean±S.E.M.

DETAILED DESCRIPTION OF THE INVENTION

A method of treating obesity and obesity-related disorders in a mammal is provided. The method comprises the step of administering to the mammal a compound that inhibits the synthesis or activity of peripheral serotonin, for example, peripheral serotonin that is associated with obesity.

The term "peripheral serotonin" is meant to encompass serotonin other than that in the central nervous system.

The term "peripheral serotonin that is associated with obesity" is meant to refer to peripheral serotonin that plays a role with respect to obesity in a mammal. It may be serotonin that is synthesized in the gastrointestinal tract, or synthesized elsewhere, however, it is generally serotonin that is not located within the gastrointestinal tract, and may be serotonin associated directly or indirectly with adipose tissue, i.e. which exists in adipose tissue or in cells that increase under obese conditions, e.g. immune cells such as mast cells, B cells, macrophages, and the like.

The term "obesity" refers to the condition in which a mammal accumulates excess body fat to the extent that it has a negative impact on health. Mammals that are considered "overweight" are included in this definition. Generally, mammals having a weight that exceeds the $85^{th}$ percentile are overweight, and those exceeding the $95^{th}$ percentile are obese. An adult human is considered to be overweight, if body mass index (BMI), a measurement obtained by dividing the individual's mass by the square of its height, exceeds 25 kg/m², and obese if BMI exceeds 30 kg/m².

The term "obesity-related disorders" includes disorders that are associated with obesity, including but not limited to, non-alcoholic fatty liver disease (NAFLD), low-grade chronic inflammation, polycystic ovarian syndrome (PCOS), insulin resistance, glucose intolerance, hyperglycemia, lipodystrophy, and metabolic syndrome. As one of skill in the art will appreciate, obesity and obesity-related disorders may lead to a myriad of other disease states or disorders, including cardiac disorders, endocrine disorders, respiratory disorders, hepatic disorders, reproductive disorders, and cancers.

The terms "treat" or "treating" as used herein with respect to obesity in mammals refers to the inhibition of peripheral serotonin to result in the reduction of at least one adverse effect of obesity, or prevention of obesity by preventing weight gain, and may include increasing one or more of metabolic activity, oxygen utilization, brown adipose activity and decreasing inflammation in comparison to basal levels. The term "mammal" refers to both human and non-human mammals.

In one aspect of the present invention, a method for treating obesity and related disorders comprises administration of a compound that inhibits the synthesis of peripheral serotonin, for example, a compound that inhibits tryptophan hydroxylase 1 (Tph1), which catalyzes the conversion of tryptophan into 5-hydroxytryptophan.

Inhibition of Tph1 may be achieved at the protein level, for example, using inhibitors designed to block Tph1 activity either directly or indirectly. Tph1 inhibitors may include, for example, synthetic small molecules, biological compounds or peptide mimetics based on such biological compounds. Suitable Tph1 inhibitors may or may not also inhibit Tph2. In this regard, it is noted that Tph1 inhibitors that do not cross the blood-brain barrier are suitable as the Tph1 target is peripheral. Thus, suitable Tph1 inhibitors need not significantly inhibit Tph2.

Examples of synthetic small molecule inhibitors of Tph1 useful in the present method are known in the art, for example, as described in WO 09/123978, WO 10/056992, WO 08/073933, WO 09/002964, WO 09/002970, WO 09/009561, WO 09/014972, WO 09/029499, WO 09/042733, WO 09/048864, WO 10/065333, WO 07/089335, U.S. Pat. No. 7,553,840, US 007/0191370, US 2008/0153852, US 2009/0005381, US 2009/0005382, US 2009/0029993, US 2009/0054308, US 2009/0062540, US 2009/0088447 and US 2009/0099206.

An example of a particular family of Tph1 inhibitors useful in the present method, including pharmaceutically acceptable salts, hydrates and solvates thereof, is represented by formula (1):

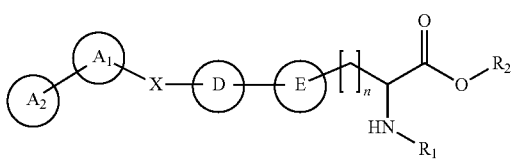

wherein each of $A_1$ and $A_2$ is independently a monocyclic optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3$R4)-, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; and n is 0-3.

$A_1$ and/or $A_2$ may be optionally substituted cycloalkyl (e.g., 6-membered and 5-membered), optionally substituted aryl (e.g., phenyl or naphthyl), or optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, $A_1$ and/or $A_2$ is aromatic. In others, $A_1$ and/or $A_2$ is not aromatic.

D may be optionally substituted aryl (e.g., phenyl or naphthyl), optionally substituted heterocycle (e.g., 6-membered and 5-membered), or optionally substituted bicyclic moiety (e.g., indole, iso-indole, pyrrolo-pyridine, or napthylene). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, D is aromatic. In others, D is not aromatic.

E may be optionally substituted aryl (e.g., phenyl or naphthyl), optionally substituted heterocycle (e.g., 6-membered and 5-membered as above), or optionally substituted bicyclic moiety (as above). In some compounds, E is aromatic. In others, E is not aromatic.

Particular compounds include those in which $R_1$ and $R_2$ is hydrogen or optionally substituted alkyl, or in which n is 1 or 2.

X may be a bond or S in some compounds, or may be —C($R_4$)=, =C($R_4$)—, —C($R_3R_4$)—, —C($R_4$)=C($R_4$)—, or —C≡C—, and, for example, $R_4$ may be independently hydrogen or optionally substituted alkyl. In other compounds, X may be —O—, —C($R_3R_4$)O—, or —OC($R_3R_4$)—, and, for example, $R_3$ may be hydrogen or optionally substituted alkyl, and $R_4$ may be hydrogen or optionally substituted alkyl. In one embodiment, $R_3$ is hydrogen and $R_4$ is trifluoromethyl. In other embodiments, X is —S($O_2$)—, —S($O_2$)N($R_5$)—, —N($R_5$)S($O_2$)—, —C($R_3R_4$)S($O_2$)—, or —S($O_2$)C($R_3R_4$)—, and, for example, $R_3$ is hydrogen or optionally substituted alkyl, $R_4$ is hydrogen or optionally substituted alkyl, and $R_5$ is hydrogen or optionally substituted alkyl. In another embodiment, X is —N($R_5$)—, —N($R_5$)C(O)N($R_5$)—, —C($R_3R_4$)N($R_5$)—, or —N($R_5$)C($R_3R_4$)—, and, for example, $R_3$ is hydrogen or optionally substituted alkyl, $R_4$ is hydrogen or optionally substituted alkyl, and each $R_5$ is independently hydrogen or optionally substituted alkyl.

The term "optionally substituted" as used herein indicates that a given moiety is substituted with an atom, chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)$NH_2$), amine (primary, secondary and tertiary such as alkylamino, arylamino, arylalkylamino), aroyl, aryl, aryloxy, azo, carbamoyl (—NHC(O)O-alkyl- or —OC(O)NH— alkyl), carbamyl (e.g., $CONH_2$, as well as CONE-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —$CCl_3$, —$CF_3$, —C($CF_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulthydryl, thioether) and urea (—NHCONH-alkyl-).

The term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl moieties having from 2 to 20 (e.g., 2 to 10 or 2 to 6) carbon atoms, and including at least one carbon-carbon double bond, and alkynyl moieties having from 2 to 20 (e.g., 2 to 20 or 2 to 6) carbon atoms, and including at least one carbon-carbon triple bond.

Preferred TPH1 inhibitors include LP-533401 ((2S)-2-amino-3-(4-(2-amino-6-(2,2,2-trifluoro-1-(3'-fluoro-[1,1'-biphenyl]-4-yl)ethoxy)pyrimidin-4-yl)phenyl)propanoic acid):

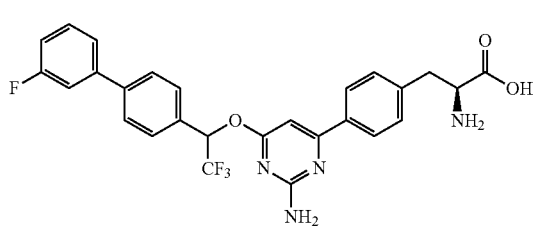

and LP-615819 (ethyl (2S)-2-amino-3-(4-(2-amino-6-(2,2,2-trifluoro-1-(3'-fluoro-[1,1'-biphenyl]-4-yl) ethoxy)pyrimidin-4-yl)phenyl)propanoate):

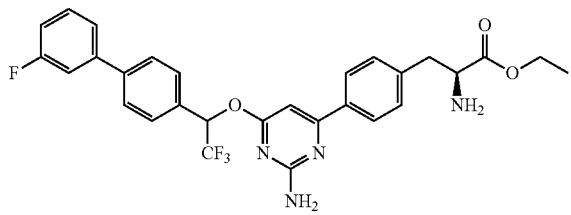 [SMILES: CCOC(=O)[C@@H](N)Cc1ccc(-c2cc(OC(c3ccc(-c4cccc(F)c4)cc3)C(F)(F)F)nc(N)n2)cc1]

Tph1 inhibitors may be readily synthesized using established methods of chemical synthesis, such as those described in U.S. Pat. No. 7,553,840. Some of these inhibitors are also commercially available. As one of skill in the art will appreciate, prodrugs of any of the foregoing compounds, or pharmaceutically acceptable salts, hydrates or solvates thereof, may also be employed. The term "pharmaceutically acceptable" refers to salts, hydrates and solvates that are non-toxic, and otherwise physiologically acceptable. The term "prodrug" refers to a compound (e.g. a drug precursor) that is transformed in vivo to yield the inhibitor or a pharmaceutically acceptable analogue, salt, hydrate or solvate thereof. The transformation may occur by various mechanisms (e.g., by metabolic or chemical processes), such as, for example, through hydrolysis in blood. The term "salt(s)", as employed herein, denotes both acidic salts formed with inorganic and/or organic acids, as well as basic salts formed with inorganic and/or organic bases. Examples of acid addition salts include those derived from nontoxic inorganic acids, such as hydrochloric, nitric, phosphoric, sulfuric, hydrobromic, hydroiodic, phosphorous and the like, as well as those from nontoxic organic acids such as aliphatic mono- and dicarboxylic acids, phenyl-substituted alkanoic acids, hydroxy alkanoic acids, aromatic acids, aliphatic and aromatic sulfonic acids and the like. Examples of base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like. A "solvate" is formed by admixture of the inhibitor in a solvent which is preferably pharmaceutically acceptable. A "hydrate" is a solvate formed when the solvent is water.

Examples of biological Tph1 inhibitors include immunological inhibitors such as polyclonal antibodies, or monoclonal antibodies prepared using well-established hybridoma technology developed by Kohler and Milstein (Nature 256, 495-497(1975)). Hybridoma cells can be screened immunochemically for production of antibodies specifically reactive with a selected region of the Tph1 protein and the monoclonal antibodies can be isolated. The term "antibody" as used herein is intended to include fragments thereof which also specifically react with a Tph1 protein according to the invention, as well as chimeric antibody derivatives, i.e., antibody molecules resulting from the combination of a variable non-human animal peptide region and a constant human peptide region. Examples of Tph1 antibodies include, for example, EP1311Y, PhosphoS260, ab46757, ab78969 and ab111872, which are commercially available (Abcam Inc.).

Peptide mimetic inhibitors of Tph1 may also be prepared, for example, based on known biological inhibitors, which inhibit Tph1 function. Such peptide mimeties may be designed to incorporate desirable features such as increased stability, e.g. resistant to biochemical degradation. Generally, such peptide mimetics are designed using techniques well-established in the art, including computer modeling, and prepared using standard methods of peptide synthesis.

In another embodiment, Tph1 gene expression may be inhibited using well-established methodologies utilizing polynucleotides, such as anti-sense, snp or siRNA technologies, which are derived from Tph1-encoding nucleic acid molecules. The term "Tph1-encoding nucleic acid molecule" refers to nucleic acid molecules (genes) encoding human Tph1, as well as non-human Tph1. Sequences of Tph1-encoding nucleic acid molecules are known in the art, and are available in sequence databases, such as GenBank, and the like. Examples of such sequences, including human and mouse sequences, are shown in FIG. 12B/13B, respectively. Tph1-encoding nucleic acid molecules may be used to prepare antisense oligonucleotides effective to bind to Tph1-encoding nucleic acid and inhibit the expression thereof. The term "antisense oligonucleotide" as used herein means a nucleotide sequence that is complementary to at least a portion of a target Tph1-encoding nucleic acid sequence. The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells) as well as the antisense binding region. In addition, two or more antisense oligonucleotides may be linked to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydrodyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates and phosphorodithioates. In addition, the antisense oligonucleotides may contain a combination of linkages, for example, phosphorothioate bonds may link only the four to six 3'-terminal bases, may link all the nucleotides or may link only 1 pair of bases.

The antisense oligonucleotides of the invention may also comprise nucleotide analogs that may be better suited as therapeutic or experimental reagents. An example of an oligonucleotide analogue is a peptide nucleic acid (PNA) in which the deoxribose (or ribose) phosphate backbone in the DNA (or RNA), is replaced with a polymide backbone which is similar to that found in peptides (P. E. Nielson, et al Science 1991, 254, 1497). PNA analogues have been shown to be resistant to degradation by enzymes and to have extended lives in vivo and in vitro. PNAs also form stronger bonds with a complementary DNA sequence due to the lack of charge repulsion between the PNA strand and the DNA strand. Other oligonucleotide analogues may contain nucleotides having polymer backbones, cyclic backbones, or acyclic backbones. For example, the nucleotides may have morpholino backbone structures (U.S. Pat. No. 5,034,506). Oligonucleotide analogues may also contain groups such as reporter groups, protective groups and groups for improving the pharmacokinetic properties of the oligonucleotide. Antisense oligonucleotides may also incorporate sugar mimetics as will be appreciated by one of skill in the art.

Antisense nucleic acid molecules may be constructed using chemical synthesis and enzymatic ligation reactions using procedures known in the art based on a given Tph1 nucleic acid sequence such as that provided herein. The antisense nucleic acid molecules of the invention, or fragments thereof, may be chemically synthesized using naturally occurring nucleotides or variously modified nucleotides designed to increase the biological stability of the molecules or to increase the physical stability of the duplex formed with mRNA or the native gene, e.g. phosphorothioate derivatives and acridine substituted nucleotides. The antisense sequences may also be produced biologically. In this case, an antisense encoding nucleic acid is incorporated within an expression vector that is then introduced into cells in the form of a recombinant plasmid, phagemid or attenuated virus in which antisense sequences are produced under the control of a high efficiency regulatory region, the activity of which may be determined by the cell type into which the vector is introduced.

In another embodiment, RNA interference technology may be utilized, including for example, siRNA, shRNA, miRNA, and the like, to inhibit expression of Tph1. Application of nucleic acid fragments such as siRNA and shRNA fragments that correspond with regions in a Tph1 gene and which selectively target a Tph1 gene may be used to block Tph1 expression. Such blocking occurs when the siRNA fragments bind to the gene thereby preventing translation of the gene to yield functional Tph1.

SiRNA, small interfering RNA molecules, corresponding to a region in a Tph1 gene are made using well-established methods of nucleic acid syntheses as outlined above with respect to antisense oligonucleotides. Since the structure of target Tph1 genes is known, fragments of RNA that correspond therewith can readily be made. The effectiveness of selected siRNA to block TPH1 expression can be confirmed using a TPH1-expressing cell line. Briefly, selected siRNA may be incubated with a TPH1-expressing cell line under appropriate growth conditions. Following a sufficient reaction time, i.e. for the siRNA to bind with mRNA encoding TPH-1 to result in decreased levels of free TPH1 mRNA, the reaction mixture is tested to determine if such a decrease has occurred. Suitable siRNA will prevent processing of the TPH1 gene to yield a functional protein. This can be detected by assaying for TPH1 activity in a cell-based assay, for example, to identify expression of a reporter gene that is regulated by TPH-1 binding, or by an enzyme activity assay on lysed cells using HPLC, or by measuring the amount of serotonin in/released from the cells.

It will be appreciated by one of skill in the art that siRNA fragments useful in the present method may be derived from specific regions of Tph1-encoding nucleic acid which may provide more effective inhibition of gene expression, for example, at the 5' end or the central region of the gene. In addition, as one of skill in the art will appreciate, useful siRNA fragments need not correspond exactly with a Tph1 target gene, but may incorporate sequence modifications, for example, addition, deletion or substitution of one or more of the nucleotide bases therein, provided that the modified siRNA retains the ability to bind selectively to the target gene. Selected siRNA fragments may additionally be modified in order to yield fragments that are more desirable for use. For example, siRNA fragments may be modified to attain increased stability in a manner similar to that described for antisense oligonucleotides.

Alternatively, a selected siRNA sequence may be modified to form a short hairpin RNA (shRNA) by introducing a short loop between the two strands. The resulting shRNA transcript may be inserted into and delivered using a vector, and is processed on delivery into a functional siRNA by the endoribonuclease Dicer in the usual fashion.

miRNAs resemble siRNA but are derived from regions of RNA transcripts that fold back on themselves to form short hairpins, whereas siRNAs derive from longer regions of double-stranded mRNA.

Inhibitory oligonucleotides in accordance with the invention may be any suitable size, including but not limited to, about 15 to about 100 consecutive nucleotides long; from about 15 to about 50 consecutive nucleotides; from about 18 to 30 consecutive nucleotides or about 19-25 nucleotides long. The length of such oligonucleotides is determined so that the oligonucleotide is capable of inhibiting expression of a target gene.

Once prepared, oligonucleotides determined to be useful to inhibit Tph1 gene expression, such as antisense oligonucleotides and siRNA, may be used in a therapeutic method to treat obesity and related disorders in a mammal. A suitable oligonucleotide may be introduced into tissues or cells of the mammal using techniques in the art including vectors (retroviral vectors, adenoviral vectors and DNA virus vectors) or by using physical techniques such as microinjection.

In another aspect of the invention, peripheral serotonin activity may be inhibited by blocking the peripheral serotonin receptor activity associated with obesity and/or adipose tissue, including serotonin receptors within adipose tissue, as well as serotonin receptors that are otherwise prevalent in obesity. For example, serotonin receptors which are highly enriched in adipose tissue include, but may not be limited to, 5-HT1a, 5-HT1b, 5-HT2a, 5-HT2b, 5-HT4 and 5-HT5a. Thus, inhibitors of serotonin receptors associated with obesity and/or adipose tissue may also be used to treat obesity in accordance with the invention. Examples of serotonin receptor inhibitors include, but are in no way limited to, cyanopindolol, alprenolol, methysergide, agomelatine, ketanserin, ritanserin, piboserod, latrepirdine, tropisetron and palonosetron.

In one embodiment, obesity in a mammal is treated using a compound that inhibits peripheral 5-HT2a activity. Examples of 5-HT2a antagonists or inverse agonists useful in this regard (i.e. useful to induce the thermogenic program) include but are not limited to, compounds such as volinanserin (MDL-100907), eplivanserin, glemanserin, ketanserin, pimavanserin, ritanserin xylamidine tosylate, altanserin, pruvanserin (EMD-281,014), pimozide, nortriptyline, clozapine, olanzapine, quetiapine, risperidone, asenapine, cyproheptadine, nefazodone, AMDA (9-aminomethyl-9,10-dihydro-anthracene), hydroxyzine (Atarax), 5-MeO-NBpBrT, niaprazine, naftidrofuryl, aripiprazole, AT 1015, DMT, DV 7028 hydrochloride, 4F 4PP oxalate, fananserin, melperone hydrochloride, mesulergine hydrochloride, paliperidone, PNU 96415E, R-96544 hydrochloride, spiperone hydrochloride, trazodone hydrochloride, ziprasidone hydrochloride, zotepine, methysergide, mirtazapine, pizotifen, LY-367,265, 2-alkyl-4-aryl-tetrahydro-pyrimido-azepines, AC-90179, nelotanserin and derivatives of any of these which retain peripheral 5-HT2a inhibitory activity. Compounds that inhibit downstream pathways of 5-HT2A may also be useful including, but not limited to, midostaurin and isoxicam. Preferred antagonists are those which selectively inhibit 5-HT2a.

As set out above, the 5-HT2a inhibitor may also be an oligonucleotide inhibitor such as an antisense oligonucleotide. Given the known sequences of mammalian 5-HT2a gene, as set provided by the NCBI (National Centre of Biotechnology Information), e.g. the sequence of the human 5-HT2a transcript variant 1 is provided under NCBI reference sequence NM_000621.4 2, the sequence of the human 5-HT2a transcript variant 2 is provided under NCBI reference sequence NM_001165947.2, and the sequence of the mouse 5-HT2a transcript is provided under NCBI reference sequence NM_172812, such oligonucleotide inhibitors can readily be identified using well-established methods in the art. The oligonucleotide inhibitor may also be an RNA-based inhibitor such as siRNA or shRNA which is derived from the mRNA transcript such that it base pairs with the transcript and prevents the translation thereof.

Nuclease gene editing systems may also be utilized to inactivate 5-HT2A. Examples of such systems include, but are not limited to, Clustered Regularly Interspaced Short Palindromic Repeats (CRISPR) nuclease system, e.g. including a targeting gRNA and a CRISPR-associated (Cas) gene, such as CRISPR-Cas9; Transcription Activator-Like Effector Nucleases (TALEN) and Zinc-Finger Nucleases (ZFN). In one embodiment, a CRISPR nuclease system, such as a CRISPR/Cas9 Type II genome editing system, may be used, which incorporates a Cas nuclease, and a guide RNA (gRNA) comprising trans-activating RNA (tracrRNA) and CRISPR RNA (crRNA) which is recognized by the Cas nuclease. The crRNA includes a distinctive array of non-coding direct RNA repeats, and a targeting RNA sequence that is homologous to a region on the Htr2a target gene to be silenced. The targeting RNA may comprise about 10-30 nucleotides and may comprise a GC content of about 40-80%. The CRISPR system may be utilized to silence or disrupt expression of Htr2a by insertion or deletion of nucleotides to disrupt its Open Reading Frame (ORF), or to introduce a premature stop codon therein.

Antibody inhibitors of 5-HT2a may also be utilized, and these may be prepared as described above, or may be commercially available, e.g. from Abeam, Novus Biologicals, Lifespan Biosciences, etc.

A therapeutic inhibitor of peripheral serotonin may be administered to a mammal in the treatment of obesity and related disorders, either alone or in combination with a suitable pharmaceutically acceptable carrier. The expression "pharmaceutically acceptable" means acceptable for use in the pharmaceutical and veterinary arts, i.e. not being unacceptably toxic or otherwise unsuitable. Examples of pharmaceutically acceptable carriers include diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the type of inhibitor and the intended mode of administration of the composition. In one embodiment of the invention, the compounds are formulated for administration by infusion, or by injection either subcutaneously, intravenously, intrathecally, intraspinally or as part of an artificial matrix, and are accordingly utilized as aqueous solutions in sterile and pyrogen-free form and optionally buffered or made isotonic. Thus, a selected compound may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, anti-oxidants, preservatives, colouring agents and flavouring agents may also be present. In another embodiment, the composition may be formulated for application topically or transdermally as a cream, lotion or ointment. For such topical/transdermal applications, the composition may include an appropriate base such as a triglyceride base, and/or a carrier that facilitates absorption through the skin. Such creams, lotions and ointments may also contain a surface active agent and other cosmetic additives such as skin softeners and the like as well as fragrance. Aerosol formulations, for example, for nasal delivery, may also be prepared in which suitable propellant adjuvants are used. Compositions of the present invention may also be administered as a bolus, electuary, or paste. Other adjuvants may also be added to the composition regardless of how it is to be administered, for example, anti-microbial agents may be added to the composition to prevent microbial growth over prolonged storage periods.

In accordance with the present invention, a selected peripheral serotonin inhibitor is administered to a mammal in the treatment of obesity such that it targets peripheral serotonin/serotonin receptors associated with obesity, for example, serotonin and/or serotonin receptors associated with adipose tissue, or associated with cells and tissue that play a role in obesity, e.g. immune cells. Accordingly, the inhibitor is administered via an appropriate administrable route to reach the target peripheral serotonin. Appropriate routes of administration include systemic administration, or a route which results in localized administration, e.g. injection, topical or transdermal, and the like. Other routes of administration, such as oral administration, may also be adapted to achieve the desired targeted approach by the use of carriers that target peripheral serotonin associated with obesity.

The use of a peripheral serotonin inhibitor, in accordance with the invention, targeted at peripheral serotonin associated with obesity in the treatment of obesity, may be utilized in conjunction with other therapeutic agents or treatments to enhance the treatment of obesity. For example, the inhibitor may be utilized in conjunction with conventional therapy for obesity, such as lifestyle interventions involving changes in diet and physical activity levels. Use of a peripheral serotonin inhibitor to treat obesity may also be utilized in combination with herbal remedies that elicit weight loss, or in conjunction with weight loss therapies including glucagon-like peptide agonists (i.e. exenatide, liraglutide), 5-HT$_{2C}$ agonist (i.e. Lorcaserin), growth differentiating factor-15 (GDF15) analogues, cold or β-adrenergic activators of BAT (i.e. Mirabegron), fibroblast growth factor-21 (FGF21) analogues, or inhibitors to sodium glucose transporters ($SGLT_2$). It may also be used in conjunction with or prior to surgical treatments for obesity, e.g. bariatric surgery for weight loss.

In another embodiment, use of a peripheral serotonin inhibitor in accordance with the invention, may be used in conjunction with treatments that may increase peripheral circulating serotonin, thereby inducing weight gain, e.g. drug-induced weight gain or obesity. Such medical treatments may include, for example, SSRI/anti-depressant treatments, atypical antipsychotics, and mood stabilizers such as lithium.

To treat obesity in accordance with the present method, a therapeutically effective amount of peripheral serotonin inhibition is attained by methods such as those described. The term "therapeutically effective" with respect to peripheral serotonin inhibition is meant to refer to a level of inhibition that functions to increase brown and beige adipose tissue metabolic activity by at least about 5% as measured by infrared thermography, thermal temperature sensors, positron emission tomography imaging, or magnetic resonance imaging (including an increase in UCP1, PRDM16, OXPHOS enzymes, etc.), or a level of inhibition that increases oxygen utilization by at least about 5% as determined by measuring basal metabolic rate or β-adrenergic agonist-induced metabolic rate, or a level of inhibition that results in a decrease in serum levels of inflammation markers such as Tnf-alpha, IL6 and C-reactive protein (CRP), a decrease in serum level of the adipokine or leptin of at least about 5%, an increase in serum level of at least about 5% of adiponectin, or a decrease of a least about 5% in blood glucose, glycated hemoglobin, serum insulin or c-peptide.

The dosage of peripheral serotonin inhibitor that would be sufficient to achieve therapeutically effective peripheral serotonin inhibition can readily be determined using appropriately controlled clinical trials, as one of skill in the art would appreciate. For synthetic small molecule inhibitors of TPH1, suitable dosages may also be determined based on current knowledge of these inhibitors. For example, it is expected that the therapeutically effective dosage of a TPH1 inhibitor such as LP533401, would be in the range of about 0.1 to 1000 mg/kg, preferably a range of about 0.5-500 mg/kg, and more preferably a range of about 1-250 mg/kg. Likewise, dosages of serotonin receptor inhibitors may be determined based on the knowledge of such inhibitors. It is expected that the therapeutically effective dosages of a serotonin receptor inhibitors may also be in the range of about 0.1 to 1000 mg/kg.

In one embodiment, in the present treatment of obesity, the peripheral serotonin inhibitor is administered to mammals on a high fat or high caloric diet, or mammals deficient in leptin.

In another embodiment of the present invention, the peripheral serotonin inhibitor is administered topically to a mammal in need of treatment at an adipose tissue site on the mammal.

In a further aspect of the present invention, a method of treating a mammal that is underweight or undesirable weight loss in a mammal is provided. A mammal that is underweight, or is experiencing undesirable weight loss, has lost or is losing weight to an extent that is associated with a decline in health. Such weight loss may result from disease such as a cancer or other chronic/acute disease, and is known as cachexia. The present method of treatment comprises administering to the mammal a compound or entity that increases the activity of peripheral 5-HT2a. In one embodiment, the compound is a 5-HT2a agonist. Examples of suitable agonists include, but are not limited to, TCB-2, AL-34662, NBOH-2C-CN, DOI, PNU 22394, 25I-NBOH, 25I-NBOMe, Mexamine, O-4310, PHA-57378, 25C-NBOMe, Bromo-DragonFLY, OSU-6162, Juncosamine, Efavirenz, Mefloquine and Lisuride.

As will be appreciated by one of skill in the art, the 5-HT2a agonist may be administered to a mammal in combination with one or more pharmaceutically acceptable carriers, generally selected based on the route for administering the 5-HT2a agonist. Examples of suitable carriers are described herein with respect to the administration of 5-HT2a antagonists. The administrable route may be any route suitable to target peripheral 5-HT2a. Appropriate routes of administration include systemic administration, or a route which results in localized administration, e.g. injection, topical or transdermal, and the like. Oral routes of administration may also be suitable.

To treat weight loss, a therapeutically effective amount of a 5-HT2a agonist is administered to a mammal in need of treatment, i.e. an amount that functions to decrease brown and beige adipose tissue metabolic activity by at least about 5% as measured by infrared thermography, thermal temperature sensors, positron emission tomography imaging, or magnetic resonance imaging, or an amount that reduces oxygen utilization by at least about 5% as determined by measuring basal metabolic rate or β-adrenergic agonist-induced metabolic rate. The dosage of a peripheral serotonin agonist useful to treat weight loss in a mammal can readily be determined using appropriately controlled clinical trials, as one of skill in the art would appreciate. For synthetic small molecule agonists, suitable dosages may also be determined based on current knowledge of these inhibitors. It is expected that the therapeutically effective dosage of a selected 5-HT2a agonist be in the range of about 0.1 to 1000 mg/kg.

Embodiments of the invention are described in the following specific examples which are not to be construed as limiting.

Example 1

Effect of Tph1 Inhibition on Obesity

Animals. All experiments were approved by the McMaster University animal ethics committee and conducted under the Canadian guidelines for animal research. $Tph1^{-/-}$ mice on C57BL/6 background were originally produced by gene mutation as described by Côté et al. (*Proc Natl Acad Sci USA* 100, 13525-13530 (2003)). Heterozygous ($Tph1^{+/-}$) mice were interbred to generate $Tph1^{-/-}$ and $Tph1^{+/+}$ littermates. Starting at 8 weeks of age, male $Tph1^{-/-}$ and $Tph1^{+/+}$ mice received either a chow (17% kcal fat; Diet 8640, Harlan Teklad, Madison, Wis.) or high-fat diet (HFD, 45% kcal fat, D12451, Research Diets; New Brunswick, N.J.) and water ad libitum for 12 weeks. For the initial chemical inhibitor studies, male C57BL/6 mice were purchased from Jackson's Laboratory at 6 weeks of age and immediately placed on the HFD described above. Starting at 8 weeks of age HFD-fed C57Bl6 mice received a daily intraperitoneal injection of the Tph1 inhibitor, LP533401 (25 mg/kg body weight, Dalton Pharma Services, Canada) dissolved in DMSO and diluted with water (5% DMSO final concentration) or equal volume of vehicle (5% DMSO in water). This protocol has previously been shown to effectively suppress circulating serotonin. All mice were housed in SPF microisolator cages that were located in a room maintained at a constant temperature of 23° C. on a 12 h light/dark cycle with lights on at 0700.

Ucp1 heterozygous mice were acquired from Jackson Laboratories and bred to produce UCP1-null (Ucp1$^{-/-}$) and wild-type (Ucp1$^{+/+}$) littermates. In order to prevent thermal stress, mice in this colony were bred and housed in a room maintained at 30° C. All testing except for the CL-316,243 challenge occurred at this temperature.

Metabolic monitoring was performed in a Comprehensive Lab Animal Monitoring System (CLAMS, Columbus Instruments, OH, USA) as previously described (Sachithanandan, N., et al. *Hepatology* 52, 1632-1642 (2010); O'Neill, H. M., et al. *Proc Natl Acad Sci* 108, 16092-16097 (2011)). CL-316,243 challenge experiments were also performed using the CLAMS equipment, as described. All metabolic monitoring occurred in a room kept between 26 and 28° C. Insulin and glucose tolerance tests were performed after 16 weeks of the diet intervention in Tph1$^{-/-}$ mice experiments, and after 6-10 weeks of HFD weeks in LP533401 injection experiments as previously described (Steinberg, G. R., et al. *J Biol Chem* 285, 37198-37209 (2010)). For serum insulin and cytokine measurements, fasting and fed blood samples were collected by retro-orbital bleed between weeks 16-18 using a non-heparinized capillary tube and insulin, adiponectin, leptin were measured as described (Watt, M. J., et al. *Nature medicine* 12, 541-548 (2006)). Serum cytokines (MCP-1, TNFα, and IL-6) were measured using a multiplexed bead-based immunoassay (BD Biosciences, San Jose, Calif., USA) following the manufacturer's instructions.

In vivo glucose uptake and body composition: $^{18}$F-Fluorodeoxyglucose (FDG) was synthesized at McMaster University by the nucleophilic substitution method using an FDG synthesizing instrument (GE Healthcare, Milwaukee, Wis., USA) and a cyclotron (Siemans 20-30 gb). After an 8 h fast, mice were injected with insulin (0.5 U/kg) diluted in 0.9% physiological saline and 5 minutes later received an intravenous administration of FDG (10.8±1.2 MBq/g). After injection, the mice were maintained under conscious conditions and warmed using a heating pad. At 28 minutes post saline or insulin injection mice were anaesthetized with isoflorane and at 30 minutes small-animal positron emission tomography (PET, Philip Mosaic, Andover, Mass.) and micro-computed tomography (CT) (Gamma Medica-Ideas Xspect System, NorthRidge, Calif.) imaging were performed using an acquisition time of 15 min for PET, followed by CT for 5 minutes. Images were reconstructed using 3D-RAMLA algorithm, with no attenuation correction and no correction for partial-volume effects of the tomograph as previously described[31]. Quantification was performed by Region-of-interest (ROI) analysis using Amide Research Workplace software and FDG-tissue uptake calculated using the mean value of standard uptake values (SUV) as described (*Palanivel R, Diabetologia.* 55(11): 3083-93 (2012)). Analysis of total body fat composition were determined by using Amira software (Visage Imaging) and the mean value of voxels of segmented adipose were calculated and expressed relative to total body mass.

Analytical Methods. For mRNA analysis, tissues were lysed in TRIzol-reagent (Invitrogen, Carlsbad, Calif., USA) and RNA extracted for qRT-PCR. Immunoblotting of tissues was performed using antibodies and procedures as described (Beck Jorgensen, S. et al. *Diabetologia* (2009)). For immunohistochemistry paraffin-embedded epididymal fat, brown adipose tissue, and liver were sectioned, dewaxed and rehydrated prior to antigen retrieval as described (Galic, S., et al. *The Journal of clinical investigation* 121, 4903-4915 (2011)).

Statistical analysis. All results shown are mean±standard error of the mean (SEM). Results were analyzed using Student's t-test or one or two-way ANOVA where appropriate, using GraphPad Prism software. A Bonferonni post-hoc test was used to test for significant differences revealed by the ANOVA. Significance was accepted at $p \leq 0.05$.

Results

Figure 1:
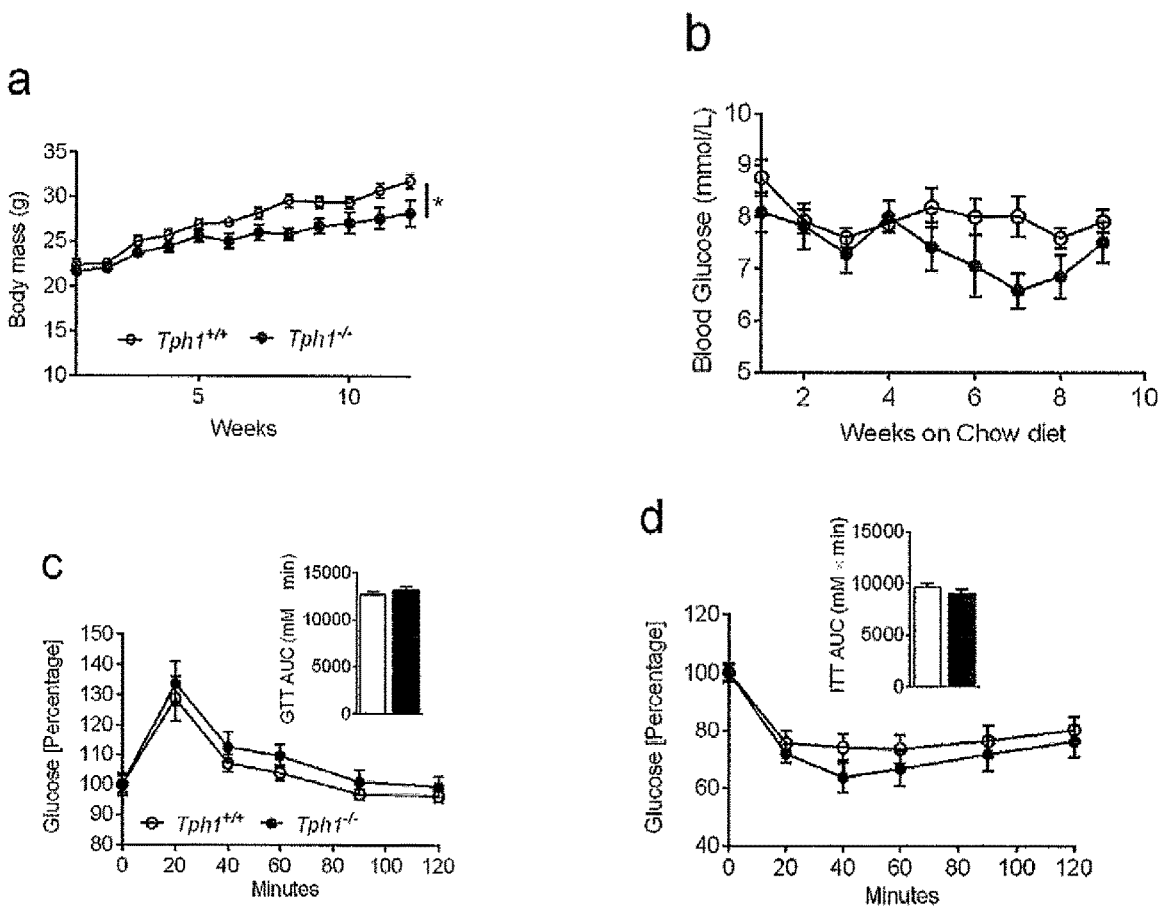
FIG. 1 graphically illustrates normal body mass (A), blood glucose concentrations over time (B), glucose tolerance (C) and insulin tolerance (D) in chow-fed (low-fat control diet) Tph1+/+ and Tph1−/− mice (data are mean SEM, n=7-10)
Figure 2:
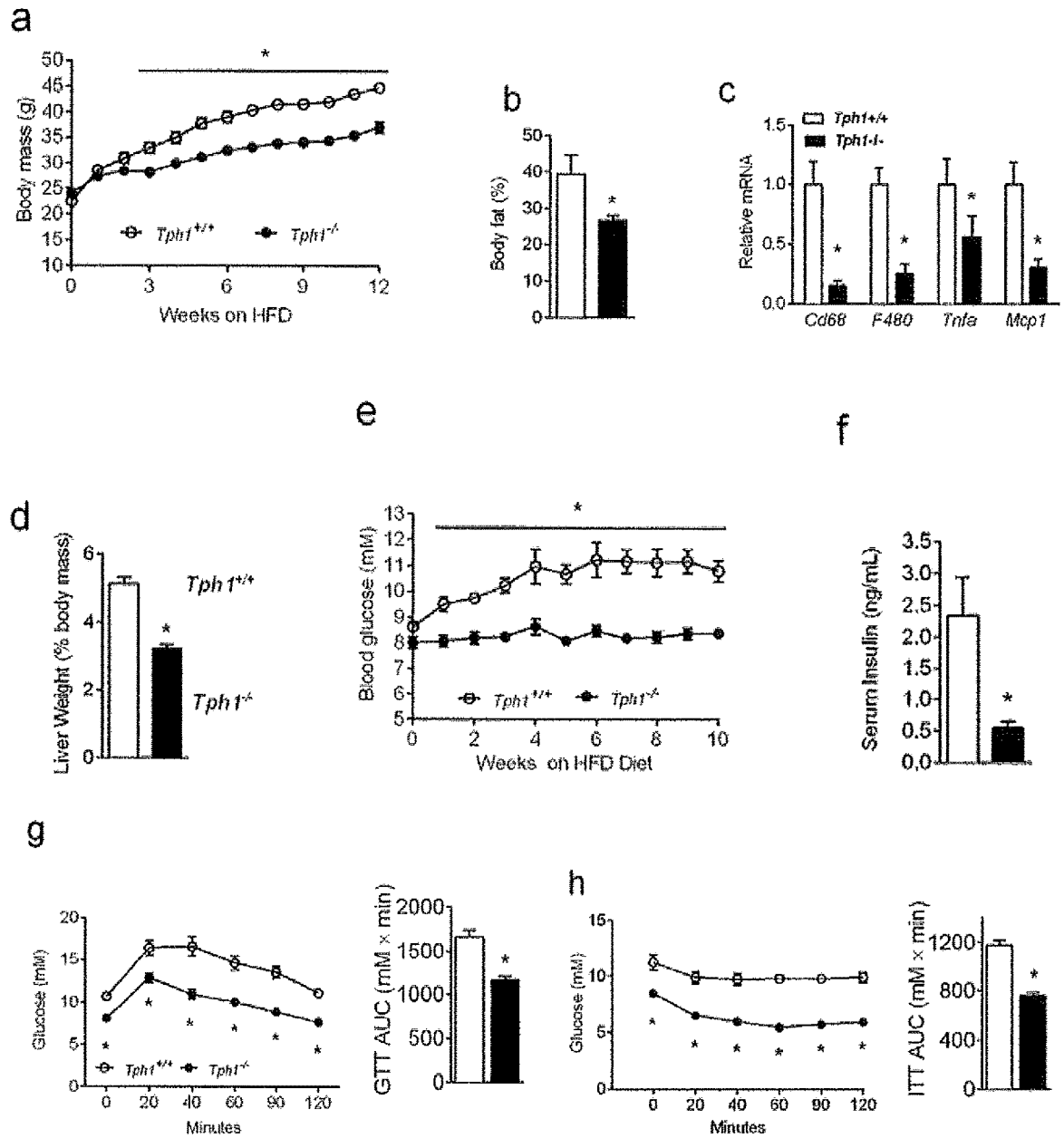
FIG. 2 graphically illustrates Tph1$^{-/-}$ mice are protected from obesity, chronic-low-grade inflammation, NALFD and insulin resistance as shown by a comparison of (a) body mass, (b) adiposity, (c) EWAT inflammation, (d) liver weights, (e) blood glucose over the course of the diet intervention, (f) fasting serum insulin concentrations, (g) GTT, (h) ITT performed after 10-12 weeks, (i) Akt$^{S473}$ phosphorylation relative to total Akt in liver, EWAT and mixed gastrocnemius muscle following sacrifice 15 minutes after an injection of saline or 0.5 U/kg insulin, each of Tph1$^{+/+}$ and Tph1$^{-/-}$ mice. Data are mean±SEM. *P<0.05 relative to chow-fed or Tph1$^{+/+}$ mice. #P<0.05 vs. all other groups. †P<0.05 vs. saline condition. EWAT, epididymal white adipose tissue; ITT, insulin tolerance test; GTT, glucose tolerance test; AUC area under the curve.
Figure 2:
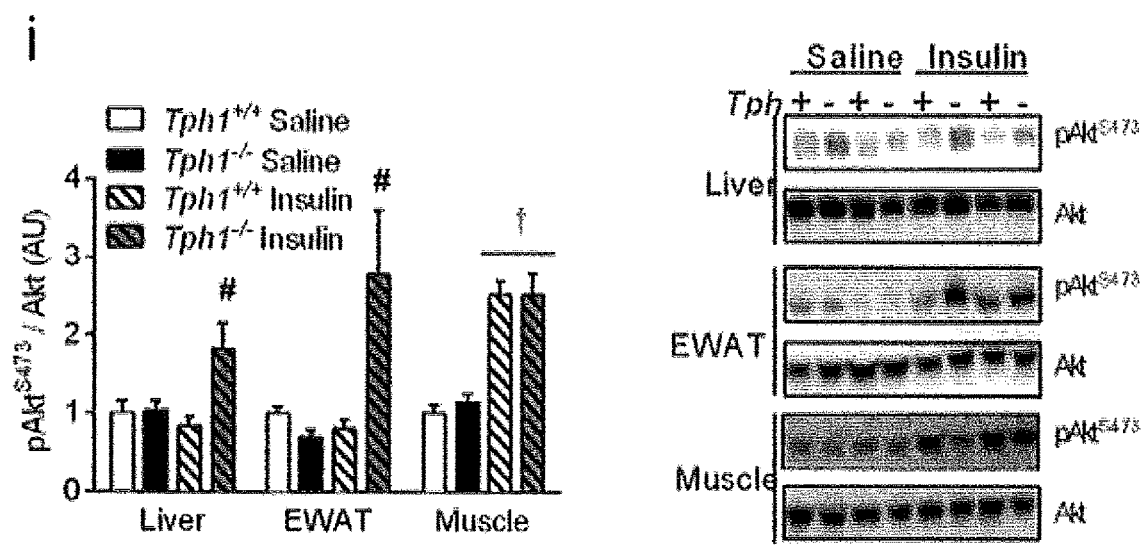

It was found that Tph1$^{-/-}$ mice fed a chow diet had normal body mass, blood glucose, glucose tolerance and insulin sensitivity compared to wild-type (Tph1$^{+/+}$) controls (FIGS. 1*a-d*). However, when fed a high fat diet (HFD), Tph1$^{-/-}$ mice were markedly protected from developing diet-induced weight gain (FIG. 2*a*). Further analyses revealed that HFD fed Tph1$^{-/-}$ mice had dramatic reductions in adiposity (FIG. 2*b*) that was associated with substantial reductions in markers of adipose tissue inflammation (FIG. 2*c*). HFD fed Tph1$^{-/-}$ mice also had reduced liver weights characterized by less lipid accumulation indicating protection from non-alcoholic fatty liver disease (NAFLD) (FIG. 2*d*), These data indicate that Tph1$^{-/-}$ mice are protected from developing obesity and related complications including low-grade chronic inflammation and NAFLD.

Obesity contributes to the development of insulin resistance and consistent with a reduction in body mass, Tph1$^{-/-}$ mice had reduced fasting blood glucose (FIG. 2*e*) and serum insulin (FIG. 2*f*) suggesting improvements in insulin sensitivity. Consistent with these changes, glucose tolerance (FIG. 2*g*) and insulin sensitivity (FIG. 2*h,i*) were markedly improved in Tph1$^{-/-}$ mice. These data indicate that Tph1$^{-/-}$ mice are protected from developing insulin resistance.

Figure 3:
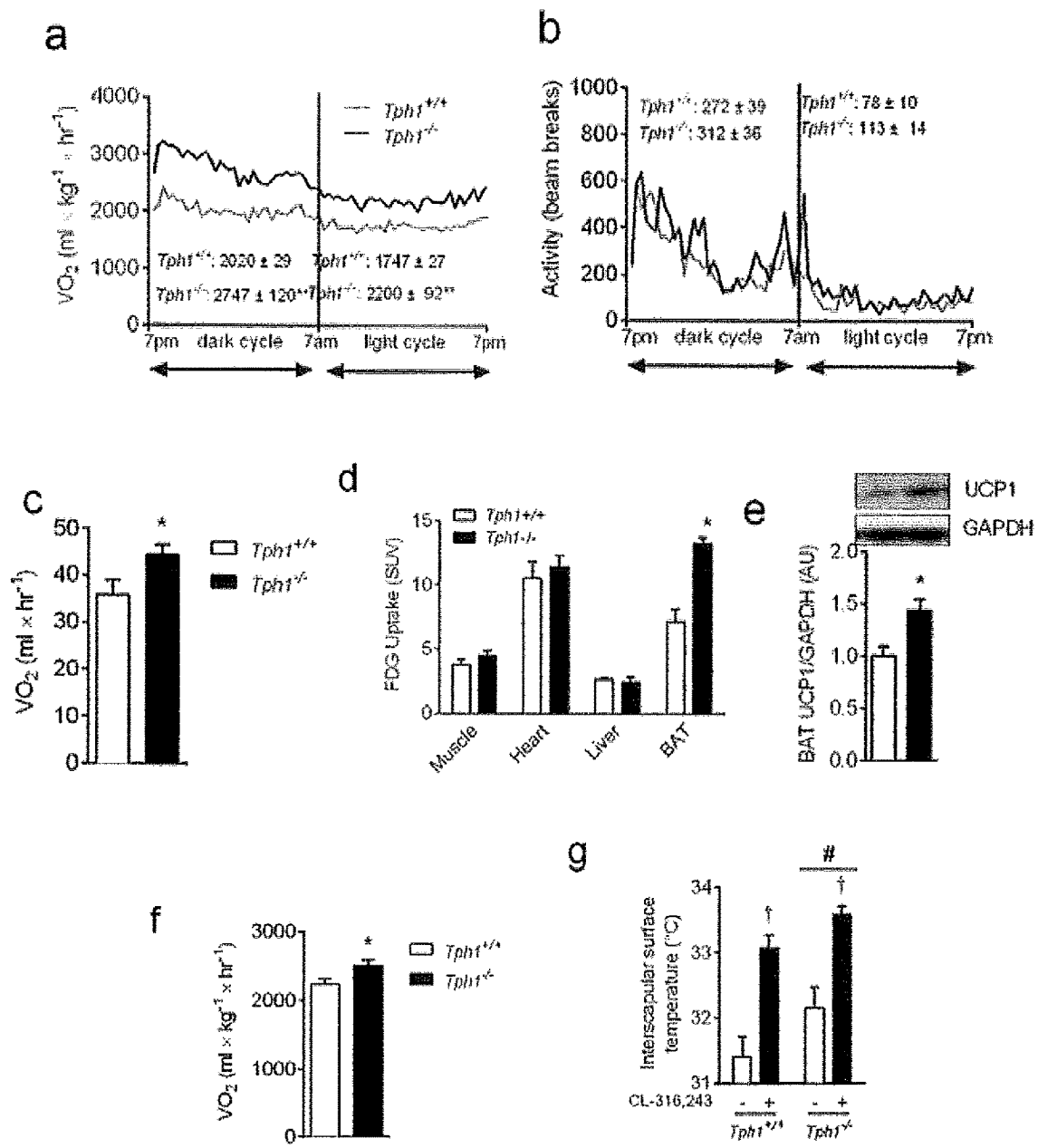
FIG. 3 shows that mice lacking Tph1 have increased metabolic rate and brown adipose tissue activity as graphically illustrated by (a) oxygen consumption, (b) activity levels over time, (c) basal metabolic rate (d) tissue FDG uptake derived from PET/CT imaging analysis, (e) UCP1 protein content in BAT as assessed by Western blot, (f) oxygen uptake and (g) plasma dorsal interscapular surface temperature following injection with saline or the β3-adrenergic activator CL-315,243, each of HFD-fed Tph1$^{+/+}$ and Tph1$^{-/-}$ mice. Data are mean±SEM, n 7-12. *P<0.05 relative to Tph1$^{+/+}$ mice. #Indicates an overall effect of genotype (P<0.05). †P<0.05 vs. saline condition.

To examine the mechanisms contributing to the attenuated weight gain of HFD-fed Tph1$^{-/-}$ mice, energy intake and expenditure was examined using metabolic cages. Oxygen consumption (VO$_2$) was ~20% greater in Tph1$^{-/-}$ mice (FIG. 3*a*), an effect that was independent of physical activity levels (FIG. 3*b*) and was also observed in anaesthetized mice even when not corrected for body mass (FIG. 3*c*), thus indicating an increase in basal metabolic rate. There was no difference in mean daily food intake between genotypes (Tph1$^{+/+}$=15.9±0.5 g Tph1$^{-/-}$=14.6±0.6 g, P>0.05, n=8). To determine which tissues were contributing to the increase in basal metabolic rate, $^{18}$fluorodeoxyglucose (FDG) uptake was measured using PET/CT. FDG uptake was dramatically increased in the BAT of Tph1$^{-/-}$ mice, but was unaltered in other organs (FIG. 3*d*). Collectively, these analyses indicated that Tph1$^{-/-}$ mice exhibited characteristics reflective of increased metabolic activity in BAT. Consistent with these findings, BAT from Tph1$^{-/-}$ mice was enriched with UCP1 (FIG. 3*e*). Additionally, when challenged with the β$_3$-adrenergic agonist, CL-316,243, Tph1$^{-/-}$ mice had a greater oxygen uptake (FIG. 3*f*) and thermogenesis, indicative of higher BAT activity. These findings indicate that the anti-obesity effect of Tph1 deletion is associated with increased brown adipose tissue activity.

Figure 4:
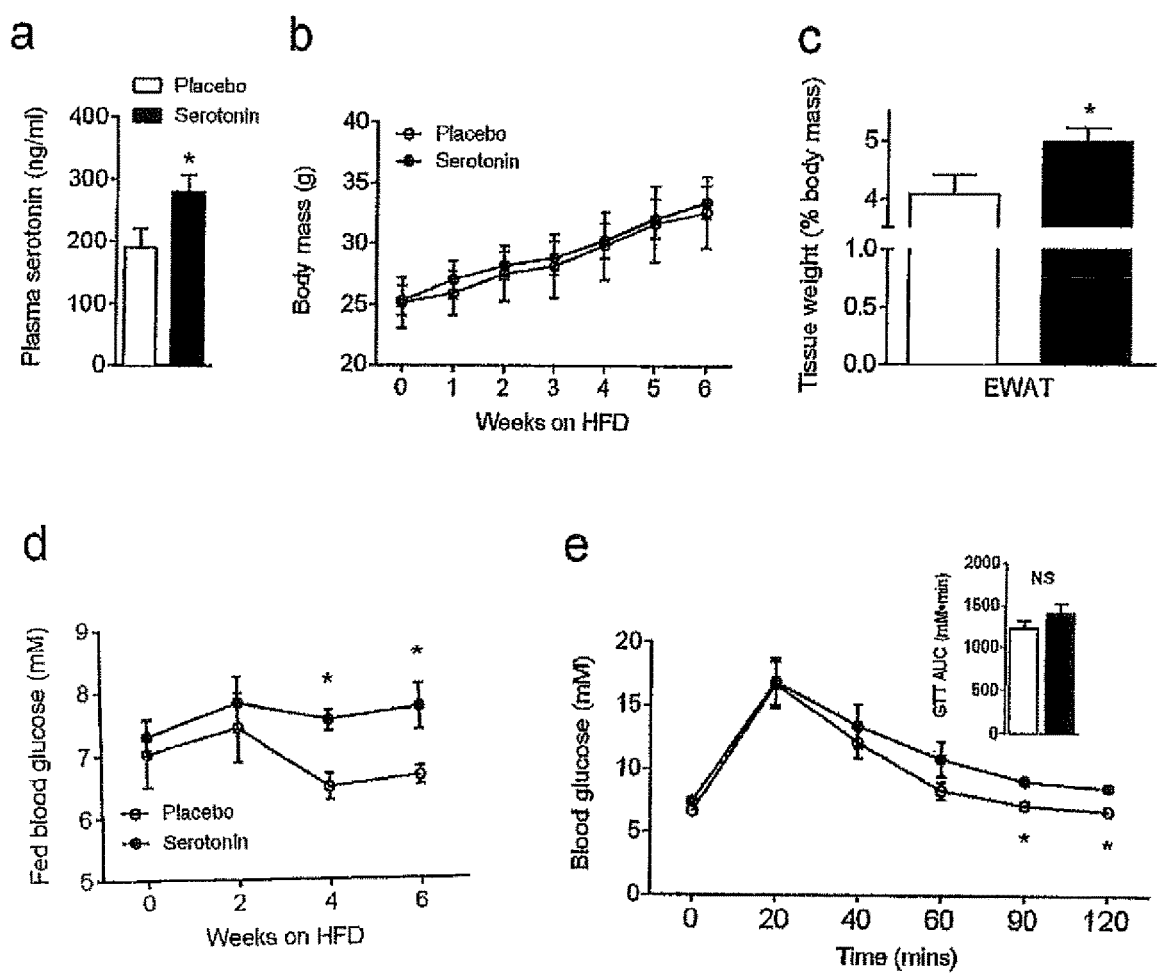
FIG. 4 graphically illustrates that replacement of serotonin in Tph1 null mice increases adiposity, reduces glucose tolerance and insulin sensitivity and suppresses basal metabolic rate and UCP1 mediated thermogenesis by a comparison of serum serotonin (a), body mass (b), EWAT mass (c), fed blood glucose overtime (d), glucose tolerance (e) and insulin sensitivity (f) in HFD-fed Tph1$^{-/-}$ mice implanted with subcutaneous placebo or serotonin producing pellet. Reduced oxygen consumption (g) without alterations in activity (h) or food intake (i) in HFD-fed Tph1$^{-/-}$ mice implanted with subcutaneous placebo or serotonin producing pellet. (j) Oxygen uptake and (k) plasma dorsal interscapular surface temperature of HFD-fed Tph1$^{-/-}$ mice implanted with subcutaneous placebo or serotonin producing pellet following acute injection with saline or the (β3- adrenergic activator CL-315,243. Data are mean±SEM, n=6-8. *P<0.05 relative to Placebo pelleted mice.
Figure 4:
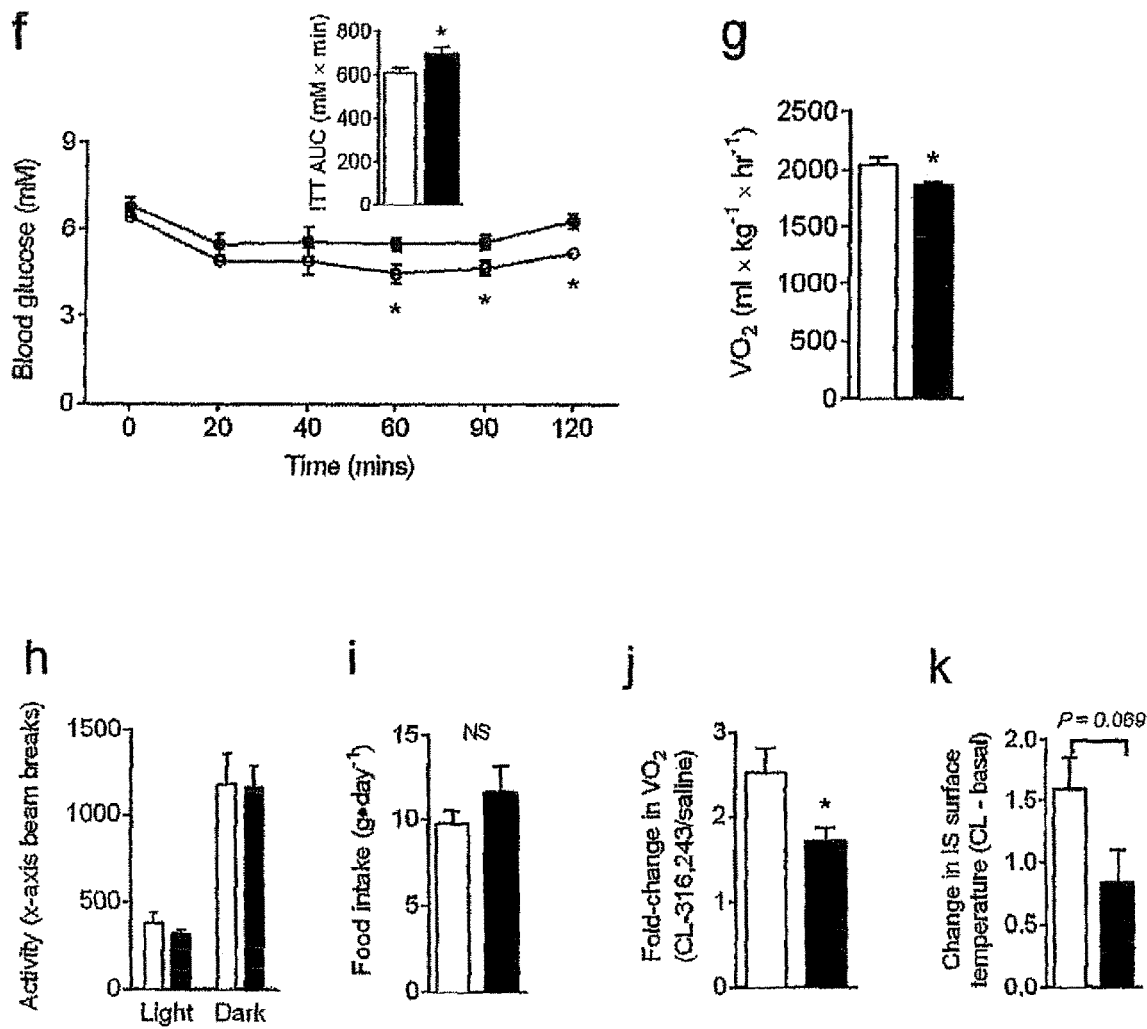

To confirm that serotonin was directly inhibiting brown adipose tissue, slow-release (60 day) serotonin or placebo pellets were implanted subcutaneously into HFD-fed Tph1$^{-/-}$ mice as a means to try and reverse the benefits of genetic Tph1 deletion. As expected, it was found that the serotonin pellets induced a modest increase in circulating serotonin (FIG. 4*a*) and although there was no detectable change in body mass (FIG. 4*b*), potentially due to the relatively small increase in serotonin levels which was still greatly reduced compared to WT mice fed a HFD, mice implanted with serotonin pellets had an ~20% increase EWAT tissue weights (FIG. 4c). Additionally, the increase in peripheral serotonin in Tph1$^{-/-}$ mice caused a small increase in fasting blood glucose and also a reduction in glucose tolerance and insulin sensitivity (FIG. 4d-f). Importantly HFD-fed Tph1$^{-/-}$ mice also had a reduction in basal metabolic rate, despite no behavioral changes in cage activity or food intake (FIG. 4g-i). In addition when challenged with CL-316,243, mice implanted with serotonin pellets had an attenuated stimulation of oxygen uptake, and a tendency for lower thermogenesis (FIG. 4j-k). These findings demonstrate that serotonin is directly regulating BAT activity in vivo.

HFD-fed C57Bl6 mice were treated with intraperitoneal injections of LP533401 (a Tph1 inhibitor) at a dose of 25 mg/kg body weight (Dalton Pharma Services, Canada) for 10 weeks. It was found that the ip injection of LP533401 reduced circulating serotonin levels (FIG. 5a). As anticipated, HFD-fed mice treated with vehicle gained approximately 1-2 grams per week over the treatment period, but remarkably this weight gain was suppressed in mice treated with LP533401 (FIG. 5b). Similar to the effects of Tph1 deletion, LP533401 treatment resulted in a lower accumulation of body fat (FIG. 5c and Table 1), reductions in liver size (FIG. 5d), improvements in glucose homeostasis (FIG. 5e-f) and increased insulin sensitivity (FIG. 5g).

TABLE 1

Tissue weights (mg) of HFD-fed C57Bl6 mice treated with vehicle or Tph1 inhibitor

|  | Vehicle | Tph1 Inhibitor | p-value |
|---|---|---|---|
| Heart | 172 ± 4.03 | 153 ± 10.6 | 0.11 |
| Spleen | 116 ± 5.56 | 147 ± 23.3 | 0.16 |
| Brown Adipose Tissue | 321 ± 44.8 | 153 ± 8.4 | 0.01 |
| Retroperitoneal Fat Pad | 442 ± 30.5 | 265 ± 29.9 | 0.0016 |
| Inguinal Fat Pad | 183 ± 21.5 | 117 ± 16 | 0.036 |
| Epididymal Fat Pad | 2075 ± 160 | 1157 ± 121 | 0.001136 |

Data are values ± SEM, n = 7-8 mice per group.

Importantly, similar results were also obtained when mice were first made obese by HFD-feeding for 8 weeks before the initiation of daily Tph1 inhibitor treatment (FIG. 6a-f). Thus, chemical inhibition of Tph1 phenocopies the effects of Tph1 genetic deletion for preventing and reversing obesity and related complications including NAFLD and insulin resistance.

To examine the mechanisms contributing to weight loss in LP533401-treated mice, HFD-fed mice were placed in metabolic cages after 12 days of treatment before any change in body mass was evident in groups (Vehicle: 29.4±0.58 g vs. LP533401:28.9±0.63 g). LP533401 treatment increased oxygen consumption during both the dark and light cycles without altering activity levels (FIG. 7a-b) or food intake (Vehicle=13.0±0.65 g vs. Inhibitor=13.7±0.45 g, P>0.05, n=8). $^{18}$FDG-PET/CT analysis was subsequently performed, and it was found that treatment with LP533401 increased FDG uptake in BAT (FIG. 7c) consistent with enhanced expression of UCP1 and reduced lipid deposition (FIG. 7d). These data demonstrate that chemical Tph1 inhibition increases energy expenditure and BAT activity analogous to findings observed in Tph1$^{-/-}$ mice.

In order to establish whether the clinical benefits of Tph1 inhibition (weight loss and improvements in insulin sensitivity) are derived from increased thermogenesis mediated by UCP1, daily injections of LP533401 were performed using UCP1-null (Ucp1$^{-/-}$) and wild-type littermates (Ucp1$^{+/+}$) fed a HFD and housed under thermoneutral conditions (30° C.). Remarkably, Ucp1$^{+/+}$, but not Ucp1$^{-/-}$ mice had attenuated weight gain due to LP533401 treatment (FIG. 8a). In addition improvements in glucose tolerance elicited by LP533401 were entirely dependent on the expression of UCP1 (FIG. 8b). Furthermore, when challenged with CL-316,243, only Ucp1$^{+/+}$ mice treated with LP533401 exhibited an increase in oxygen uptake and thermogenesis (FIG. 8c-d). Thus, the clinical benefits of Tph1 inhibition require UCP1 mediated thermogenesis.

To examine the mechanism by which serotonin may regulate brown adipose tissue activity, urinary catecholamines (epinephrine, norephinephrine, and dopamine) were examined and it was found that surprisingly, sympathetic tone was lower in Tph1$^{-/-}$ mice suggesting that instead serotonin may be altering the sensitivity of BAT to catecholamines (Table 2).

TABLE 2

Urinary and adipose tissue catecholamines in Tph1+/+ and Tph1−/− mice fed a high-fat diet

|  | Tph1+/+ | | | Tph1−/− | | |
|---|---|---|---|---|---|---|
|  | Urine (ng/ml) | WAT (pg/mg) | BAT (pg/mg) | Urine (ng/ml) | WAT (pg/mg) | BAT (pg/mg) |
| Epinephrine | 29.7 ± 3.95 | 113 ± 8.6 | 170 ± 9.8 | 16.4 ± 3.37* | 106 ± 4.7 | 286 ± 78 |
| Nor-epinephrine | 174 ± 4.8 | 8.7 ± 2.0 | 18.6 ± 1.0 | 170 ± 3.3 | 8.5 ± 2.0 | 18.6 ± 0.9 |
| Dopamine | 306 ± 7.8 | 1.5 ± 0.5 | 12.1 ± 0.7 | 270 ± 4.2* | 1.4 ± 0.4 | 15.4 ± 2.8 |

Data are means ± SEM, n = 6-10,
*P < 0.05 versus TPH1 +/+.

As the expression of UCP1 and activity of BAT is largely dependent on changes in cAMP, cAMP levels were measured and it was found that cAMP was higher in HFD-fed Tph1$^{-/-}$ mice (FIG. 9a). To examine whether serotonin could alter cAMP and the induction of the thermogenic program in a cell autonomous manner, BAT cells were treated with the concentrations of serotonin observed in the BAT of Tph1$^{+/+}$ mice fed a HFD (FIG. 9b) prior to stimulation with isoproterenol (a cAMP agonist). Serotonin treatment attenuated isoproterenol-stimulated cAMP and phosphorylation of protein kinase A substrates such as hormone sensitive lipase (HSL S660-FIG. 9c) and importantly also blunted the induction of the thermogenic gene program (FIG. 9d-f). Thus, serotonin directly inhibits BAT, cAMP and the thermogenic program, suggesting that in addition to Tph1 inhibition, antagonism directed towards serotonin receptors may be effective in increasing BAT theromogenesis.

Lastly, since the browning of white adipocytes into beige or brite cells has been recently suggested to play an important role in regulating energy expenditure and possibly body mass, these characteristics in Tph1$^{-/-}$ and Tph1 inhibitor-treated mice were assessed. It was found using PET-scanning that visceral WAT FDG uptake was increased in mice with genetic or chemical inhibition of Tph1 (FIG. 10a). Consistent with these changes in visceral white adipose tissue metabolic activity, it was found that markers of beige or brite cells were observed as Ucp1, Cidea and Pgc1a expression were also increased in eWAT and inguinal WAT depots (FIG. 10b-c). Increased browning of eWAT was also macroscopically evident (FIG. 10d) in Tph1 inhibitor treated mice and was associated with marked expression of UCP1 as assessed by immunostaining (FIG. 10e). These data indicate that in addition to increasing BAT activity, Tph1 inhibition also promotes the browning of white adipose tissue. This finding is of clinical importance for the treatment of human obesity given the large amount of white adipose tissue present in obese humans and the suggestion that brown fat in humans may be closely related to rodent beige or brite adipocytes.

Discussion

Tph1$^{-/-}$ mice and the pharmacological inhibition of Tph1 in wild-type mice were used to investigate the role of peripheral serotonin on energy homeostasis and the development of obesity. HFD-induced obesity causes an elevation in adipose tissue serotonin levels that is dependent on the expression of Tph1, indicating that serotonin production is under nutrient control. While previous studies in *C elegans* have demonstrated that serotonin increases energy expenditure by upregulating fatty acid oxidation, the present findings show the opposite is true in mammals.

Genetic or chemical inhibition of Tph1 protected or reversed the development of HFD-induced obesity and dysglycemia by increasing UCP1-mediated thermogenesis. These data provide the first evidence for a role of peripheral serotonin in controlling adipose tissue energy metabolism. This finding links an ancient molecule that is essential for regulating energy balance across phyla to the control of brown adipose tissue in mammals. As BAT activity is reduced in obesity, it is herein indicated that the inhibition of Tph1, serotonin or serotonin receptors is effective in reversing obesity and related disorders.

Example 2

Effect of Serotonin Receptor Inhibition

Methods

Cell Culture. An immortalized brown adipocyte (BA) cell line derived from mouse fetal brown fat (as described in Uldry et al., Cell metabolism, 3 (2006) 333-341) was cultured and differentiated as previously described in Mottillo, Journal of Biological Chemistry, 287 (2012) 25038-25048. Briefly, confluent cells were placed in induction media (0.5 mM IBMX; 0.25 mM indomethacin; 2 µg/ml dexamethasone; 1 nM T3, 20 nM insulin) for two days and subsequently maintained on differentiation media (1 nM T3, 20 nM insulin). All experiments were performed on cultures 6-8 days post-induction. Unless otherwise indicated, cells were rinsed with PBS and media was changed to HEPES-buffered Krebs Ringer buffer (HKRB)+1% BSA. Where indicated, BAs were treated with serotonin for 30 min (100 µM; Sigma) followed by isoproterenol (1 nM, Sigma) for 4 h. The serotonin receptor antagonist, methysergide (3 µM) was used 45 min prior treatment with serotonin as above.

cAMP measurements. cAMP levels were measured in BA stimulated for 10 min with isoproterenol (1 nM). Cells were lysed with 0.1 M HCl, 0.2% Triton-X-100 for 20 min and acidified cell lysates were collected and neutralized with NaOH and centrifuged at 5000×g for 5 min and the supernatant was collected. The cAMP levels were quantified by ELISA (Biomedical Technologies Inc.) as previously described (Mottillo et al., American Journal of Physiology—Endocrinology And Metabolism, 301 (2011) E122-E131).

Quantification of FFAs. FFA released into medium were quantified after 1 h of stimulation with isoproterenol using a NEFA-HR(2) kit (Wako Chemicals, USA) as suggested by the manufacturer.

RNA extraction and gene expression analysis. RNA from BAs was isolated using a Nucleospin RNA II kit (Macherey-Nagel). The expression pattern of various genes was quantified by qRT-PCR analysis, as previously described (Mottillo et al., American journal of physiology, 293 (2007) E1188-1197). Briefly, RNA (1-2 µg) was reverse transcribed into cDNA by using Superscript III (Invitrogen) and random hexamers primers as recommended by the manufacturer. 25 ng of cDNA was analyzed in a 10 µl quantitative PCR reaction (Amplitaq Gold) as previously described. Expression data were normalized to the house-keeping gene RNA polymerase IIA (Polr2A) using the delta-delta CT method ($2^{-\Delta\Delta CT}$ (Livak et al.), Methods, 25 (2001) 402-408).

Protein isolation and western blot analysis. Proteins were extracted in Cell lysis buffer (25 mM Tris pH 7.5, 150 mM NaCl, 1% Triton-X-100, 0.5%, Na-deoxycholate, 1% NP-40, and 1 mM EDTA) containing protease inhibitors (Roche) and phosphatase inhibitors (100 uM NaF, 2 mM NaOrthovandate). Lysates were solubilized for 15 min at 4° C. and centrifuged at 16,000×g for 10 min to clear lysate. The extracts were recovered and proteins were quantified by using the bicinchoninic acid method (Pierce). SDS-PAGE was performed under reducing conditions and resolved proteins were transferred to PVDF. Membranes were immunoblocked for 1 hr at room temperature in 5% powdered skim milk and probed overnight for antibodies against phosphor-HSL S660 and total HSL (Cell Signal). Blots were then washed, incubated with a secondary goat anti-rabbit HRP (Cell Signal) diluted 1:10,000, and visualized with SuperSignal West Femto substrate (Pierce).

Results

The results, as shown in FIG. 11, demonstrate that serotonin (5-HT@100 µM) blunts isoproterenol-induced increases in lipolysis (an indirect functional measure of cAMP) and this effect is blocked by co-treatment with the 5-HT receptor antagonist, methysergide. Data are based on n=2 from immortalized BAT cells.

Example 3

Inhibition of 5-HT2A

Using RNA-Seq, cultured human brown and beige adipocytes were interrogated for 5-HT receptor mRNA expression. Immortalized murine brown adipocytes (BAs) were treated with or without the selective 5-HT reuptake inhibitor (SSRI), paroxetine (250 nM). Subsequent studies were conducted with and without 5-HT2A agonists (1 pM-10 uM TCB-2, 1 pM-10 uM AL-34662, and 1 pM-10 uM NBOH-2C-CN) and 5-HT2A antagonists (100 fM-100 pM MDL-100907, 100 pM-10 uM xylamidine tosylate, 1 nM ketanserin, 10 nM altanserin, 100 fM-100 pM EMD-281,014, and 100 pM-10 uM sarpogrelate hydrochloride).

Immortalized BA progenitor cells obtained from 5-HT2A KO (B6; 129-5-HT2Atm1a/Nju from Nanjing Biomedical Research Institute of Nanjing University) mice were differentiated for 9 days to produce mature BAs. Cells were then stained with fluo-4 and treated with different concentrations of 5-HT to obtain a dose response curve. Values from BAs expressing 5-HT2A used for other experiments were plotted as a WT comparison.

BA progenitors were isolated and immortalized from WT and serotonin transporter (SERT; Gene: Slc6a4) KO mice. These cells were then differentiated for 7 days to obtain mature BAs. BAs were then treated with different doses of 5-HT for 4 hours. RNA was isolated and quantified using RT-qPCR with probes specific for Slc6a4, Ucp1 and PPIA.

BA progenitors were isolated from mice expressing a transgene where the luciferase gene is driven by the Ucp1 promoter (i.e. Ucp1-Luc2 mice; a.k.a. ThermoMouse; Jackson Laboratories). Upon 9 days of differentiation, these BAs were treated for 4 hours with different doses of 5-HT. Because in vitro there is not a continuous supply of 5-HT as there is in vivo, cells were treated with paroxetine to inhibit the uptake and consequent degradation of 5-HT, and to observe 5-HT receptor specific effects. These cells were then lysed, incubated with a luciferin assay cocktail, and the light generated quantified on a microplate reader.

To investigate effects in vivo, 5-HT (5 mg/kg i.p.) was acutely administered to mice with or without a peripherally-restricted 5-HT2A antagonist (xylamidine tosylate) (3 mg/kg i.p.) to assess BAT function. Chow fed female FVBNJ mice (Jackson laboratories) were fasted for 6 hours. Each mouse was intraperitoneal injected with Vehicle (0.9% NaCl) or Xylamidine (3 mg/kg in 0.9% NaCl) at −100 minutes, followed by Vehicle or 5-HT (5 mg/kg in 0.9% NaCl) at −40 minutes, and finally Glucose (2 mg/kg) at 0 minutes. Blood glucose was monitored at the indicated times (FIG. 22). Chow mice were administered xylamidine tosylate (3 mg/kg daily) via intraperitoneal injection for ~5 weeks. Mice were then moved to anaesthetized and injected with either saline or CL-316,243. Oxygen consumption was recorded while at 30° C. Finally, xylamidine tosylate (3 mg/kg i.p. daily) was administered to mice on a HFD and indices of whole body metabolism, such as resting energy expenditure, glucose tolerance and NAFLD, were evaluated. The mRNA and protein expression of markers of beige adipose tissue (UCP1, PRDM16, NDUFB8, SDHB, MTCO1, UQCRC2 and ATP5A) were also evaluated.

Results

Brown and White Adipose Tissue Express Active 5-HT2A Receptors That Inhibit Thermogenic Gene Expression—Treatment of cultured brown adipocytes with 5-HT decreased UCP1 protein content, only in the presence of a selective serotonin reuptake inhibitor (SSRI; paroxetine hydrochloride—FIGS. 14A and B). Because SSRIs prevent 5-HT entry into the cell and consequent metabolism, this experiment indicated that UCP1 protein is decreased via a 5-HT receptor mediated mechanism.

To determine the primary 5-HT receptor expressed in adipose tissue, RNA-Seq analysis of cultured human brown and white adipose tissue was completed. It revealed that 5-HT2A (Gene: HTR2A) mRNA was expressed at much greater levels than all other serotonin receptors (FIG. 14C), indicating it is the primary 5-HT receptor expressed in adipose tissue. Active Gq-coupled receptors (such as 5-HT2A) increase IP3 formation and consequently stimulate IP3 receptors on the endoplasmic reticulum resulting in $Ca^{2+}$ release. After staining brown adipocytes with the calcium sensitive dye, Fluo-4, treatment with 5-HT and known selective 5-HT2A agonists (NBOH-2C-CN, TCB-2, and AL-34662) increased $Ca^{2+}$ levels demonstrating that $HTR_2a$ are active in brown adipocytes (FIG. 14D).

5-HT2A receptors induce the thermogenic program in adipocytes—To determine if 5-HT2A receptors induced the thermogenic program in adipocytes, gene array data from mesenchymal stem cells (MSC) was compared to adipocytes differentiated from MSC overexpressing PGC-1α to find a unique gene signature. Using this gene signature and the NIH Library of Integrated Network-based Cellular Signatures (LINCS) Database, 29 compounds were identified that induced thermogenic genes (not shown). Of these compounds, 5-HT2A antagonists (altanserin, pimozide and nortriptyline; FIG. 15) were significantly over-represented (one-sided Fisher's Exact test of 3 5-HT2A in top 25 drugs; p=0.03) and inhibitors of downstream pathways of 5-HT2A were also present (midostaurin and isoxicam). Thus, 5-HT2A antagonists were predicted to induce the thermogenic program in adipocytes.

Known 5-HT2A Antagonists Block 5-HT Adaptive Effects in Brown Adipocytes—Pre-treatment with 5-HT2A antagonists attenuated 5-HT induced $Ca^{2+}$ transients, indicating that these compounds are capable of blocking 5-HT induced effects in brown adipocytes (FIG. 16). Furthermore, 5-HT decreased Ucp1 promoter activity, Ucp1 mRNA, and UCP1 protein levels (FIGS. 17A-C and E). A selective 5-HT2A agonist, NBOH-2C-CN, also inhibited Ucp1 mRNA levels and all antagonists of 5-HT2A blocked the 5-HT-induced reduction (FIG. 17B-C). Furthermore, chronic treatment with NBOH-2C-CN resulted in decreased UCP1 protein levels (FIG. 17D), and MDL-100907 dose-dependently attenuated the 5-HT induced decrease in UCP1 protein levels (FIG. 17E). Furthermore, unlike WT BAs, BAs with Htr2a deleted did not respond to 5-HT (FIG. 21). Demonstrating that genetically deleting Htr2a results in BAs that are resistant to the effects of 5-HT.

In Vivo Antagonism of 5-HT2A Rescues Energy Expenditure and Improves Glucose Tolerance—Under thermoneutral conditions (i.e. when brown adipose tissue is inactive) administration of 5 mg/kg 5-HT had no effect on markers of brown adipose tissue activity (FIG. 18A and C). However, when brown adipose tissue is selectively activated using the β3-adrenergic receptor agonist CL-316,243, 5-HT significantly attenuated brown adipose tissue associated oxygen consumption and inter-scapular surface area temperature (FIG. 18B and D). Pre-treatment with a peripherally-restricted antagonist of 5-HT2A (xylamidine tosylate) completely blocked the effects of 5-HT. This indicates that elevated levels of peripheral 5-HT result in decreased brown adipose tissue activity and energy expenditure via peripheral 5-HT2A. Acute administration of xylamidine improved glucose tolerance in mice and this effect was larger when pre-treated with 5-HT (FIG. 22). This indicated that acute blockade of the 5-HT2a receptor improved glucose tolerance both with basal and elevated levels of 5-HT.

Chronic Effects of 5-HT2A Antagonism on Diet-Induced Obesity (DIO)—Repeated administration of xylamidine increased brown adipose tissue specific energy expenditure in chow mice-indicating that inhibition of 5-HT2a resulted in increased brown adipose tissue capacity and consequently suggesting this would lead to reduced weight gain in high fat diet fed mice (FIG. 23). Independent of changes in body mass or body fat, administration of xylamidine tosylate (3 mg/kg daily) resulted in improved glucose tolerance in mice fed a high fat diet (45% of calories from fat; FIG. 19C and D). Furthermore, these mice exhibited increased oxygen consumption, heat production, and non-moving oxygen consumption (FIG. 19E-G). These all indicate an elevated basal metabolic rate, indicative of increased brown adipose tissue activity. Chronic administration of xylamidine to high fat diet mice prevented weight gain and specifically increases in fat mass (FIG. 24).

Upon sacrificing these animals, it was found that numerous adaptations consistent with increased thermogenic capacity of adipose tissue were present. Subcutaneous adipose tissue (inguinal white adipose tissue; iWAT) had elevated mRNA levels of the key thermogenic gene Prdm16 that is required for the formation of beige adipose tissue (FIG. 20A). Additionally, iWAT had increased levels of the essential thermogenic protein, UCP1, and mitochondrial proteins further indicating the development of beige adipose tissue (FIG. 20B-C). Livers from xylamidine-treated mice had significantly reduced triglycerides levels-consistent with the increased energy expenditure observed which would result in decreased lipid deposition in the liver (FIG. 20D). These tissue changes are consistent with improved energy expenditure due to thermogenic adaptation of brown adipose tissue and the conversion of white adipose tissue to beige adipose tissue.

SERT KO cells do not express SERT (FIG. 25A). Unlike WT cells that only experience reductions of Ucp1 mRNA level at high doses of 5-HT (FIG. 17B), because of their inability to uptake and degrade 5-HT, SERT KO cells are consequently sensitive to very low levels of 5-HT and experience decreases in Ucp1 mRNA at lower doses of 5-HT (FIG. 25B). Furthermore, treatment of cells with an SSRI also results in an increased sensitivity of the Ucp1 promoter (as compared to untreated cells in FIG. 17A) to inhibition by 5-HT (FIG. 25C-D). These results suggest that SSRIs render brown adipose tissue particularly sensitive to 5-HT inhibition via receptor mediated mechanisms, suggesting a mechanism by which many SSRIs might promote weight gain.

As shown in FIG. 17C and E, inhibition of brown fat by high dose 5-HT can be rescued with 5-HT2a blockade and thus that SSRI induced attenuations of energy expenditure may be rescued with 5-HT2a blockade.

Discussion

In this study, it was found that: 1) 5-HT inhibited brown adipose tissue via a cell surface receptor mechanism, 2) 5-HT2A is highly expressed in human BAT, 3) connectivity mapping reveals that 5-HT2A antagonists are associated with the browning of white adipocytes, 4) 5-HT acutely inhibited BAT function and 5-HT2A antagonists block this effect, 5) 5-HT2A agonists mimic the effect of 5-HT to inhibit BAT function and 6) acute treatment of mice with a peripherally restrained 5-HT2A antagonist blocks the effects of 5HT to inhibit BAT function in vivo, and 7) chronic treatment with xylamidine tosylate increases energy expenditure and improves glucose tolerance and NAFLD in mice fed a high-fat diet. In conclusion, 5-FIT inhibits BAT via 5-HT2A. Acute, peripheral pharmacological blockade of this receptor restores BAT function and chronic administration improves glucose tolerance, and is useful to treat obesity, glucose intolerance, NAFLD and insulin resistance.

The invention claimed is:

1. A method of treating a non-obese human subject having non-alcoholic fatty liver disease comprising the step of administering to the subject a compound that inhibits peripheral 5-HT2a selected from the group consisting of: paroxetine, volinanserin (MDL-100907), eplivanserin, glemanserin, ketanserin, pimavanserin, ritanserin, xylamidine tosylate, altanserin, pruvanserin (EMD-281,014), pimozide, nortriptyline, clozapine, olanzapine, quetiapine, risperidone, asenapine, cyproheptadine, nefazodone, AMDA (9-aminomethyl-9,10-dihydro-anthracene), hydroxyzine (Atarax), 5-MeO-NBpBrT, niaprazine, naftidrofuryl, aripiprazole, AT 1015, DMT, DV 7028 hydrochloride, 4F 4PP oxalate, fananserin, melperone hydrochloride, mesulergine hydrochloride, paliperidone, PNU 96415E, R-96544 hydrochloride, spiperone hydrochloride, trazodone hydrochloride, ziprasidone hydrochloride, sarpogrelate hydrochloridec, zotepine, methysergide, mirtazapine, pizotifen, LY-367,265, 2-alkyl-4-aryl-tetrahydro-pyrimido-azepines, AC-90179, nelotanserin, midostaurin, isoxicam and derivatives of any of these which retain peripheral 5-HT2a inhibitory activity.

2. The method of claim 1, wherein the compound selectively inhibits 5-HT2a.

3. The method of claim 1, wherein the compound is a 5-HT2a antagonist.

4. The method of claim 1, wherein the compound is administered systemically.

5. The method of claim 1, wherein the compound is administered topically.

6. The method of claim 1, wherein the compound is administered to a mammal with a high fat diet.

7. The method of claim 1, wherein the expression of at least one of UCP1, PRDM16, or OXPHOS enzymes is upregulated.

8. The method of claim 1, wherein the compound is administered at a dosage in the range of about 0.1 to 1000 mg/kg.

9. The method of claim 1, wherein the compound is administered in conjunction with a treatment that increases peripheral circulating serotonin.

10. The method of claim 1, wherein the compound is an inverse agonist.

11. The method of claim 1, wherein the compound is MDL-100907, xylamidine tosylate, ketanserin, altanserin, EMD-281,014 or sarpogrelate hydrochloride.

* * * * *

SEQUENCE LISTING

```
<160> NUMBER OF SEQ ID NOS: 4

<210> SEQ ID NO 1
<211> LENGTH: 444
<212> TYPE: PRT
<213> ORGANISM: Homo sapiens

<400> SEQUENCE: 1

Met Ile Glu Asp Asn Lys Glu Asn Lys Asp His Ser Leu Glu Arg Gly
1               5                   10                  15

Arg Ala Ser Leu Ile Phe Ser Leu Lys Asn Glu Val Gly Gly Leu Ile
            20                  25                  30

Lys Ala Leu Lys Ile Phe Gln Glu Lys His Val Asn Leu Leu His Ile
        35                  40                  45

Glu Ser Arg Lys Ser Lys Arg Arg Asn Ser Glu Phe Glu Ile Phe Val
    50                  55                  60

Asp Cys Asp Ile Asn Arg Glu Gln Leu Asn Asp Ile Phe His Leu Leu
65                  70                  75                  80

Lys Ser His Thr Asn Val Leu Ser Val Asn Leu Pro Asp Asn Phe Thr
                85                  90                  95

Leu Lys Glu Asp Gly Met Glu Thr Val Pro Trp Phe Pro Lys Lys Ile
            100                 105                 110

Ser Asp Leu Asp His Cys Ala Asn Arg Val Leu Met Tyr Gly Ser Glu
        115                 120                 125

Leu Asp Ala Asp His Pro Gly Phe Lys Asp Asn Val Tyr Arg Lys Arg
    130                 135                 140

Arg Lys Tyr Phe Ala Asp Leu Ala Met Asn Tyr Lys His Gly Asp Pro
```

```
                145                 150                 155                 160
        Ile Pro Lys Val Glu Phe Thr Glu Glu Ile Lys Thr Trp Gly Thr
                        165                 170                 175
        Val Phe Gln Glu Leu Asn Lys Leu Tyr Pro Thr His Ala Cys Arg Glu
                        180                 185                 190

Tyr Leu Lys Asn Leu Pro Leu Ser Lys Tyr Cys Gly Tyr Arg Glu
                        195                 200                 205

Asp Asn Ile Pro Gln Leu Glu Asp Val Ser Asn Phe Leu Lys Glu Arg
                    210                 215                 220

Thr Gly Phe Ser Ile Arg Pro Val Ala Gly Tyr Leu Ser Pro Arg Asp
        225                 230                 235                 240

Phe Leu Ser Gly Leu Ala Phe Arg Val Phe His Cys Thr Gln Tyr Val
                        245                 250                 255

Arg His Ser Ser Asp Pro Phe Tyr Thr Pro Glu Pro Asp Thr Cys His
                        260                 265                 270

Glu Leu Leu Gly His Val Pro Leu Leu Ala Glu Pro Ser Phe Ala Gln
                        275                 280                 285

Phe Ser Gln Glu Ile Gly Leu Ala Ser Leu Gly Ala Ser Glu Glu Ala
                    290                 295                 300

Val Gln Lys Leu Ala Thr Cys Tyr Phe Phe Thr Val Glu Phe Gly Leu
        305                 310                 315                 320

Cys Lys Gln Asp Gly Gln Leu Arg Val Phe Gly Ala Gly Leu Leu Ser
                        325                 330                 335

Ser Ile Ser Glu Leu Lys His Ala Leu Ser Gly His Ala Lys Val Lys
                        340                 345                 350

Pro Phe Asp Pro Lys Ile Thr Cys Lys Gln Glu Cys Leu Ile Thr Thr
                        355                 360                 365

Phe Gln Asp Val Tyr Phe Val Ser Glu Ser Phe Glu Asp Ala Lys Glu
                        370                 375                 380

Lys Met Arg Glu Phe Thr Lys Thr Ile Lys Arg Pro Phe Gly Val Lys
        385                 390                 395                 400

Tyr Asn Pro Tyr Thr Arg Ser Ile Gln Ile Leu Lys Asp Thr Lys Ser
                        405                 410                 415

Ile Thr Ser Ala Met Asn Glu Leu Gln His Asp Leu Asp Val Val Ser
                        420                 425                 430

Asp Ala Leu Ala Lys Val Ser Arg Lys Pro Ser Ile
                    435                 440

<210> SEQ ID NO 2
<211> LENGTH: 1815
<212> TYPE: DNA
<213> ORGANISM: Homo sapiens

<400> SEQUENCE: 2
ttttagagaa ttactccaaa ttcatcatga ttgaagacaa taaggagaac aaagaccatt      60
ccttagaaag gggaagagca agtctcattt tttccttaaa gaatgaagtt ggaggactta     120
taaaagccct gaaaatcttt caggagaagc atgtgaatct gttacatatc gagtcccgaa     180
aatcaaaaag aagaaactca gaatttgaga tttttgttga ctgtgacatc aacagagaac     240
aattgaatga tatttttcat ctgctgaagt ctcataccaa tgttctctct gtgaatctac     300
cagataattt tactttgaag gaagatggta tggaaactgt tccttggttt ccaagaagaa     360
tttctgacct ggaccattgt gccaacagag ttctgatgta tggatctgaa ctagatgcag     420
accatcctgg cttcaaagac aatgtctacc gtaaacgtcg aaagtatttt gcggacttgg     480
```

```
ctatgaacta taaacatgga gaccccattc caaaggttga attcactgaa gaggagatta      540
agacctgggg aaccgtattc caagagctca acaaactcta cccaacccat gcttgcagag      600
agtatctcaa aaacttacct ttgctttcta aatattgtgg atatcgggag ataatatcc      660 cacaattgga agatgtctcc aacttttaa aagagcgtac aggttttcc atccgtcctg      720 tggctggtta cttatcacca agagatttct tatcaggttt agcctttcga gttttcact      780 gcactcaata tgtgagacac agttcagatc ccttctatac cccagagcca gatacctgcc      840
atgaactctt aggtcatgtc ccgcttttgg ctgaacctag ttttgcccaa ttctcccaag      900
aaattggctt ggcttctctt ggcgcttcag aggaggctgt tcaaaaactg caacgtgct      960 acttttcac tgtggagttt ggtctatgta acaagatgg acagctaaga gtctttggtg     1020
ctggcttact tcttctatc agtgaactca aacatgcact tctggacat gccaaagtaa     1080 agcccttga tcccaagatt acctgcaaac aggaatgtct tatcacaact tttcaagatg     1140
tctactttgt atctgaaagt tttgaagatg caaggagaa gatgagagaa tttaccaaaa     1200
caattaagcg tccatttgga gtgaagtata atccatatac acggagtatt cagatcctga     1260
aagacaccaa gagcataacc agtgccatga atgagctgca gcatgatctc gatgttgtca     1320
gtgatgccct tgctaaggtc agcaggaagc cgagtatcta acagtagcca gtcatccagg     1380
aacatttgag catcaattcg gaggtctggg ccatctcttg ctttccttga cacctgatc     1440 ctggagggac agcatcttct ggccaaacaa tattatcgaa ttccactact taaggaatca     1500
ctagtctttg aaaatttgta cctggatatt ctatttacca cttatttttt tgtttagttt     1560
tatttctttt ttttttggt agcagcttta atgagacaat ttatatacca tacaagccac     1620
tgaccaccca tttttaatag agaagttgtt tgacccaata gatagatcta atctcagcct     1680 aactctatt tccccaatcc tccttgagta aaatgaccct taggatcgc ttagaataac     1740 ttgaggagta ttatggcgct gactcatatt gttacctaag atcccttat ttctaaagta     1800 tctgttactt attgc                                                     1815

<210> SEQ ID NO 3
<211> LENGTH: 447
<212> TYPE: PRT
<213> ORGANISM: Mus sp.

<400> SEQUENCE: 3

Met Ile Glu Asp Asn Lys Glu Asn Lys Asp His Ser Ser
1               5                   10                  15

Glu Arg Gly Arg Val Thr Leu Ile Phe Ser Leu Glu Asn Glu Val Gly
                20                  25                  30

Gly Leu Ile Lys Val Leu Lys Ile Phe Gln Glu Asn His Val Ser Leu
            35                  40                  45

Leu His Ile Glu Ser Arg Lys Ser Lys Gln Arg Asn Ser Glu Phe Glu
        50                  55                  60

Ile Phe Val Asp Cys Asp Ile Ser Arg Glu Gln Leu Asn Asp Ile Phe
65                  70                  75                  80

Pro Leu Leu Lys Ser His Ala Thr Val Leu Ser Val Asp Ser Pro Asp
                85                  90                  95

Gln Leu Thr Ala Lys Glu Asp Val Met Glu Thr Val Pro Trp Phe Pro
            100                 105                 110

Lys Lys Ile Ser Asp Leu Asp Phe Cys Ala Asn Arg Val Leu Leu Tyr
        115                 120                 125
```

Gly Ser Glu Leu Asp Ala Asp His Pro Gly Phe Lys Asp Asn Val Tyr
    130                 135                 140

Arg Arg Arg Arg Lys Tyr Phe Ala Glu Leu Ala Met Asn Tyr Lys His
145                 150                 155                 160

Gly Asp Pro Ile Pro Lys Ile Glu Phe Thr Glu Glu Ile Lys Thr
                165                 170                 175

Trp Gly Thr Ile Phe Arg Glu Leu Asn Lys Leu Tyr Pro Thr His Ala
                180                 185                 190

Cys Arg Glu Tyr Leu Arg Asn Leu Pro Leu Leu Ser Lys Tyr Cys Gly
            195                 200                 205

Tyr Arg Glu Asp Asn Ile Pro Gln Leu Glu Asp Val Ser Asn Phe Leu
210                 215                 220

Lys Glu Arg Thr Gly Phe Ser Ile Arg Pro Val Ala Gly Tyr Leu Ser
225                 230                 235                 240

Pro Arg Asp Phe Leu Ser Gly Leu Ala Phe Arg Val Phe His Cys Thr
                245                 250                 255

Gln Tyr Val Arg His Ser Ser Asp Pro Leu Tyr Thr Pro Glu Pro Asp
            260                 265                 270

Thr Cys His Glu Leu Leu Gly His Val Pro Leu Leu Ala Glu Pro Ser
        275                 280                 285

Phe Ala Gln Phe Ser Gln Glu Ile Gly Leu Ala Ser Leu Gly Ala Ser
    290                 295                 300

Glu Glu Thr Val Gln Lys Leu Ala Thr Cys Tyr Phe Phe Thr Val Glu
305                 310                 315                 320

Phe Gly Leu Cys Lys Gln Asp Gly Gln Leu Arg Val Phe Gly Ala Gly
                325                 330                 335

Leu Leu Ser Ser Ile Ser Glu Leu Lys His Ala Leu Ser Gly His Ala
            340                 345                 350

Lys Val Lys Pro Phe Asp Pro Lys Ile Ala Cys Lys Gln Glu Cys Leu
        355                 360                 365

Ile Thr Ser Phe Gln Asp Val Tyr Phe Val Ser Glu Ser Phe Glu Asp
    370                 375                 380

Ala Lys Glu Lys Met Arg Glu Phe Ala Lys Thr Val Lys Arg Pro Phe
385                 390                 395                 400

Gly Leu Lys Tyr Asn Pro Tyr Thr Gln Ser Val Gln Val Leu Arg Asp
                405                 410                 415

Thr Lys Ser Ile Thr Ser Ala Met Asn Glu Leu Arg Tyr Asp Leu Asp
            420                 425                 430

Val Ile Ser Asp Ala Leu Ala Arg Val Thr Arg Trp Pro Ser Val
        435                 440                 445

<210> SEQ ID NO 4
<211> LENGTH: 4270
<212> TYPE: DNA
<213> ORGANISM: Mus sp.

<400> SEQUENCE: 4
gactctttaa actccagtgg ctctgaggtg agtgggtgag tgggatagcc cctccctggg      60
acatcggatc agaagactcc cagcaaggac gggatcaact tctagtagga accagattca     120
ccatgattga agacaacaag gagaacaaag agaacaaaga ccattcctcc gaaagaggga     180
gagtgactct catcttctcc ttggagaatg aagtcggagg actcataaaa gtgctgaaaa     240
tcttccagga gaatcatgtg agcctgttac acatcgagtc ccggaaatca aagcaaagaa     300
attcagaatt tgagatattt gttgactgcg acatcagccg agaacagttg aatgacatct     360

```
tcccccctgct gaagtcgcac gccaccgtcc tctcggtgga ctcgcccgat cagctcactg     420
cgaaggaaga cgttatggag actgtccctt ggtttccaaa gaagatttct gacctggact     480
tctgcgccaa cagagtgctg ttgtatggat ccgaacttga cgccgaccac cctggcttca     540
aagacaatgt ctatcgtaga agacgaaagt attttgcaga gttggctatg aactacaaac     600
atggggaccc cattcccaag attgaattca cggaagaaga gattaagacc tggggaccca     660
tcttccgaga gctaaacaaa ctctacccga cccacgcctg cagggagtac ctcagaaacc     720 tcccttttgct ctcaaaatac tgtggctatc gggaagacaa catcccgcaa ctggaggatg     780
tctccaactt tttaaaagaa cgcactgggt tttccatccg tcctgtggct ggttacctct     840
caccgagaga ttttctgtcg gggttagcct ttcgagtctt tcactgcact cagtatgtga     900
gacacagttc agatcccctc tacactccag agccagacac ctgccatgaa ctcctaggcc     960
acgttcctct cttggctgaa cccagttttg ctcaattctc caagaaaatt ggcctggctt    1020
cccttggagc ttcagaggag acagttcaaa actggcaac gtgctacttt ttcactgtgg      1080
agtttgggct gtgcaaacaa gatggacagc tgagagtctt tggggccggc ttgctttctt    1140
ccatcagtga actcaaacat gcactttctg gacatgccaa agtcaagccc tttgatccca    1200
agattgcctg taaacaggaa tgtctcatca cgagcttcca ggatgtctac tttgtatctg    1260
agagctttga agatgcaaag gagaagatga gagaatttgc caagaccgtg aagcgcccgt    1320
ttggactgaa gtacaacccg tacacacaga gtgttcaggt tctcagagac accaagagca    1380
taactagtgc catgaatgag ttgcggtatg accttgatgt catcagtgat gccctcgcta    1440
gggtcaccag gtggcccagt gtgtgatggt ttccagtgca tatccaaaaa gcctttgagc    1500
atcagtctag agccagggct agttcttgct tcccctgaag acctgcttgg ggagggacag    1560
cagctcccag cttagcaatg tctctcgcct ctctccatat tcaatcactc actctctctg    1620
aaaatgcaca cctggaactg cttatcttct acttctgttt tgtcttctgg aacctgctga    1680
gggaaatata gttcacgtgc cacgtgatgc ccaggacaca catttaaaat attttatttc    1740
attaaaatgt aattgaatca ttctctccct tcccttctt ccctccaacc cctccctctc     1800
aaattcatgg cctttctacc aaatgcccgt ctttgatggg tgagttgtct gacactggcc    1860
agagctggac tcatggtgat gccattttcc ccagcccatc attagtggat ggcctctctg    1920
gatgccacga tgaatgtgtc tgttacctat tactgactgt gtgacagccc aggcacagtc    1980
acacactaga cttcaagggg actcgctgaa acagaagtgt ggatgacttt gcgctagagc    2040
atggctagta aagtgcaagc tggcttcaag tgctgtgtca gacagggacg tagaagccac    2100
caagactcag ccagtgcttt ctggcacttt gtttcaaggt gtaaccctag gatatagtga    2160
gaaggtatgt gtgtgtgtgt ggggtggtgc agagggtagg aaatgggat gggaatggag      2220 aagggccaaa gggagcagtt tgtatctgag actgtactta tgcgagggag agctgtgagg    2280
attggagcac atgtggtgtc cgcataagca gttgtataag cttttcacta ctgtaacaaa    2340
gtgtcaggga caatcagctt atacagagaa aaggtttctc ttggatgctt tggtccatta    2400
gaagttgttc ccgtggttta agccactggt gaagcaaggc atgataggag aatgtgacag    2460
agcaaacttc ataaagctat acacgtcata aaggatggaa agagaaagag tgaaggattt    2520
tagagaagga agaagggaga gagggaaaga gagggagg aggacacaca cacacacaca      2580
cacacacaaa gggggtgaga gagagagtca gagacagaga cagagacaga aagatcctac    2640
agttcagttt aagagttcac taccagggta agagagaggg ctcagcagtt aagagtacca    2700
```

```
gctgttcttc cagaggaccc tggtttgctt cccagcatcc acactgtggc ttagaaccat    2760
ctgtaactct agttccagag gatccagtgt tttctggcct ccatagagag caggcaggca    2820
tgcaagtggt acacagatat gcatgcagca aaaacaccca tacacataca ataaaaagta    2880 gaagaccota cctctgcttt tcccattaat agtgaaatta tataccattg gacaggcttc    2940
atctcaagcc cactagatat attttcacac tagattttta aaaacacctt ttaaggattc    3000
agaggaaact attgaaagct gcgcttcacc ccatgctcta caaggaagtg taatccagcc    3060
gtctcagatc tttagaaaca tacccactt aacagctggt gagcacgcat ccgtccgcaa    3120
gtagatacgt tagctctgaa atcacctgaa gtacaaacca gctagtttac agcctgcttg    3180
attaccaggg aaagcactat aaagaaatcc taccgacagc aaacagagag tgccgtctgc    3240
tgtttctggt tatttccact agactctggt ggtgctgaag aatcacttat tggctttta    3300 attggttgtg ctctgactaa agcactttaa actgtaaagc cacaaccta ccgtttgtaa    3360 cttcaggata gaaaaataa gcgaagggct tgactttgtc tctgctctgc ttctgtgata    3420
tttggcaagt cagggttcca agagccttgg agtcttcaaa acacctaaga atcttttaat    3480
agttattcaa acaccaggcc agattcaaac aaaaagcaag gcttgcaatt ctttcctgga    3540
gagccattcc tcgacagcag cagcgtgctt gacttttga agaaaacaca aatgctaatc    3600
gtcagagtgc ctgcgttcct taatctcatg ctttggcatt tggaattaca taagtagcaa    3660
gatgcagcaa aatgcacaga attattgctc attttaagt tggcttctaa accacagaaa    3720
gaagaaagcc aggacttctc aaaagcacta ataactgag accgtatgtt catttccagg    3780
aagtggataa aaagataaca gtggtccatt tcactcttca tgttacagtg ccacatacac    3840
ttataattta agaatttgtt ccactgggta ataaacttaa agttcatgat ctcaagaagt    3900 attttttta aagcacattt aaaactttta ttatatgtgt gtgggcccca ggaatcaaac    3960
tccagttgtc aggcttggcc acaagcccct ttatttgctg agccagtttt tgccacccc    4020 tcccccaatt cttttaatca aacacacatt aaaaacagtt tcaattttat gttcacaatg    4080
ttataagttc agagaccota gcagtgatga tggttggtac aaagaatcag ccttgggggt    4140
tagacaaagt atgaacatgc ctcaatggaa cccattactt tgtataccac tttaaaatat    4200
ttttacaaaa agaaatcaca aaatatacaa taaaaaatat acatcactct aaaaaaaaaa    4260
aaaaaaaaaa                                                          4270
```